US011875813B2

(12) United States Patent
Mesgarani et al.

(10) Patent No.: US 11,875,813 B2
(45) Date of Patent: Jan. 16, 2024

(54) SYSTEMS AND METHODS FOR BRAIN-INFORMED SPEECH SEPARATION

(71) Applicant: The Trustees of Columbia University in the City of New York, New York, NY (US)

(72) Inventors: Nima Mesgarani, New York, NY (US); Enea Ceolini, New York, NY (US); Cong Han, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/129,469

(22) Filed: Mar. 31, 2023

(65) Prior Publication Data

US 2023/0377595 A1 Nov. 23, 2023

Related U.S. Application Data

(63) Continuation of application No. PCT/US2021/053560, filed on Oct. 5, 2021.
(Continued)

(51) Int. Cl.
*G10L 21/028* (2013.01)
*G10L 21/0232* (2013.01)
*G10L 21/0208* (2013.01)

(52) U.S. Cl.
CPC ........ *G10L 21/028* (2013.01); *G10L 21/0232* (2013.01); *G10L 2021/02087* (2013.01)

(58) Field of Classification Search
CPC .............. G10L 21/028; G10L 21/0232; G10L 2021/02087
(Continued)

(56) References Cited

U.S. PATENT DOCUMENTS 8,867,763 B2 10/2014 Bouse
9,025,800 B2 5/2015 Kidmose et al.
(Continued)

FOREIGN PATENT DOCUMENTS

WO 2017218492 A1 12/2017

OTHER PUBLICATIONS

Loui P, GrenttJong T, Torpey D, Woldorff M. 2005. Effects of attention on the neural processing of harmonic syntax in western music. Cognitive Brain Research 25:678-687. DOI: https://doi.org/10.1016/j.cogbrainres.2005.08.019, PMID: 16257518.
(Continued)

*Primary Examiner* — Fariba Sirjani
(74) *Attorney, Agent, or Firm* — Potomac Law Group, PLLC

(57) ABSTRACT

Disclosed are methods, systems, device, and other implementations, including a method (performed by, for example, a hearing aid device) that includes obtaining a combined sound signal for signals combined from multiple sound sources in an area in which a person is located, and obtaining neural signals for the person, with the neural signals being indicative of one or more target sound sources, from the multiple sound sources, the person is attentive to. The method further includes determining a separation filter based, at least in part, on the neural signals obtained for the person, and applying the separation filter to a representation of the combined sound signal to derive a resultant separated signal representation associated with sound from the one or more target sound sources the person is attentive to.

17 Claims, 17 Drawing Sheets

Related U.S. Application Data

(60) Provisional application No. 63/087,636, filed on Oct. 5, 2020.

(58) Field of Classification Search
USPC .......................................................... 704/233
See application file for complete search history.

(56) References Cited

U.S. PATENT DOCUMENTS

| | | | |
|---|---|---|---|
| 9,177,559 B2* | 11/2015 | Stephenson | G10L 17/26 |
| 9,432,777 B2* | 8/2016 | Lunner | A61B 5/377 |
| 9,700,261 B2 | 7/2017 | Lunner | |
| 9,734,842 B2* | 8/2017 | Le Magoarou | G10L 21/0232 |
| 9,838,784 B2* | 12/2017 | Vallabhan | H04R 3/005 |
| 9,875,753 B2 | 1/2018 | Ungstrup et al. | |
| 10,225,669 B2 | 3/2019 | Jensen et al. | |
| 10,285,615 B2* | 5/2019 | Kidmose | A61B 5/38 |
| 10,362,414 B2* | 7/2019 | Lunner | A61B 5/369 |
| 11,373,672 B2* | 6/2022 | Mesgarani | G10L 25/30 |
| 11,630,513 B2* | 4/2023 | Ciccarelli | A61B 5/121 715/863 |
| 2005/0240642 A1 | 10/2005 | Parra et al. | |
| 2007/0021958 A1 | 1/2007 | Visser et al. | |
| 2009/0202091 A1* | 8/2009 | Pedersen | H04R 25/407 381/313 |
| 2009/0304203 A1* | 12/2009 | Haykin | H04R 25/407 381/94.1 |
| 2012/0177233 A1* | 7/2012 | Kidmose | G06F 3/015 381/314 |
| 2012/0209132 A1* | 8/2012 | Jones | A61B 7/026 600/528 |
| 2014/0108020 A1* | 4/2014 | Sharma | G10L 19/018 704/500 |
| 2014/0142958 A1* | 5/2014 | Sharma | G10L 19/018 704/500 |
| 2014/0297294 A1 | 10/2014 | Kim et al. | |
| 2015/0063597 A1* | 3/2015 | Daly | H04R 3/04 381/104 |
| 2015/0287422 A1* | 10/2015 | Short | G01S 3/74 704/211 |
| 2016/0005394 A1* | 1/2016 | Hiroe | G10L 21/0272 704/248 |
| 2016/0022991 A1* | 1/2016 | Apoux | A61N 1/36038 607/57 |
| 2017/0178666 A1 | 6/2017 | Yu | |
| 2017/0345433 A1* | 11/2017 | Dittmar | G10L 13/04 |
| 2018/0014130 A1* | 1/2018 | Lunner | A61F 11/06 |
| 2019/0066713 A1* | 2/2019 | Mesgarani | G10L 17/26 |
| 2019/0214011 A1* | 7/2019 | Shin | G10L 21/0272 |
| 2019/0222932 A1* | 7/2019 | Ishizuka | H04S 7/301 |
| 2019/0394568 A1* | 12/2019 | Sen | G06N 3/045 |
| 2020/0005770 A1* | 1/2020 | Lunner | H04R 25/407 |
| 2020/0201435 A1* | 6/2020 | Ciccarelli | G06F 18/22 |
| 2021/0082447 A1* | 3/2021 | Disch | G10L 19/22 |
| 2022/0392482 A1* | 12/2022 | Mesgarani | G10L 25/30 |

OTHER PUBLICATIONS

Lukas Pfeifenberger, Matthias Zohrer, and Franz Perkopf, "Dnn-based speech mask estimation for eigenvector beamforming," in Acoustics, Speech and Signal Processing (ICASSP), 2017 IEEE International Conference on. IEEE, 2017, pp. 66-70.

Luo Y, Mesgarani N. 2018. Conv-TasNet: surpassing ideal Time-Frequency magnitude masking for speech separation. arXiv. https://arxiv.org/abs/1809.07454.

Luo, Y., and Mesgarani, N. (2019). Conv-TasNet: Surpassing Ideal Time-Frequency Magnitude Masking for Speech Separation. IEEE/ACM Trans. Audio, Speech, Lang. Process. 27, 1256-1266.

Luo, Y., Chen, Z., and Mesgarani, N. (2018). Speaker-Independent Speech Separation With Deep Attractor Network. IEEE/ACM Trans. Audio Speech Lang. Process. 26, 787-796.

Luo, Y., Chen, Z., Mesgarani, N., & Yoshioka, T. (2020). End-to-end microphone permutation and number invariant multi-channel speech separation. ICASSP 2020—2020 IEEE International Conference on Acoustics, Speech and Signal Processing (ICASSP), 130-134. https://doi.org/10.1109/icassp40776.2020.9054177.

Luo, Y., Mesgarani, N., 2018. Tasnet: time-domain audio separation network for real-time, single-channel speech separation. 2018 IEEE International Conference on Acoustics, Speech and Signal Processing (ICASSP) 696-700.

Luo, Yi, et al., "Separating Varying Numbers of Sources with Auxiliary Autoencoding Loss," Department of Electrical Engineering, Columbia University, (2020): 39-42.

M. Azarpour and G. Enzner, "Binaural noise reduction via cue preserving mmse filter and adaptive-blocking-based noise psd estimation," EURASIP Journal on Advances in Signal Processing, vol. 2017, No. 1, pp. 1-17, 2017.

M. Kolbæk, D. Yu, Z .-H. Tan, and J. Jensen, "Multitalker speech separation with utterance-level permutation invariant training of deep recurrent neural networks," IEEE/ACM Transactions on Audio, Speech, and Language Processing (TASLP), vol. 25, No. 10, pp. 1901-1913, 2017.

M. Kolbæk, Z .-H. Tan, S. H. Jensen, and J. Jensen, "On loss functions for supervised monaural time-domain speech enhancement," IEEE/ACM Transactions on Audio, Speech, and Language Processing (TASLP), 2020.

M. Sams, M. Hamalainen, R. Hari, and L. McEvoy, "Human auditory cortical mechanisms of sound lateralization: I. interaural time differences within sound," Hearing research, vol. 67, No. 1-2, pp. 89-97, 1993.

Machens CK, Wehr MS, Zador AM. 2004. Linearity of cortical receptive fields measured with natural sounds. Journal of Neuroscience 24:1089-1100. DOI: https://doi.org/10.1523/JNEUROSCI.4445-03.2004, PMID: 14762127.

Mackay D, Mac KD. 2003. Information Theory Inference And Learning Algorithms. Cambridge University Press.

Maess B, Koelsch S, Gunter TC, Friederici AD. 2001. Musical syntax is processed in broca's area: an MEG study. Nature Neuroscience 4:540-545. DOI: https://doi.org/10.1038/87502, PMID: 11319564.

Mallat S. 2016. Understanding deep convolutional networks. Philosophical Transactions of the Royal Society A: Mathematical, Physical and Engineering Sciences 5:203. DOI: https://doi.org/10.1098/rsta.2015.0203.

Manfredi, M., Cohn, N., De Araújo Andreoli, M. & Boggio, P. S. Listening beyond seeing: Event-related potentials to audiovisual processing in visual narrative. Brain Lang. 185, 1-8 (2018).

Manzil Zaheer, Satwik Kottur, Siamak Ravanbakhsh, Barnabas Poczos, Ruslan R Salakhutdinov, and Alexander J Smola, "Deep sets," in Advances in neural information processing systems, 2017, pp. 3391-3401.

Margulis EH. 2005. A model of melodic expectation. Music Perception: An Interdisciplinary Journal 22:663-714. DOI: https://doi.org/10.1525/mp.2005.22.4.663.

Mayo, L. H., Florentine, M. & Buus, S. Age of second-language acquisition and perception of speech in noise. J. Speech, Lang. Hear. Res. 40, 686-693 (1997).

McFarland JM, Cui Y, Butts DA. 2013. Inferring nonlinear neuronal computation based on physiologically plausible inputs. PLOS Computational Biology 9:e1003143. DOI: https://doi.org/10.1371/journal.pcbi.1003143, PMID: 23874185.

McGettigan C, Faulkner A, Altarelli I, Obleser J, Baverstock H, Scott SK. 2012. Speech comprehension aided by multiple modalities: behavioural and neural interactions. Neuropsychologia 50:762-776. DOI: https://doi.org/10.1016/j.neuropsychologia.2012.01.010, PMID: 22266262.

McIntosh LT, Maheswaranathan N, Nayebi A, Ganguli S, Baccus SA. 2016. Deep learning models of the retinal response to natural scenes. Advances in Neural Information Processing Systems 1369-1377.

McLaughlin, J., Osterhout, L. & Kim, A. Neural correlates of second-language word learning: Minimal instruction produces rapid change. Nat. Neurosci. 7, 703-704 (2004).

(56) References Cited

OTHER PUBLICATIONS

McMurray, B., and Jongman, A. (2011). What information is necessary for speech categorization? Harnessing variability in the speech signal by integrating cues computed relative to expectations. Psychol. Rev. 118, 219.

Mehta AD, Klein G. 2010. Clinical utility of functional magnetic resonance imaging for brain mapping in epilepsy surgery. Epilepsy Research 89:126-132. DOI: https://doi.org/10.1016/j.eplepsyres.2009.12.001, PMID: 20211545.

Meltzer, J. A. & Braun, A. R. P600-like positivity and left anterior negativity responses are elicited by semantic reversibility in nonanomalous sentences. J. Neurolinguistics 26, 129-148 (2013).

Mesgarani N, David SV, Fritz JB, Shamma SA. 2014a. Mechanisms of noise robust representation of speech in primary auditory cortex. PNAS 111:6792-6797. DOI: https://doi.org/10.1073/pnas.1318017111, PMID: 24753585.

Mesgarani, N., Chang, E.F., 2012. Selective cortical representation of attended speaker in multi-talker speech perception. Nature 485 (7397), 233-236.

Mesgarani, N., Cheung, C., Johnson, K., and Chang, E.F. (2014). Phonetic Feature Encoding in Human Superior Temporal Gyrus. Science 343, 1006-1010.

Mesgarani, N., David, S.V., Fritz, J.B., and Shamma, S.A. (2009b). Influence of context and behavior on stimulus reconstruction from neural activity in primary auditory cortex. J. Neurophysiol. 102, 3329-3339.

Mesgarani, N., David, S.V.S.V., Fritz, J.B.J.B., and Shamma, S.A.S.A. (2008). Phoneme representation and classification in primary auditory cortex. J. Acoust. Soc. Am. 123, 899-909.

Mesgarani, N., Fritz, J., and Shamma, S. (2010). A computational model of rapid task-related plasticity of auditory cortical receptive fields. J. Comput. Neurosci. 28, 19-27.

Mesgarani, N., Sivaram, G.S.V.S., Nemala, S.K., Elhilali, M., and Hermansky, H. (2009a). Discriminant spectrotemporal features for phoneme recognition. In Proceedings of the Annual Conference of the International Speech Communication Association, Interspeech, pp. 2983-2986.

Mesgarani, N., Slaney, M., and Shamma, S.A. (2006). Discrimination of speech from nonspeech based on multiscale spectro-temporal modulations. IEEE Trans. Audio. Speech. Lang. Processing 14, 920-930.

Meyer AF, Williamson RS, Linden JF, Sahani M. 2016. Models of neuronal Stimulus-Response functions: elaboration, estimation, and evaluation. Frontiers in Systems Neuroscience 10:109. DOI: https://doi.org/10.3389/fnsys.2016.00109, PMID: 28127278.

Michael E Lockwood, Douglas L Jones, Robert C Bilger, Charissa R Lansing, William D OBrien Jr, Bruce C Wheeler, and Albert S Feng, "Performance of time-and frequency domain binaural beamformers based on recorded signals from real rooms," The Journal of the Acoustical Society of America, vol. 115, No. 1, pp. 379-391, 2004.

Michael S Brandstein and Harvey F Silverman, "A robust method for speech signal time-delay estimation in reverberant rooms," in Acoustics, Speech, and Signal Processing, 1997. ICASSP-97., 1997 IEEE International Conference on. IEEE, 1997, vol. 1, pp. 375-378.

Mikolov, T., Chen, K., Corrado, G. & Dean, J. Efficient estimation of word representations in vector space. in 1st International Conference on Learning Representations, ICLR 2013—Workshop Track Proceedings (International Conference on Learning Representations, ICLR, 2013).

Miller KJ, Leuthardt EC, Schalk G, Rao RP, Anderson NR, Moran DW, Miller JW, Ojemann JG. 2007. Spectral changes in cortical surface potentials during motor movement. Journal of Neuroscience 27:2424-2432. DOI: https://doi.org/10.1523/JNEUROSCI.3886-06.2007, PMID: 17329441.

Miller, L.M., Escab, M.A., Read, H.L., and Schreiner, C.E. (2002). Spectrotemporal receptive fields in the lemniscal auditory thalamus and cortex J. Neurophysiol. 87, 516-527.

Miller, L.M., Escab, M.A., Read, H.L., and Schreiner, C.E. (2001). Functional convergence of response properties in the auditory thalamocortical system. Neuron 32, 151-160.

Mingsian Bai, Jeong-Guon Ih, and Jacob Benesty, Time-Domain MVDR Array Filter for Speech Enhancement, chapter 7, pp. 287-314, IEEE, 2013.

Miran, S., Akram, S., Sheikhattar, A., Simon, J.Z., Zhang, T., Babadi, B., 2018. Real-time tracking of selective auditory attention from m/eeg: a bayesian filtering approach. Front Neurosci 12, 262. doi: 10.3389/fnins.2018.00262.

Miranda RA, Ullman MT. 2007. Double dissociation between rules and memory in music: an event-related potential study. NeuroImage 38:331-345. DOI: https://doi.org/10.1016/j.neuroimage.2007.07.034, PMID: 17855126.

Moerel M, De Martino F, Formisano E. 2014. An anatomical and functional topography of human auditory cortical Areas. Frontiers in Neuroscience 8:225. DOI: https://doi.org/10.3389/fnins.2014.00225, PMID: 25120426.

Moerel, M., De Martino, F., and Formisano, E. (2012). Processing of natural sounds in human auditory cortex: tonotopy, spectral tuning, and relation to voice sensitivity. J. Neurosci. 32, 14205-14216.

Moldwin T, Schwartz O, Sussman ES. 2017. Statistical learning of melodic patterns influences the brain's Response to Wrong Notes. Journal of Cognitive Neuroscience 29:2114-2122. DOI: https://doi.org/10.1162/jocn_a_01181.

Molenberghs, P., Mesulam, M.M., Peeters, R., and Vandenberghe, R.R.C. (2007). Remapping attentional priorities: differential contribution of superior parietal lobule and intraparietal sulcus. Cereb. Cortex 17, 2703-2712.

Moon Ju Jo, Geon Woo Lee, Jung Min Moon, Choongsang Cho, and Hong Kook Kim, "Estimation of mvdr beamforming weights based on deep neural network," in Audio Engineering Society Convention 145. Audio Engineering Society, 2018.

Morgan E, Fogel A, Nair A, Patel AD. 2019. Statistical learning and Gestalt-like principles predict melodic expectations. Cognition 189:23-34. DOI: https://doi.org/10.1016/j.cognition.2018.12.015, PMID: 30913527.

Morgan-Short, K., Finger, I., Grey, S. & Ullman, M. T. Second Language Processing Shows Increased Native-Like Neural Responses after Months of No Exposure. PLoS One 7, e32974 (2012).

Morosan, P., Rademacher, J., Palomero-Gallagher, N., and Zilles, K. (2005). Anatomical organization of the human auditory cortex: cytoarchitecture and transmitter receptors. In The Auditory Cortex,(Psychology Press), pp. 45-68.

Morosan, P., Rademacher, J., Schleicher, A., Amunts, K., Schormann, T., and Zilles, K. (2001). Human primary auditory cortex: cytoarchitectonic subdivisions and mapping into a spatial reference system. Neuroimage 13, 684-701.

Morrison SJ, Demorest SM, Stambaugh LA. 2008. Enculturation effects in music cognition. Journal of Research in Music Education 56:118-129. DOI: https://doi.org/10.1177/0022429408322854.

Mountcastle VB. 1957. Modality and topographic properties of single neurons of cat's somatic sensory cortex. Journal of Neurophysiology 20:408-434. DOI: https://doi.org/10.1152/jn.1957.20.4.408, PMID: 13439410.

Mueller, J. L. Electrophysiological correlates of second language processing. Second Lang. Res. 21, 152-174 (2005).

Murray MM, Brunet D, Michel CM. 2008. Topographic ERP analyses: a step-by-step tutorial review. Brain Topography 20:249-264. DOI: https://doi.org/10.1007/s10548-008-0054-5, PMID: 18347966.

(56) References Cited

OTHER PUBLICATIONS

N. Takahashi, S. Parthasaarathy, N. Goswami, and Y. Mitsufuji, "Recursive speech separation for unknown number of speakers," Interspeech 2019, pp. 1348-1352, 2019.

Nagamine T, Mesgarani N. 2017. Understanding the representation and computation of multilayer perceptrons: a case study in speech recognition. International Conference on Machine Learning 2564-2573.

Nair V, Hinton GE. 2010. Rectified linear units improve restricted boltzmann machines. Proceedings of the 27th International Conference on Machine Learning (ICML-10 807-814.

Nelson, M.J., El Karoui, I., Giber, K., Yang, X., Cohen, L., Koopman, H., Cash, S.S., Naccache, L., Hale, J.T., Pallier, C., and Dehaene, S. (2017). Neurophysiological dynamics of phrase-structure building during sentence processing. Proc. Natl. Acad. Sci. USA 114, E3669-E3678.

Norman-Haignere, S., Kanwisher, N.G., and McDermott, J.H. (2015). Distinct cortical pathways for music and speech revealed by hypothesis-free voxel decomposition. Neuron 88, 1281-1296.

Norris D, McQueen JM, Cutler A. 2016. Prediction, bayesian inference and feedback in speech recognition. Language, Cognition and Neuroscience 31:4-18. DOI: https://doi.org/10.1080/23273798.2015.1081703, PMID: 26740960.

Nourski KV, Steinschneider M, Rhone AE, Kawasaki H, Howard MA, Banks MI. 2018. Processing of auditory novelty across the cortical hierarchy: an intracranial electrophysiology study. NeuroImage 183:412-424. DOI: https://doi.org/10.1016/j.neuroimage.2018.08.027, PMID: 30114466.

Nourski, K. V, Steinschneider, M., McMurray, B., Kovach, C.K., Oya, H., Kawasaki, H., and Howard, M.A. (2014). Functional organization of human auditory cortex: investigation of response latencies through direct recordings. Neuroimage 101, 598-609.

Nourski, K.V. (2017). Auditory processing in the human cortex: An intracranial electrophysiology perspective. Laryngoscope Investig. Otolaryngol. 2, 147-156.

Nourski, K.V., Steinschneider, M., Oya, H., Kawasaki, H., and Howard, M.A., 3rd (2015). Modulation of response patterns in human auditory cortex during a target detection task: an intracranial electrophysiology study. Int. J. Psychophysiol. 95, 191-201.

Nourski, K.V., Steinschneider, M., Rhone, A.E., and Howard Iii, M.A. (2017). Intracranial Electrophysiology of Auditory Selective Attention Associated with Speech Classification Tasks. Front. Hum. Neurosci. 10, 691.

Nourski, K.V., Steinschneider, M., Rhone, A.E., Kovach, C.K., Kawasaki, H., and Howard, M.A., 3rd (2019). Differential responses to spectrally degraded speech within human auditory cortex: An intracranial electrophysiology study. Hear. Res. 371, 53-65.

O'Sullivan JA, Power AJ, Mesgarani N, Rajaram S, Foxe JJ, Shinn-Cunningham BG, Slaney M, Shamma SA, Lalor EC. 2015. Attentional selection in a cocktail party environment can be decoded from Single-Trial EEG. Cerebral Cortex 25:1697-1706. DOI: https://doi.org/10.1093/cercor/bht355.

O'Sullivan, J., Chen, Z., Herrero, J., McKhann, G.M.G.M., Sheth, S.A.S.A., Mehta, A.D.A.D., Mesgarani, N., et al. (2017). Neural decoding of attentional selection in multi-speaker environments without access to clean sources. J. Neural Eng. 14, 056001.

O'Sullivan, J.A., Shamma, S.A., and Lalor, E.C. (2015). Evidence for neural computations of temporal coherence in an auditory scene and their enhancement during active listening. J. Neurosci. 35, 7256-7263.

O'Sullivan, James, et al., "Hierarchical Encoding of Attended Auditory Objects in Multi-talker Speech Perception," Neuron, 104 (2019): 1195-1209.

O.Cetin and E. Shriberg, "Analysis of overlaps in meetings by dialog factors, hot spots, speakers, and collection site: Insights for automatic speech recognition," in Ninth International Conference on Spoken Language Processing, 2006.

Obleser, J. & Kayser, C. Neural Entrainment and Attentional Selection in the Listening Brain. Trends in Cognitive Sciences 23, 913-926 (2019).

Obleser, J., Zimmermann, J., Van Meter, J., and Rauschecker, J.P. (2007). Multiple stages of auditory speech perception reflected in event-related FMRI. Cereb. Cortex 17, 2251-2257.

Dechslin MS, Van De Ville D, Lazeyras F, Hauert C-A, James CE. 2013. Degree of Musical Expertise Modulates Higher Order Brain Functioning. Cerebral Cortex 23:2213-2224. DOI: https://doi.org/10.1093/cercor/bhs206.

Ojima, S., Nakata, H. & Kakigi, R. An ERP study of second language learning after childhood: effects of proficiency. J. Cogn. Neurosci. 17, 1212-28 (2005).

Omigie D, Pearce M, Lehongre K, Hasboun D, Navarro V, Adam C, Samson S. 2019. Intracranial recordings and computational modeling of music reveal the time course of prediction error signaling in frontal and temporal cortices. Journal of Cognitive Neuroscience 31:855-873. DOI: https://doi.org/10.1162/jocn_a_01388, PMID: 30883293.

Omigie D, Pearce MT, Williamson VJ, Stewart L. 2013. Electrophysiological correlates of melodic processing in congenital amusia. Neuropsychologia 51:1749-1762. DOI: https://doi.org/10.1016/j.neuropsychologia.2013.05.010, PMID: 23707539.

Omote, A., Jasmin, K. & Tierney, A. Successful non-native speech perception is linked to frequency following response phase consistency. Cortex 93, 146-154 (2017).

Oreinos, C., Buchholz, J.M., 2013. Measurement of a full 3d set of hrtfs for in-ear and hearing aid microphones on a head and torso simulator (hats). Acta Acustica united with Acustica 99 (5), 836-844.

Osterhout L, Holcomb P. 1995. Event—Related Potentials and Language. In: Electrophysiology of the Mind: Event—Related Brain Potentials and Cognition. Oxford University Press. p. 171-187.

Osterhout, L. et al. Second-language learning and changes in the brain. J. Neurolinguistics 21, 509-521 (2008).

Overath, T., McDermott, J.H., Zarate, J.M., and Poeppel, D. (2015). The cortical analysis of speech specific temporal structure revealed by responses to sound quilts. Nat. Neurosci. 18, 903-911.

Overath, T., Zhang, Y., Sanes, D.H., and Poeppel, D. (2012). Sensitivity to temporal modulation rate and spectral bandwidth in the human auditory system: fMRI evidence. J. Neurophysiol. 107, 2042-2056.

P. Dadvar and M. Geravanchizadeh, "Robust binaural speech separation in adverse conditions based on deep neural network with modified spatial features and training target," Speech Communication, vol. 108, pp. 41-52, 2019.

Paller KA, McCarthy G, Wood CC. 1992. Event-related potentials elicited by deviant endings to melodies. Psychophysiology 29:202-206. DOI: https://doi.org/10.1111/j.1469-8986.1992.tb01686.x, PMID: 1635962.

Paninski L. 2004. Maximum likelihood estimation of cascade point-process neural encoding models. Network: Computation in Neural Systems 15:243-262. DOI: https://doi.org/10.1088/0954-898X_15_4_002.

Pantev C, Roberts LE, Schulz M, Engelien A, Ross B. 2001. Timbre-specific enhancement of auditory cortical representations in musicians. Neuroreport 12:169-174. DOI: https://doi.org/10.1097/00001756-200101220-00041, PMID: 11201080.

Papademetris, X., Jackowski, M.P., Rajeevan, N., DiStasio, M., Okuda, H., Constable, R.T., and Staib, L.H. (2006). BioImage Suite: An integrated medical image analysis suite: An update. Insight J. 2006, 209.

Pascanu R, Cho K, Bengio Y. 2014. On the number of linear regions of deep neural networks. arXiv. https://arxiv.org/abs/1402.1869.

Patel AD. 2003. Language, music, syntax and the brain. Nature Neuroscience 6:674-681. DOI: https://doi.org/10.1038/nn1082, PMID: 12830158.

Patel, P., Long, L.K., Herrero, J.L., Mehta, A.D., and Mesgarani, N. (2018). Joint Representation of Spatial and Phonetic Features in the Human Core Auditory Cortex. Cell Rep. 24, 2051-2062.e2.

Pearce MT, Mullensiefen D, Wiggins GA. 2010a. The role of expectation and probabilistic learning in auditory boundary perception: a model comparison. Perception 39:1367-1391. DOI: https://doi.org/10.1068/p6507.

(56) References Cited

OTHER PUBLICATIONS

Pearce MT, Ruiz MH, Kapasi S, Wiggins GA, Bhattacharya J. 2010b. Unsupervised statistical learning underpins computational, behavioural, and neural manifestations of musical expectation. NeuroImage 50:302-313. DOI: https://doi.org/10.1016/j.neuroimage.2009.12.019, PMID: 20005297.

Pearce MT, Wiggins GA. 2006. Expectation in melody: the influence of context and learning. Music Perception 23:377-405. DOI: https://doi.org/10.1525/mp.2006.23.5.377.

Pearce MT, Wiggins GA. 2012. Auditory expectation: the information dynamics of music perception and cognition. Topics in Cognitive Science 4:625-652. DOI: https://doi.org/10.1111/j.1756-8765.2012.01214.x, PMID: 22847872.

Pearce MT. 2005. The construction and evaluation of statistical models of melodic structure in music perception and composition (unpublished doctoral thesis). City University London.

Hickok G, Saberi K. 2012. Redefining the Functional Organization of the Planum Temporale Region: Space, Objects and Sensory-Motor Integration. Springer. DOI: https://doi.org/10.1007/978-1-4614-2314-0_12.

Hickok, G. & Poeppel, D. The cortical organization of speech processing. Nat Rev Neurosci 8, 393-402 (2007).

Hill, K.T., and Miller, L.M. (2010). Auditory attentional control and selection during cocktail party listening. Cereb. Cortex 20, 583-590.

Hinton GE, Osindero S, Teh YW. 2006. A fast learning algorithm for deep belief nets. Neural Computation 18: 1527-1554. DOI: https://doi.org/10.1162/neco.2006.18.7.1527, PMID: 16764513.

Hjortkjær, J., Märcher-Rørsted, J., Fuglsang, S.A., Dau, T., 2020. Cortical oscillations and entrainment in speech processing during working memory load. European Journal of Neuroscience 51 (5), 1279-1289.

Tong S, Lundstrom BN, Fairhall AL. 2008. Intrinsic gain modulation and adaptive neural coding. PLOS Computational Biology 4:e1000119. DOI: https://doi.org/10.1371/journal.pcbi.1000119, PMID: 18636100.

Hornik K, Stinchcombe M, White H. 1989. Multilayer feedforward networks are universal approximators. Neural Networks 2:359-366. DOI: https://doi.org/10.1016/0893-6080(89)90020-8.

Horton, C., Srinivasan, R., D'zmura, M., 2014. Envelope responses in single-trial eeg indicate attended speaker in a cocktail party . . . J. Neural. Eng. 11 4, 046015.

Howard III, M.A., Volkov, I.O., Abbas, P.J., Damasio, H., Ollendieck, M.C., and Granner, M.A. (1996). A chronic microelectrode investigation of the tonotopic organization of human auditory cortex. Brain Res. 724, 260-264.

Hubel DH, Wiesel TN. 1959. Receptive fields of single neurones in the cat's striate cortex. The Journal of Physiology 148:574-591. DOI: https://doi.org/10.1113/jphysiol.1959.sp006308.

Hubel DH, Wiesel TN. 1962. Receptive fields, binocular interaction and functional architecture in the cat's visual cortex. The Journal of Physiology 160:106-154. DOI: https://doi.org/10.1113/jphysiol.1962.sp006837, PMID: 14449617.

Huettig, F. & Mani, N. Language, Cognition and Neuroscience Is prediction necessary to understand language? Probably not. (2015). doi:10.1080/23273798.2015.1072223.

Hullett, P.W., Hamilton, L.S., Mesgarani, N., Schreiner, C.E., and Chang, E.F. (2016). Human Superior Temporal Gyrus Organization of Spectrotemporal Modulation Tuning Derived from Speech Stimuli. J. Neurosci. 36, 2014-2026.

Humphries, C., Liebenthal, E., and Binder, J.R. (2010). Tonotopic organization of human auditory cortex. Neuroimage 60, 1202-1211.

Tuth, A.G., de Heer, W.A., Griffiths, T.L., Theunissen, F.E., and Gallant, J.L. (2016). Natural speech reveals the semantic maps that tile human cerebral cortex. Nature 532, 453-458.

I. Kavalerov, S. Wisdom, H. Erdogan, B. Patton, K. Wilson, J. Le Roux, and J. R. Hershey, "Universal sound separation," in 2019 IEEE Workshop on Applications of Signal Processing to Audio and Acoustics (WASPAA). IEEE, 2019, pp. 175-179.

J. I. Marin-Hurtado, D. N. Parikh, and D. V. Anderson, "Perceptually inspired noise-reduction method for binaural hearing aids," IEEE transactions on audio, speech, and language processing, vol. 20, No. 4, pp. 1372-1382, 2011.

J. Le Roux, G. Wichern, S. Watanabe, A. Sarroff, and J. R. Hershey, "The phasebook: Building complex masks via discrete representations for source separation," in Acoustics, Speech and Signal Processing (ICASSP), 2019 IEEE International Conference on. IEEE, 2019, pp. 66-70.

J. R. Hershey, Z. Chen, J. Le Roux, and S. Watanabe, "Deep clustering: Discriminative embeddings for segmentation and separation," in Acoustics, Speech and Signal Processing (ICASSP), 2016 IEEE International Conference on. IEEE, 2016, pp. 31-35.

J. Shi, J. Xu, and B. Xu, "Which ones are speaking? speaker inferred model for multi-talker speech separation," Interspeech 2019, pp. 4609-4613, 2019.

J. Shi, J. Xu, G. Liu, and B. Xu, "Listen, think and listen again: capturing top-down auditory attention for speaker-independent speech separation," in Proceedings of the 27th International Joint Conference on Artificial Intelligence. AAAI Press, 2018, pp. 4353-4360.

J. Thiemann, N. Ito, and E. Vincent, "Demand: a collection of multi-channel recordings of acoustic noise in diverse environments," in Proc. Meetings Acoust., 2013.

Jack Capon, "High-resolution frequency-wavenumber spectrum analysis," Proceedings of the IEEE, vol. 57, No. 8, pp. 1408-1418, 1969.

Jahn Heymann, Lukas Drude, Aleksej Chinaev, and Reinhold Haeb-Umbach, "Blstm supported gev beamformer front-end for the 3rd chime challenge," in Automatic Speech Recognition and Understanding (ASRU), 2015 IEEE Workshop on. IEEE, 2015, pp. 444-451.

Jahn Heymann, Lukas Drude, and Reinhold Haeb-Umbach, "Neural network based spectral mask estimation for acoustic beamforming," in Acoustics, Speech and Signal Processing (ICASSP), 2016 IEEE International Conference on. IEEE, 2016, pp. 196-200.

Jahn Heymann, Lukas Drude, Christoph Boeddeker, Patrick Hanebrink, and Reinhold Haeb-Umbach, "Beamnet: End-toend training of a beamformer-supported multi-channel asr system," in Acoustics, Speech and Signal Processing (ICASSP), 2017 IEEE International Conference on. IEEE, 2017, pp. 5325-5329.

Jahn Heymann, Michiel Bacchiani, and Tara N. Sainath, "Performance of mask based statistical beamforming in a smart home scenario," in Acoustics, Speech and Signal Processing (ICASSP), 2018 IEEE International Conference on. IEEE, 2018, pp. 6722-6726.

Jentschke S, Koelsch S. 2009. Musical training modulates the development of syntax processing in children. NeuroImage 47:735-744. DOI: https://doi.org/10.1016/j.neuroimage.2009.04.090, PMID: 19427908.

Jessen, S., Fiedler, L., Münte, T. F. & Obleser, J. Quantifying the individual auditory and visual brain response in 7-month-old infants watching a brief cartoon movie. Neuroimage 202, 116060 (2019).

Jiaxin Li, Ben M. Chen, and Gim Hee Lee, "So-net: Selforganizing network for point cloud analysis," in Proceedings of the IEEE conference on computer vision and pattern recognition, 2018, pp. 9397-9406.

John S Garofolo, Lori F Lamel, William M Fisher, Jonathan G Fiscus, and David S Pallett, "Timit acoustic-phonetic continous speech corpus cd-rom. nist speech disc 1-1.1," NASA STI/Recon technical report n, vol. 93, 1993.

Jon Barker, Ricard Marxer, Emmanuel Vincent, and Shinji Watanabe, "The third chime speech separation and recognition challenge: Dataset, task and baselines," 2015 IEEE Workshop on Automatic Speech Recognition and Understanding (ASRU), pp. 504-511, 2015.

Jont B Allen and David A Berkley, "Image method for efficiently simulating small-room acoustics," The Journal of the Acoustical Society of America, vol. 65, No. 4, pp. 943-950, 1979.

K. Kinoshita, L. Drude, M. Delcroix, and T. Nakatani, "Listening to each speaker one by one with recurrent selective hearing networks," in Acoustics, Speech and Signal Processing (ICASSP), 2018 IEEE International Conference on. IEEE, 2018, pp. 5064-5068.

(56) References Cited

OTHER PUBLICATIONS

K. Reindl, Y. Zheng, and W. Kellermann, "Analysis of two generic wiener filtering concepts for binaural speech enhancement in hearing aids," in 2010 18th European Signal Processing Conference. IEEE, 2010, pp. 989-993.
K. Wang, F. Soong, and L. Xie, "A pitch-aware approach to single-channel speech separation," in Acoustics, Speech and Signal Processing (ICASSP), 2019 IEEE International Conference on. IEEE, 2019, pp. 296-300.
Kaardal JT, Theunissen FE, Sharpee TO. 2017. A Low-Rank method for characterizing High-Level neural computations. Frontiers in Computational Neuroscience 11:68. DOI: https://doi.org/10.3389/fncom.2017. 00068, PMID: 28824408.
Kaizhi Qian, Yang Zhang, Shiyu Chang, Xuesong Yang, Dinei Florencio, and Mark Hasegawa-Johnson, "Deep learning based speech beamforming," in Acoustics, Speech and Signal Processing (ICASSP), 2018 IEEE International Conference on. IEEE, 2018, pp. 5389-5393.
Kajikawa, Y., de La Mothe, L., Blumell, S., and Hackett, T.A. (2005). A comparison of neuron response properties in areas A1 and CM of the marmoset monkey auditory cortex: tones and broadband noise J. Neurophysiol. 93, 22-34.
Kartushina, N. & Frauenfelder, U. H. On the effects of L2 perception and of individual differences in L1 production on L2 pronunciation. Front. Psychol. 5, (2014).
Kell AJE, Yamins DLK, Shook EN, Norman-Haignere SV, McDermott JH. 2018. A Task-Optimized neural network replicates human auditory behavior, predicts brain responses, and reveals a cortical processing hierarchy. Neuron 98:630-644. DOI: https://doi.org/10.1016/j.neuron.2018.03.044, PMID: 29681533.
Kellenbach, M. L., Wijers, A. A. & Mulder, G. Visual semantic features are activated during the processing of concrete words: Event-related potential evidence for perceptual semantic priming. Cogn. Brain Res. 10, 67-75 (2000).
Keller, C.J., Honey, C.J., Entz, L., Bickel, S., Groppe, D.M., Toth, E., Ulbert, I., Lado, F.A., and Mehta, A.D. (2014). Corticocortical evoked potentials reveal projectors and integrators in human brain networks. J. Neurosci. 34, 9152-9163.
Kerlin, J.R., Shahin, A.J., Miller, L.M., 2010. Attentional gain control of ongoing cortical speech representations in a "cocktail party". J. Neurosci. 30 (2), 620-628. doi: 10.1523/JNEUROSCI.3631-09.2010.
Kessler EJ, Hansen C, Shepard RN. 1984. Tonal schemata in the perception of music in Bali and in the west. Music Perception: An Interdisciplinary Journal 2:131-165. DOI: https://doi.org/10.2307/40285289.
Keyulu Xu, Weihua Hu, Jure Leskovec, and Stefanie Jegelka, "How powerful are graph neural networks?," arXiv preprint arXiv:1810.00826, 2018.
Khachatryan, E., Camarrone, F., Fias, W. & Van Hulle, M. M. ERP Response Unveils Effect of Second Language Manipulation on First Language Processing. PLoS One 11, e0167194 (2016).
Khalighinejad, B., da Silva, G.C., and Mesgarani, N. (2017a). Dynamic Encoding of Acoustic Features in Neural Responses to Continuous Speech. J. Neurosci. 37, 2176-2185.
Khalighinejad, B., Herrero, J.L., Mehta, A.D., and Mesgarani, N. (2019). Adaptation of the human auditory cortex to changing background noise. Nat. Commun. 10, 2509.
Khalighinejad, B., Nagamine, T., Mehta, A., and Mesgarani, N. (2017b). NAPLib: An open source toolbox for real-time and offline Neural Acoustic Processing. In Acoustics, Speech and Signal Processing (ICASSP), 2017 IEEE International Conference On, (IEEE), pp. 846-850.
Broderick, M. P., Anderson, A. J., Di Liberto, G. M., Crosse, M. J. & Lalor, E. C. Electrophysiological Correlates of Semantic Dissimilarity Reflect the Comprehension of Natural, Narrative Speech. Curr. Biol. (2018). doi:10.1016/j.cub.2018.01.080.
Brodmann, K. (1909). Vergleichende Lokalisationslehre der Grosshirnrinde in ihren Prinzipien dargestellt auf Grund des Zellenbaues (Barth).
Brugge, J.F., Nourski, K. V, Oya, H., Reale, R.A., Kawasaki, H., Steinschneider, M., and Howard III, M.A. (2009). Coding of repetitive transients by auditory cortex on Heschl's gyrus. J. Neurophysiol. 102, 2358-2374.
Brungart, D.S., Simpson, B.D., Ericson, M.A., and Scott, K.R. (2001). Informational and energetic masking effects in the perception of multiple simultaneous talkers. J. Acoust. Soc. Am. 110, 2527-2538.
Butts DA, Weng C, Jin J, Alonso JM, Paninski L. 2011. Temporal precision in the visual pathway through the interplay of excitation and stimulus-driven suppression. Journal of Neuroscience 31:11313-11327. DOI: https://doi.org/10.1523/JNEUROSCI.0434-11.2011, PMID: 21813691.
Buzsáki, G., Anastassiou, C.A., and Koch, C. (2012). The origin of extracellular fields and currents-EEG, ECoG, LFP and spikes. Nat. Rev. Neurosci. 13, 407-420.
Camalier, C.R., D'Angelo, W.R., Sterbing-D'Angelo, S.J., Lisa, A., and Hackett, T.A. (2012). Neural latencies across auditory cortex of macaque support a dorsal stream supramodal timing advantage in primates. Proc. Natl. Acad. Sci. 109, 18168-18173.
Campbell, A.W. (1905). Histological studies on the localisation of cerebral function (University Press).
Cao, F., Tao, R., Liu, L., Perfetti, C. A. & Booth, J. R. High proficiency in a second language is characterized by greater involvement of the first language network: Evidence from Chinese learners of English. J. Cogn. Neurosci. 25, 1649-1663 (2013).
Carlsen JC. 1981. Some factors which influence melodic expectancy. Psychomusicology: A Journal of Research in Music Cognition 1:12-29. DOI: https://doi.org/10.1037/h0094276.
Carrus E, Pearce MT, Bhattacharya J. 2013. Melodic pitch expectation interacts with neural responses to syntactic but not semantic violations. Cortex 49:2186-2200. DOI: https://doi.org/10.1016/j.cortex 2012.08.024.
Ceolini, E., Kiselev, I., Liu, S.-C., 2020. Evaluating multi-channel multi-device speech sep-aration algorithms in the wild: a hardware-software solution. IEEE/ACM Trans Audio Speech Lang Process 28, 1428-1439.
Ceolini, E., Liu, S., 2019. Combining deep neural networks and beamforming for real-time multi-channel speech enhancement using a wireless acoustic sensor network. In: 2019 IEEE 29th International Workshop on Machine Learning for Signal Processing (MLSP), pp. 1-6.
Ceolini, Enea, et al., "Brain-informed speech separation (BISS) for enhancement of target speaker in multitalker speech perception," NeuroImage, 223 (2020) : 8-19.
Chan, A.M., Dykstra, A.R., Jayaram, V., Leonard, M.K., Travis, K.E., Gygi, B., Baker, J.M., Eskandar, E., Hochberg, L. R., and Halgren, E. (2013). Speech-Specific Tuning of Neurons in Human Superior Temporal Gyrus. Cereb. Cortex.
Chang, C. B. & Mishler, A. Evidence for language transfer leading to a perceptual advantage for non-native listeners. J. Acoust. Soc. Am. 132, 2700-2710 (2012).
Chang, C. B. Rapid and multifaceted effects of second-language learning on first-language speech production. J. Phon. 40, 249-268 (2012).
Chang, C. B. The phonetics of second language learning and bilingualism. in The Routledge Handbook of Phonetics 427-447 (2019). doi:10.4324/9780429056253-16.
Chang, E.F., Rieger, J.W., Johnson, K., Berger, M.S., Barbaro, N.M., and Knight, R.T. (2010). Categorical speech representation in human superior temporal gyrus. Nat. Neurosci. 13, 1428-1432.
Charles Knapp and Glifford Carter, "The generalized correlation method for estimation of time delay," IEEE transactions on acoustics, speech, and signal processing, vol. 24, No. 4, pp. 320-327, 1976.
Chechik G, Anderson MJ, Bar-Yosef O, Young ED, Tishby N, Nelken I. 2006. Reduction of information redundancy in the ascending auditory pathway. Neuron 51:359-368. DOI: https://doi.org/10.1016/j.neuron.2006.06.030, PMID: 16880130.
Chen, Q. et al. Automatic processing of taxonomic and thematic relations in semantic priming—Differentiation by early N400 and late frontal negativity. Neuropsychologia 64, 54-62 (2014).

(56) References Cited

OTHER PUBLICATIONS

Chennu S, Noreika V, Gueorguiev D, Blenkmann A, Kochen S, Ibanez A, Owen AM, Bekinschtein TA. 2013. Expectation and Attention in Hierarchical Auditory Prediction. Journal of Neuroscience 33:11194-11205. DOI: https://doi.org/10.1523/JNEUROSCI.0114-13.2013.
Cherry, E.C., 1953. Some experiments on the recognition of speech, with one and with two ears. J. Acoust. Soc. Am. 25 (5), 975-979.
Cheung VKM, Harrison PMC, Meyer L, Pearce MT, Haynes J-D, Koelsch S. 2019. Uncertainty and surprise jointly predict musical pleasure and Amygdala, Hippocampus, and auditory cortex activity. Current Biology 29:4084-4092. DOI: https://doi.org/10.1016/j.cub.2019.09.067.
Chi T, Gao Y, Guyton MC, Ru P, Shamma S. 1999. Spectrotemporal modulation transfer functions and speech intelligibility. The Journal of the Acoustical Society of America 106:2719-2732. DOI: https://doi.org/10.1121/1.428100, PMID: 10573888.
Chi, T., Ru, P., and Shamma, S.A. (2005). Multiresolution spectrotemporal analysis of complex sounds. J. Acoust. Soc. Am. 118, 887-906.
Christianson GB, Sahani M, Linden JF. 2008. The consequences of response nonlinearities for interpretation of spectrotemporal receptive fields. Journal of Neuroscience 28:446-455. DOI: https://doi.org/10.1523/JNEUROSCI.1775-07.2007, PMID: 18184787.
Christoph Boeddeker, Hakan Erdogan, Takuya Yoshioka, and Reinhold Haeb-Umbach, "Exploring practical aspects of heural mask-based beamforming for far-field speech recognition," in 2018 IEEE International Conference on Acoustics, Speech and Signal Processing (ICASSP). IEEE, 2018, pp. 6697-6701.
Christoph Boeddeker, Patrick Hanebrink, Lukas Drude, Jahn Heymann, and Reinhold Haeb-Umbach, "Optimizing neuralnetwork supported acoustic beamforming by algorithmic differentiation," in Acoustics, Speech and Signal Processing (ICASSP), 2017 IEEE International Conference on. IEEE,2017, pp. 171-175.
Clark A. 2013. Whatever next? Predictive brains, situated agents, and the future of cognitive science. Behavioral and Brain Sciences 36:181-204. DOI: https://doi.org/10.1017/S0140525X12000477.
Clark, J.L., Swanepoel, D.W., 2014. Technology for hearing loss—as we know it, and as we dream it . . . Disability and rehabilitation. Assistive technology 9 5 . 408-13.
Clarke, S., and Morosan, P. (2012). Architecture, connectivity, and transmitter receptors of human auditory cortex. In The Human Auditory Cortex, D. Poeppel, T. Overath, A.N. Popper, and R.R. Fay, eds. (Springer), pp. 11-38.
Coates A, Ay N. 2011. Selecting receptive fields in deep networks. Advances in Neural Information Processing Systems 2528-2536.
Coffey EBJ, Musacchia G, Zatorre RJ. 2017. Cortical Correlates of the Auditory Frequency-Following and Onset Responses: EEG and fMRI Evidence. The Journal of Neuroscience 37:830-838. DOI: https://doi.org/10.1523/JNEUROSCI.1265-16.2016.
Cogan, G.B., Thesen, T., Carlson, C., Doyle, W., Devinsky, O., and Pesaran, B. (2014). Sensory-motor transformations for speech occur bilaterally. Nature 507, 94-98.
Conway, C. M., Bauernschmidt, A., Huang, S. S. & Pisoni, D. B. Implicit statistical learning in language processing: Word predictability is the key. Cognition 114, 356-371 (2010).
Coulson, S. & Kutas, M. Getting it: Human event-related brain response to jokes in good and poor comprehenders. Neurosci. Lett. 316, 71-74 (2001).
Cox, M.A.A., and Cox, T.F. (2008). Multidimensional scaling. In Handbook of Data Visualization, (Springer), pp. 315-347.
Crone NE, Boatman D, Gordon B, Hao L. 2001. Induced electrocorticographic gamma activity during auditory perception. Brazier Award-winning article, 2001. Clinical Neurophysiology 112:565-582. DOI: https://doi.org/10.1016/s1388-2457(00)00545-9, PMID: 11275528.
Crosse, M. J., Butler, J. S. & Lalor, E. C. Congruent visual speech enhances cortical entrainment to continuous auditory speech in noise-free conditions. J. Neurosci. 35, 14195-1420 (2015).
Crosse, M. J., Di Liberto, G. M., Bednar, A. & Lalor, E. C. The multivariate temporal response function (mTRF) toolbox: A MATLAB toolbox for relating neural signals to continuous stimuli. Front. Hum. Neurosci. 10, (2016).
Cuddy LL, Lunney CA. 1995. Expectancies generated by melodic intervals: perceptual judgments of melodic continuity. Perception & Psychophysics 57:451-462. DOI: https://doi.org/10.3758/BF03213071, PMID: 7596743.
D. Kingma and J. Ba, "Adam: A method for stochastic optimization," arXiv preprint arXiv:1412.6980, 2014.
D. Stoller, S. Ewert, and S. Dixon, "Wave-u-net: A multi-scale neural network for end-to-end audio source separation," arXiv preprint arXiv:1806.03185, 2018.
D. Yu, M. Kolbk, Z. Tan, and J. Jensen, "Permutation invariant training of deep models for speaker-independent multi-talker speech separation," in 2017 IEEE International Conference on Acoustics, Speech and Signal Processing (ICASSP), Mar. 2017, pp. 241-245.
Da Costa, S., van der Zwaag, W., Marques, J.P., Frackowiak, R.S.J., Clarke, S., and Saenz, M. "Human Primary Auditory Cortex Follows the Shape of Heschl's Gyrus". The Journal of NeuroScience, 31(40):14067-14075 (2011).
Das N, Biesmans W, Bertrand A, Francart T. 2016. The effect of head-related filtering and ear-specific decoding Bias on auditory attention detection. Journal of Neural Engineering 13:056014. DOI: https://doi.org/10.1088/1741-2560/13/5/056014, PMID: 27618842.
Daube, C., Ince, R. A. A. & Gross, J. Simple Acoustic Features Can Explain Phoneme-Based Predictions of Cortical Responses to Speech. Curr. Biol. 29, 1924-1937 e9 (2019).
David Diaz-Guerra, Antonio Miguel, and Jose R Beltran, "gpurir: A python library for room impulse response simulation with gpu acceleration," arXiv preprint arXiv:1810.11359, 2018.
David SV, Gallant JL. 2005. Predicting neuronal responses during natural vision. Network: Computation in Neural Systems 16:239-260. DOI: https://doi.org/10.1080/09548980500464030.
David SV, Mesgarani N, Fritz JB, Shamma SA. 2009. Rapid synaptic depression explains nonlinear modulation of spectrotemporal tuning in primary auditory cortex by natural stimuli. Journal of Neuroscience 29:3374-3386. DOI: https://doi.org/10.1523/JNEUROSCI.5249-08.2009, PMID: 19295144.
David SV, Shamma SA. 2013. Integration over multiple timescales in primary auditory cortex. Journal of Neuroscience 33:19154-19166. DOI: https://doi.org/10.1523/JNEUROSCI.2270-13.2013, PMID: 24305812.
David, S.V., Fritz, J.B., and Shamma, S.A. (2012). Task reward structure shapes rapid receptive field plasticity in auditory cortex. Proc. Natl. Acad. Sci. USA 109, 2144-2149.
De Cheveigné, A., Wong, D.D., Di Liberto, G.M., Hjortkjaer, J., Slaney, M., Lalor, E., 2018. Decoding the auditory brain with canonical component analysis. Neuroimage 172, 206-216.
De Heer, W. A., Huth, A. G., Griffiths, T. L., Gallant, J. L. & Theunissen, F. E. The hierarchical cortical organization of human speech processing. J. Neurosci. 37, 6539-6557 (2017).
De Heer, W.A., Huth, A.G., Griffiths, T.L., Gallant, J.L., and Theunissen, F.E. (2017). The Hierarchical Cortical Organization of Human Speech Processing. J. Neurosci. 37, 6539-6557.
De Martino, F., Moerel, M., Xu, J., van de Moortele, P.F., Ugurbil, K., Goebel, R., Yacoub, E., and Formisano, E. (2015). High-resolution mapping of myeloarchitecture in vivo: Localization of auditory areas in the human brain. Cereb. Cortex 25, 3394-3405.
Dean I, Harper NS, McAlpine D. 2005. Neural population coding of sound level adapts to stimulus statistics. Nature Neuroscience 8:1684-1689. DOI: https://doi.org/10.1038/nn1541, PMID: 16286934.
Dean I, Robinson BL, Harper NS, McAlpine D. 2008. Rapid neural adaptation to sound level statistics. Journal of Neuroscience 28:6430-6438. DOI: https://doi.org/10.1523/JNEUROSCI.0470-08.2008, PMID: 18562614.
DeJesus, J. M., Hwang, H. G., Dautel, J. B. & Kinzler, K. D. Bilingual children's social preferences hinge on accent. J. Exp. Child Psychol. 164, 178-191 (2017).
Destrieux, C., Fischl, B., Dale, A., and Halgren, E. (2010). Automatic parcellation of human cortical gyri and sulci using standard anatomical nomenclature. Neuroimage 53, 1-15.

(56) References Cited

OTHER PUBLICATIONS

DeWitt, I., and Rauschecker, J.P. (2012). Phoneme and word recognition in the auditory ventral stream. Proc. Natl. Acad. Sci. 109, E505-E514.

Di Liberto GM, Pelofi C, Shamma S, de Cheveigne' A. 2020. Musical expertise enhances the cortical tracking of the acoustic envelope during naturalistic music listening. Acoustical Science and Technology 41:361-364. DOI: https://doi.org/10.1250/ast.41.361.

Di Liberto, G. M. & Lalor, E. C. Indexing cortical entrainment to natural speech at the phonemic level: Methodological considerations for applied research. Hear. Res. 348, 70-77 (2017).

Di Liberto, G. M. et al. Atypical cortical entrainment to speech in the right hemisphere underpins phonemic deficits in dyslexia. Neuroimage NIMG-17-29, 70-79 (2018).

Di Liberto, G. M., Pelofi, C., Bianco, R., Patel, P., Mehta, A. D., Herrero, J. L., de Cheveigné, A., Shamma, S., Mesgarani, N. (2019). Cortical encoding of melodic expectations in human temporal cortex. eLife, 135-160. https://doi.org/10.1101/714634.

Di Liberto, G. M., Wong, D., Melnik, G. A. & de Cheveigne, A. Low-frequency cortical responses to natural speech reflect probabilistic phonotactics. Neuroimage 196, 237-247 (2019).

Di Liberto, G.M., O'Sullivan, J.A., and Lalor, E.C. (2015). Low-Frequency Cortical Entrainment to Speech Reflects Phoneme-Level Processing. Curr. Biol. 25, 2457-2465.

Di Liberto, Giovanni M., et al., "Neural representation of linguistic feature hierarchy reflects second-language proficiency," (2020) 44-70.

Dick, F., Tierney, A.T., Lutti, A., Josephs, O., Sereno, M.I., and Weiskopf, N. (2012). In vivo functional and myeloarchitectonic mapping of human primary auditory areas. J. Neurosci. 32, 16095-16105.

Dijkstra, K. , Brunner, P. , Gunduz, A. , Coon, W.G. , Ritaccio, A. L. , Farquhar, J. , Schalk, G. , 2015. Identifying the attended speaker using electrocorticographic (ecog) signals . . . Brain computer interfaces 2 4, 161-173.

Ding N, Simon JZ. 2012a. Neural coding of continuous speech in auditory cortex during monaural and dichotic listening. Journal of Neurophysiology 107:78-89. DOI: https://doi.org/10.1152/jn.00297. 2011, PMID: 21975452.

Ding N, Simon JZ. 2012b. Emergence of neural encoding of auditory objects while listening to competing speakers. PNAS 109:11854-11859. DOI: https://doi.org/10.1073/pnas.1205381109, PMID: 22753470.

Ding, N., and Simon, J.Z. (2012). Emergence of neural encoding of auditory objects while listening to competing speakers. Proc. Natl. Acad. Sci. USA 109, 11854-11859.

Ding, N., Chatterjee, M. & Simon, J. Z. Robust cortical entrainment to the speech envelope relies on the spectro-temporal fine structure. Neuroimage 88, 41-46 (2014).

Doclo, S. , Kellermann, W. , Makino, S. , Nordholm, S. , 2015. Multichannel signal enhance-ment algorithms for assisted listening devices: exploiting spatial diversity using mul-tiple microphones. IEEE Signal Process. Mag. 32, 18-30.

Dorsaint-Pierre, R., Penhune, V.B., Watkins, K.E., Neelin, P., Lerch, J.P., Bouffard, M., and Zatorre, R.J. (2006). Asymmetries of the planum temporale and Heschl's gyrus: relationship to language lateralization. Brain 129, 1164-1176.

Doving KB. 1966. An electrophysiological study of odour similarities of homologous substances. The Journal of Physiology 186:97-109. DOI: https://doi.org/10.1113/jphysiol.1966.sp008022, PMID: 5914260.

Dunsby J. 2014. On repeat: how music plays the mind. By Elizabeth Hellmuth Margulis. Music and Letters 95: 497-499. DOI: https://doi.org/10.1093/ml/gcu055.

Dykstra, A.R., Chan, A.M., Quinn, B.T., Zepeda, R., Keller, C.J., Cormier, J., Madsen, J.R., Eskandar, E.N., and Cash, S.S. (2012). Individualized localization and cortical surface-based registration of intracranial electrodes. Neuroimage 59, 3563-3570.

E. Hadad, D. Marquardt, S. Doclo, and S. Gannot, "Theoretical analysis of binaural transfer function mvdr beamformers with interference cue preservation constraints," IEEE/ACM Transactions on Audio, Speech, and Language Processing, vol. 23, No. 12, pp. 2449-2464, 2015.

Edwards E, Soltani M, Kim W, Dalal SS, Nagarajan SS, Berger MS, Knight RT. 2009. Comparison of time-frequency responses and the event-related potential to auditory speech stimuli in human cortex. Journal of Neurophysiology 102:377-386. DOI: https://doi.org/10.1152/jn.90954.2008, PMID: 19439673.

Eerola T, Louhivuori J, Lebaka E. 2009. Expectancy in Sami Yoiks revisited: the role of data-driven and schema-driven knowledge in the formation of melodic expectations. Musicae Scientiae 13:231-272. DOI: https://doi.org/10.1177/102986490901300203.

Eerola T. 2003. The Dynamics of Musical Expectancy Cross-Cultural and Statistical Approaches to Melodic Expectations. University of Jyvaskyla.

Einhom R. Hearing aid technology for the 21st century: A proposal for universal wireless connectivity and improved sound quality <https://pubmed.ncbi.nlm.nih.gov/28328494/>. IEEE Pulse. Mar.-Apr. 2017; 8(2): pp. 25-28.

Elhilali, M., Xiang, J., Shamma, S.A., and Simon, J.Z. (2009). Interaction between attention and bottom-up saliency mediates the representation of foreground and background in an auditory scene. PLoS Biol. 7, e1000129.

Emad M Grais, Dominic Ward, and Mark D Plumbley, "Raw multi-channel audio source separation using multiresolution convolutional auto-encoders," arXiv preprint arXiv:1803.00702, 2018.

Ennes Sarradj, "A fast signal subspace approach for the determination of absolute levels from phased microphone array measurements," Journal of Sound and Vibration, vol. 329, No. 9, pp. 1553-1569, 2010.

Ephrat, A. , Mosseri, I. , Lang, O. , Dekel, T. , Wilson, K. , Hassidim, A. , Freeman, W.T. , Rubinstein, M. , 2018. Looking to listen at the cocktail party: a speaker-independent audio-visual model for speech separation. ACM Trans. Graph. 37, 112:1-112:11.

Erickson LC, Thiessen ED. 2015. Statistical learning of language: theory, validity, and predictions of a statistical learning account of language acquisition. Developmental Review 37:66-108. DOI: https://doi.org/10.1016/j.dr.2015.05.002.

Ernst Warsitz and Reinhold Haeb-Umbach, "Blind acoustic beamforming based on generalized eigenvalue decomposition," IEEE Transactions on audio, speech, and language processing, vol. 15, No. 5, pp. 1529-1539, 2007.

Evans, S. & Davis, M. H. Hierarchical organization of auditory and motor representations in speech perception: Evidence from searchlight similarity analysis. Cereb. Cortex 25, 4772-4788 (2015).

F. Grondin and J. Glass, "Multiple sound source localization with svd-phat," Interspeech 2019, pp. 2698-2702, 2019.

Federmeier, K. D. Thinking ahead: The role and roots of prediction in language comprehension. Psychophysiology 44, 491-505 (2007).

Fedorenko, E., Scott, T.L., Brunner, P., Coon, W.G., Pritchett, B., Schalk, G., and Kanwisher, N. (2016). Neural correlate of the construction of sentence meaning. Proc. Natl. Acad. Sci. USA 113, E6256-E6262.

Finn AS, Lee T, Kraus A, Hudson Kam CL. 2014. When It Hurts (and Helps) to Try: The Role of Effort in Language earning. PLOS ONE 9:e101806. DOI: https://doi.org/10.1371/journal.pone. 0101806.

Fischl, B., Sereno, M.I., and Dale, A.M. (1999). Cortical surface-based analysis. II: Inflation, flattening, and a surface-based coordinate system. Neuroimage 9, 195-207.

Fischl, B., Van Der Kouwe, A., Destrieux, C., Halgren, E., Ségonne, F., Salat, D.H., Busa, E., Seidman, L.J., Goldstein, J., and Kennedy, D. (2004). Automatically parcellating the human cerebral cortex. Cereb. Cortex 14, 11-22.

Fishman YI. 2014. The mechanisms and meaning of the mismatch negativity. Brain Topography 27:500-526. DOI: https://doi.org/10.1007/s10548-013-0337-3.

Borgström, Bengt J., et al., "Speaker seperation in realistic noise environments with applications to a cognitively-controlled hearing aid," Neural Networks, 140 (2021): 136-147.

(56) References Cited

OTHER PUBLICATIONS

Fiedler, L., Wöstmann, M., Graversen, C., Brandmeyer, A., Lunner, T., & Obleser, J. (2017). Single-channel in-ear-EEG detects the focus of auditory attention to concurrent tone streams and mixed speech. Journal of neural engineering, 14(3), 036020.
Das, N., Van Eyndhoven, S., Francart, T., & Bertrand, A. (2016). Adaptive attention-driven speech enhancement for EEG-informed hearing prostheses. Annual International Conference of the IEEE Engineering in Medicine and Biology Society. IEEE Engineering in Medicine and Biology Society. Annual International Conference, 2016, 77-80.
Lin, B. S., Liu, C. F., Cheng, C. J., Wang, J. J., Liu, C., Li, J., & Lin, B. S. (2019). Development of Novel Hearing Aids by Using Image Recognition Technology. IEEE journal of biomedical and health informatics, 23(3), 1163-1170.
Kappel, S. L., Rank, M. L., Toft, H. O., Andersen, M., & Kidmose, P. (2019). Dry-Contact Electrode Ear-EEG. IEEE transactions on bio-medical engineering, 66(1), 150-158.
Kuruvila, I., Fischer, E., & Hoppe, U. (2020). An LMMSE-based Estimation of Temporal Response Function in Auditory Attention Decoding. Annual International Conference of the IEEE Engineering in Medicine and Biology Society. IEEE Engineering in Medicine and Biology Society. Annual International Conference, 2020, 2837-2840.
Geirnaert, Simon & Vandecappelle, Servaas & Alickovic, Emina & Cheveigné, Alain & Lalor, Edmund & Meyer, Bernd & Miran, Sina & Francart, Tom & Bertrand, Alexander. (2020). Neuro-Steered Hearing Devices: Decoding Auditory Attention From the Brain (20 pages).
Abbott LF. 1997. Synaptic depression and cortical gain control. Science 275:221-224. DOI: https://doi.org/10.1126/science.275.5297.221.
Adam Santoro, David Raposo, David G. Barrett, Mateusz Malinowski, Razvan Pascanu, Peter Battaglia, and Timothy Lillicrap, "A simple neural network module for relational reasoning," in Advances in neural information processing systems, 2017, pp. 4967-4976.
Aertsen AMHJ, Johannesma PIM. 1981. The Spectro-Temporal receptive field. Biological Cybernetics 42:133-143. DOI: https://doi.org/10.1007/BF00336731.
Ahissar, E. et al. Speech Comprehension is Correlated with Temporal Response Patterns Recorded from Auditory Cortex. Proc Natl Acad Sci U S A 98, 13367-13372 (2001).
Ahrens MB, Paninski L, Sahani M. 2008. Inferring input nonlinearities in neural encoding models. Network: Computation in Neural Systems 19:35-67. DOI: https://doi.org/10.1080/09548980701813936.
Akbari, H., Khalighinejad, B., Herrero, J.L., Mehta, A.D., Mesgarani, N., 2019. Towards reconstructing intelligible speech from the human auditory cortex. Sci. Rep. 9 (1), 874.
Alain, C., Shen, D., Yu, H. & Grady, C. Dissociable memory- and response-related activity in parietal cortex during auditory spatial working memory. Front. Psychol. 1, (2010).
Albouy, P., Benjamin, L., Morillon, B., and Zatorre, R.J. (2020). Distinct sensitivity to spectrotemporal modulation supports brain asymmetry for speech and melody. Science (80-. ). 367, 1043-1047.
Aroudi, A., Doclo, S., 2019. Cognitive-driven binaural Icmv beamformer using eeg-based auditory attention decoding. In: ICASSP 2019—2019 IEEE International Conference on Acoustics, Speech and Signal Processing (ICASSP), pp. 406-410.
Atiani, S., David, S.V., Elgueda, D., Locastro, M., Radtke-Schuller, S., Shamma, S.A., and Fritz, J.B. (2014). Emergent selectivity for task-relevant stimuli in higher-order auditory cortex. Neuron 82, 486-499.
Atiani, S., Elhilali, M., David, S.V., Fritz, J.B., and Shamma, S.A. (2009). Task difficulty and performance induce diverse adaptive patterns in gain and shape of primary auditory cortical receptive fields. Neuron 61, 467-480.
Attaheri A, Kikuchi Y, Milne AE, Wilson B, Alter K, Petkov CI. 2015. EEG potentials associated with artificial grammar learning in the primate brain. Brain and Language 148:74-80. DOI: https://doi.org/10.1016/j.bandl.2014.11.006, PMID: 25529405.
Auksztulewicz R, Friston K. 2016. Repetition suppression and its contextual determinants in predictive coding. Cortex 80:125-140. DOI: https://doi.org/10.1016/j.cortex.2015.11.024, PMID: 26861557.
Bar M, Kassam KS, Ghuman AS, Boshyan J, Schmid AM, Schmidt AM, Dale AM, Hamalainen MS, Marinkovic K, Schacter DL, Rosen BR, Halgren E. 2006. Top-down facilitation of visual recognition. PNAS 103:449-454. DOI: https://doi.org/10.1073/pnas.0507062103, PMID: 16407167.
Barfuss, H., Mueglich, M., Kellermann, W., 2016. HRTF-based robust least-squares fre-quency-invariant polynomial beamforming. In: 2016 IEEE International Workshop on Acoustic Signal Enhancement (IWAENC), pp. 1-5.
Baroni, M., Dinu, G. & Kruszewski, G. Don't count, predict! A systematic comparison of context-counting vs. context-predicting semantic vectors. in 52nd Annual Meeting of the Association for Computational Linguistics, ACL 2014—Proceedings of the Conference 1, 238-247 (Association for Computational Linguistics (ACL), 2014).
Barton, B., Venezia, J.H., Saberi, K., Hickok, G., and Brewer, A.A. (2012). Orthogonal acoustic dimensions define auditory field maps in human cortex. Proc. Natl. Acad. Sci. 109, 20738-20743.
Batty E, Merel J, Brackbill N, Heitman A, Sher A, Litke A. 2016. Multilayer recurrent network models of primate retinal ganglion cell responses. ICLR 2017 Conference Submission.
Bednar, A. & Lalor, E. C. Where is the cocktail party? Decoding locations of attended and unattended moving sound sources using EEG. Neuroimage 205, (2020).
Belin, P., Zatorre, R.J., Lafaille, P., Ahad, P., and Pike, B. (2000). Voice-selective areas in human auditory cortex. Nature 403, 309-312.
Benjamini, Y., and Yekutieli, D. (2001). The control of the false discovery rate in multiple testing under dependency (JSTOR).
Berezutskaya J, Freudenburg ZV, Guclu U, van Gerven MAJ, Ramsey NF. 2017. Neural tuning to Low-Level features of speech throughout the perisylvian cortex. The Journal of Neuroscience 37:7906-7920. DOI: https://doi.org/10.1523/JNEUROSCI.0238-17.2017, PMID: 28716965.
Besson M, Macar F. 1987. An event-related potential analysis of incongruity in music and other non-linguistic contexts. Psychophysiology 24:14-25. DOI: https://doi.org/10.1111/j.1469-8986.1987_tb01853.x, PMID: 35755 90.
Best, C. T. & Tyler, M. D. Nonnative and second-language speech perception: Commonalities and complementarities. In Language experience in second language speech learning: In honor of James Emil Flege 13-34 (2007).
Bialystok, E. & Hakuta, K. Confounded Age: Linguistic and Cognitive Factors in Age Differences for Second Language Acquisition. Lawrence Erlbaum Assoc. Publ. 161-181 (1999). doi:10.1017/S0272263101333053.
Bianco R, Novembre G, Keller PE, Kim SG, Scharf F, Friederici AD, Villringer A, Sammler D. 2016. Neural networks for harmonic structure in music perception and action. NeuroImage 142:454-464. DOI: https://doi.org/10.1016/j.neuroimage.2016.08.025, PMID: 27542722.
Bianco R, Ptasczynski LE, Omigie D. 2020. Pupil responses to pitch deviants reflect predictability of melodic sequences. Brain and Cognition 138:103621. DOI: https://doi.org/10.1016/j.bandc.2019.103621, PMID: 31862512.
Bidelman, G.M., Moreno, S., and Alain, C. (2013). Tracing the emergence of categorical speech perception in the human auditory system. Neuroimage 79, 201-212.
Bigand E, Poulin-Charronnat B. 2006. Are we "experienced listeners"? A review of the musical capacities that do not depend on formal musical training. Cognition 100:100-130. DOI: https://doi.org/10.1016/j.cognition.2005.11.007.
Bizley, J.K., and Cohen, Y.E. (2013). The what, where and how of auditory-object perception. Nat. Rev. Neurosci. 14, 693-707.
Bizley, J.K., Walker, K.M.M., Nodal, F.R., King, A.J., and Schnupp, J.W.H. (2013). Auditory cortex represents both bitch judgments and the corresponding acoustic cues. Curr. Biol. 23, 620-625.
Bizley, J.K., Walker, K.M.M., Silverman, B.W., King, A.J., and Schnupp, J.W.H. (2009). Interdependent encoding of pitch, timbre, and spatial location in auditory cortex. J. Neurosci. 29, 2064-2075.

(56) References Cited

OTHER PUBLICATIONS

Bo Li, Tara N Sainath, Ron J Weiss, Kevin W Wilson, and Michiel Bacchiani, "Neural network adaptive beamforming for robust multichannel speech recognition.," in Proc. Interspeech, 2016, pp. 1976-1980.
Boersma, P. (2006). Praat: doing phonetics by computer. Http//Www. Praat. Org/.
Bohn, O.-S. & Munro, M. J. Language experience in second language speech learning : in honor of James Emil Flege. Language learning and language teaching, (2007).
Bolt, R. H. et al. Identification of a Speaker by Speech Spectrograms. Science (80-. ). 166, 338-342 (1969).
Borovsky, A., Elman, J. L. & Kutas, M. Once is Enough: N400 Indexes Semantic Integration of Novel Word Meanings from a Single Exposure in Context. Lang. Learn. Dev. 8, 278-302 (2012).
Bouchard, K.E.K.E., Mesgarani, N., Johnson, K., and Chang, E.F. E.F. (2013). Functional organization of human sensorimotor cortex for speech articulation. Nature 495, 327-332.
Boudreau JC. 1974. Neural encoding in cat geniculate ganglion tongue units. Chemical Senses 1:41-51. DOI: https://doi.org/10.1093/chemse/1.1.41.
Bozic, M., Tyler, L.K., Ives, D.T., Randall, B., and Marslen-Wilson, W.D. (2010). Bihemispheric foundations for human speech comprehension. Proc. Natl. Acad. Sci. 107, 17439-17444.
Brandmeyer, A., Farquhar, J. D. R., McQueen, J. M. & Desain, P. W. M. Decoding Speech Perception by Native and Non-Native Speakers Using Single-Trial Electrophysiological Data. PLoS One 8, (2013).
Braun, S. , Neil, D. , Liu, S.-C. , 2017. A curriculum learning method for improved noise robustness in automatic speech recognition. In: 2017 25th European Signal Processing Conference (EUSIPCO). IEEE, pp. 548-552 .
Bregman, A.S. , Pinker, S. , 1978. Auditory streaming and the building of timbre . . . Canadian Journal of Psychology/ Revue canadienne de psychologie 32 (1), 19.
Brenner N, Strong SP, Koberle R, Bialek W, de Ruyter van Steveninck RR. 2000. Synergy in a neural code. Neural Computation 12:1531-1552. DOI: https://doi.org/10.1162/089976600300015259, PMID: 10935917.
Bretan M, Oore S, Eck D, Heck L. 2017. Learning and evaluating musical features with deep autoencoders. arXiv. https://arxiv.org/abs/1706.04486.
Brewer, A.A., and Barton, B. (2016). Maps of the auditory cortex. Annu. Rev. Neurosci. 39, 385-407.
Brodbeck C, Hong LE, Simon JZ. 2018a. Rapid Transformation from Auditory to Linguistic Representations of Continuous Speech. Current Biology 28:3976-3983. DOI: https://doi.org/10.1016/j.cub.2018.10.042.
Brodbeck C, Hong LE, Simon JZ. 2018c. Transformation from auditory to linguistic representations across auditory cortex is rapid and attention dependent for continuous speech. bioRxiv. DOI: https://doi.org/10.1101/326785.
Brodbeck C, Presacco A, Simon JZ. 2018b. Neural source dynamics of brain responses to continuous stimuli: Speech processing from acoustics to comprehension. NeuroImage 172:162-174. DOI: https://doi.org/10.1016/j.neuroimage.2018.01.042.
Brodbeck, C., Presacco, A., Anderson, S. & Simon, J. Z. Overrepresentation of speech in older adults originates from early response in higher order auditory cortex. in Acta Acustica united with Acustica 104, 774-777 (S. Hirzel Verlag GmbH, 2018).
Yi Luo, Zhuo Chen, and Nima Mesgarani, "Speakerindependent speech separation with deep attractor network," IEEE/ACM Transactions on Audio, Speech, and Language Processing, vol. 26, No. 4, pp. 787-796, 2018.
Yokoyama, S. et al. Cortical activation in the processing of passive sentences in L1 and L2: An fMRI study. Neuroimage 30, 570-579 (2006).
Yuan, J., and Liberman, M. (2008). Speaker identification on the SCOTUS corpus. J. Acoust. Soc. Am. 123, 3878.

Yutaro Matsui, Tomohiro Nakatani, Marc Delcroix, Keisuke Kinoshita, Nobutaka Ito, Shoko Araki, and Shoji Makino, "Online integration of dnn-based and spatial clustering-based mask estimation for robust mvdr beamforming," in 2018 16th International Workshop on Acoustic Signal Enhancement (IWAENC). IEEE, 2018, pp. 71-75.
Z. Chen, Y. Luo, and N. Mesgarani, "Deep attractor network for single-microphone speaker separation," in Acoustics, Speech and Signal Processing (ICASSP), 2017 IEEE International Conference on. IEEE, 2017, pp. 246-250.
Z.-Q. Wang, J. Le Roux, and J. R. Hershey, "Alternative objective functions for deep clustering," in Acoustics, Speech and Signal Processing (ICASSP), 2018 IEEE International Conference on, 2018.
Zatorre RJ, Salimpoor VN. 2013. From perception to pleasure: music and its neural substrates. PNAS 110: 10430-10437. DOI: https://doi.org/10.1073/pnas.1301228110, PMID: 23754373.
Zatorre, R.J., and Penhune, V.B. (2001). Spatial localization after excision of human auditory cortex. J.Neurosci. 21, 6321-6328.
Zhang, Y., Kuhl, P. K., Imada, T., Kotani, M. & Tohkura, Y. Effects of language experience: Neural commitment to language-specific auditory patterns. Neuroimage 26, 703-720 (2005).
Zhao, L., Benesty, J., Chen, J., 2014. Design of robust differential microphone arrays. IEEE/ACM Trans. Audio Speech Lang. Process. 22, 1455-1466.
Zhong Meng, Shinji Watanabe, John R. Hershey, and Hakan Erdogan, "Deep long short-term memory adaptive beamforming networks for multichannel robust speech recognition," in Acoustics, Speech and Signal Processing (ICASSP), 2017 IEEE International Conference on. IEEE, 2017, pp. 271-275.
Zinszer, B. D., Chen, P., Wu, H., Shu, H. & Li, P. Second language experience modulates neural specialization for first language lexical tones. J. Neurolinguistics 33, 50-66 (2015).
Zion Golumbic, E.M., Ding, N., Bickel, S., Lakatos, P., Schevon, C.A., McKhann, G.M., Goodman, R.R., Emerson, R., Mehta, A.D., Simon, J.Z., et al. (2013). Mechanisms underlying selective neuronal tracking of attended speech at a "cocktail party". Neuron 77, 980-991.
Phillips, C., Pellathy, T., Marantz, A., Yellin, E., Wexler, K., Poeppel, D., McGinnis, M., and Roberts, T. (2000). Auditory cortex accesses phonological categories: an MEG mismatch study. Cogn. Neurosci. J. 12, 1038-1055.
Pearce MT. 2018. Statistical learning and probabilistic prediction in music cognition: mechanisms of stylistic enculturation. Annals of the New York Academy of Sciences 1423:378-395. DOI: https://doi.org/10.1111/nyas.13654.
Peelle, J.E., Wingfield, A., 2016. The neural consequences of age-related hearing loss. Trends Neurosci. 39, 486-497.
Perani, D. & Abutalebi, J. The neural basis of first and second language processing. Current Opinion in Neurobiology 15, 202-206 (2005).
Petkov, C.I., Kang, X., Alho, K., Bertrand, O., Yund, E.W., and Woods, D.L. (2004). Attentional modulation of human auditory cortex. Nat. Neurosci. 7, 658-663.
Pinto N, Doukhan D, DiCarlo JJ, Cox DD. 2009. A high-throughput screening approach to discovering good forms of biologically inspired visual representation. PLOS Computational Biology 5:e1000579. DOI: https://doi.org/10.1371/journal.pcbi.1000579, PMID: 19956750.
Power, A.J., Foxe, J.J., Forde, E.J., Reilly, R.B., and Lalor, E.C. (2012). At what time is the cocktail party? A late locus of selective attention to natural speech. Eur. J. Neurosci. 35, 1497-1503.
Presacco, A., Simon, J. Z. & Anderson, S. Speech-in-noise representation in the aging midbrain and cortex: Effects of hearing loss. PLoS One 14, e0213899 (2019).
Puschmann, S., Baillet, S., and Zatorre, R.J. (2018). Musicians at the cocktail party: neural substrates of musical training during selective listening in multispeaker situations. Cereb. Cortex.
Puvvada, K.C., and Simon, J.Z. (2017). Cortical Representations of Speech in a Multi-talker Auditory Scene. J. Neurosci. 37, 0938-17.

(56) References Cited

OTHER PUBLICATIONS

Q. Liu, Y. Xu, P. J. Jackson, W. Wang, and P. Coleman, "Iterative deep neural networks for speaker-independent binaural blind speech separation," in 2018 IEEE International Conference on Acoustics, Speech and Signal Processing (ICASSP). IEEE, 2018, pp. 541-545.

Qi Z, Beach SD, Finn AS, Minas J, Goetz C, Chan B, Gabrieli JDE. 2017. Native-language N400 and P600 predict dissociable language-learning abilities in adults. Neuropsychologia 98:177-191. DOI: https://doi.org/10.1016/j.neuropsychologia.2016.10.005, PMID: 27737775.

Quiroga-Martinez DR, Hansen NC, Højlund A, Pearce M, Brattico E, Vuust P. 2019b. Decomposing neural responses to melodic surprise in musicians and non-musicians: evidence for a hierarchy of predictions in the auditory system. bioRxiv. DOI: https://doi.org/10.1101/786574.

Quiroga-Martinez DR, Hansen NC, Højlund A, Pearce MT, Brattico E, Vuust P. 2019a. Reduced prediction error responses in high-as compared to low-uncertainty musical contexts. Cortex 120:181-200. DOI: https://doi.org/10.1016/i.cortex.2019.06.010, PMID: 31323458.

R. Gu, J. Wu, S.-X. Zhang, L. Chen, Y. Xu, M. Yu, D. Su, Y. Zou, and D. Yu, "End-to-end multi-channel speech separation," arXiv preprint arXiv:1905.06286, 2019.

Rabinowitz NC, Willmore BD, Schnupp JW, King AJ. 2011. Contrast gain control in auditory cortex. Neuron 70: 1178-1191. DOI: https://doi.org/10.1016/j.neuron.2011.04.030, PMID: 21689603.

Rademacher, J., Caviness, V.S., Jr., Steinmetz, H., and Galaburda, A.M. (1993). Topographical variation of the human primary cortices: implications for neuroimaging, brain mapping, and neurobiology. Cereb. Cortex 3, 313-329.

Rademacher, J., Morosan, P., Schormann, T., Schleicher, A., Werner, C., Freund, H.-J., and Zilles, K.(2001). Probabilistic mapping and volume measurement of human primary auditory cortex. Neuroimage 13, 669-683.

Rasmussen, G.L. (1964). Anatomic relationships of the ascending and descending auditory systems. Neurol. Asp. Audit. Vestib. Disord. 1, 5-19.

Rauschecker, J.P. (1997). Processing of complex sounds in the auditory cortex of cat, monkey, and man. Acta Otolaryngol. Suppl. 532, 34-38.

Rauschecker, J.P., and Scott, S.K. (2009). Maps and streams in the auditory cortex: nonhuman primates illuminate human speech processing. Nat. Neurosci. 12, 718-724.

Ray S, Crone NE, Niebur E, Franaszczuk PJ, Hsiao SS. 2008. Neural correlates of high-gamma oscillations (60-200hz) in macaque local field potentials and their potential implications in electrocorticography. Journal of Neuroscience 28:11526-11536. DOI: https://doi.org/10.1523/JNEUROSCI.2848-08.2008, PMID: 18987189.

Ray, S., and Maunsell, J.H.R. (2011). Different Origins of Gamma Rhythm and High-Gamma Activity in Macaque Visual Cortex. PLoS Biol. 9.

Reindl, K., Meier, S., Barfuss, H., Kellermann, W. , 2014. Minimum mutual information based linearly constrained broadband signal extraction. IEEE/ACM Trans. Audio Speech Lang. Process. 22, 1096-1108.

Reiterer, S., Pereda, E. & Bhattacharya, J. Measuring second language proficiency with EEG synchronization: how functional cortical networks and hemispheric involvement differ as a function of proficiency level in second language speakers. Second Lang. Res. 25, 77-106 (2009).

Reiterer, S., Pereda, E. & Bhattacharya, J. On a possible relationship between linguistic expertise and EEG gamma band phase synchrony. Front. Psychol. 2, (2011).

Rogalsky C, Rong F, Saberi K, Hickok G. 2011. Functional anatomy of language and music perception: temporal and structural factors investigated using functional magnetic resonance imaging. Journal of Neuroscience 31: 3843-3852. DOI: https://doi.org/10.1523/JNEUROSCI.4515-10.2011, PMID: 21389239.

Rohrmeier M, Cross I. 2008. Statistical properties of harmony in bach's Chorales. Proceedings of the 10th International Conference on Music Perception and Cognition p. 619-627.

Rohrmeier M, Rebuschat P, Cross 1. 2011. Incidental and online learning of melodic structure. Consciousness and Cognition 20:214-222. DOI: https://doi.org/10.1016/j.concog.2010.07.004.

Romberg AR, Saffran JR. 2010. Statistical learning and language acquisition. Wiley Interdisciplinary Reviews: Cognitive Science 1:906-914. DOI: https://doi.org/10.1002/wcs.78.

Rongzhi Gu, Jian Wu, Shi-Xiong Zhang, Lianwu Chen, Yong Xu, Meng Yu, Dan Su, Yuexian Zou, and Dong Yu, "End- to-end multi-channel speech separation," arXiv preprint arXiv:1905.06286, 2019.

Roux, J.L., Wisdom, S., Erdogan, H., Hershey, J.R. , 2019. Sdr half-baked or well done? In: 2019 IEEE International Conference on Acoustics, Speech and Signal Processing (ICASSP), pp. 626-630.

Russ BE, Lee YS, Cohen YE. 2007. Neural and behavioral correlates of auditory categorization. Hearing Research 229:204-212. DOI: https://doi.org/10.1016/j.heares.2006.10.010, PMID: 17208397.

S. Doclo, T. J. Klasen, T. Van den Bogaert, J. Wouters, and M. Moonen, "Theoretical analysis of binaural cue preservation using multi-channel wiener filtering and interaural transferfunctions," in Proc. Int. Workshop Acoust. Echo Noise Control (IWAENC), 2006, pp. 1-4.

S. Gannot, D. Burshtein, and E. Weinstein, "Signal enhancement using beamforming and nonstationarity with applications to speech," IEEE Transactions on Signal Processing, vol. 49, No. 8, pp. 1614-1626, 2001.

S. Venkataramani, J. Casebeer, and P. Smaragdis, "End-to-end source separation with adaptive front-ends," in 2018 52nd Asilomar Conference on Signals, Systems, and Computers. IEEE, 2018, pp. 684-688.

Sadagopan S, Wang X. 2009. Nonlinear spectrotemporal interactions underlying selectivity for complex sounds in auditory cortex. Journal of Neuroscience 29:11192-11202. DOI: https://doi.org/10.1523/JNEUROSCI.1286-09.2009, PMID: 19741126.

Saffran JR, Newport EL, Aslin RN, Tunick RA, Barrueco S. 1997. Incidental Language Learning: Listening (and Learning) Out of the Corner of Your Ear. Psychological Science 8:101-105. DOI: https://doi.org/10.1111/i.1467-9280.1997.tb00690.x.

Salimpoor VN, Benovoy M, Longo G, Cooperstock JR, Zatorre RJ. 2009. The rewarding aspects of music listening are related to degree of emotional arousal. PLOS ONE 4:e7487. DOI: https://doi.org/10.1371/journal.pone.0007487, PMID: 19834599.

Salimpoor VN, van den Bosch I, Kovacevic N, Mcintosh AR, Dagher A, Zatorre RJ. 2013. Interactions between the nucleus accumbens and auditory cortices predict music reward value. Science 340:216-219. DOI: https://doi.org/10.1126/science.1231059, PMID: 23580531.

Salimpoor VN, Zald DH, Zatorre RJ, Dagher A, Mcintosh AR. 2015. Predictions and the brain: how musical sounds become rewarding. Trends in Cognitive Sciences 19:86-91. DOI: https://doi.org/10.1016/j.tics.2014.12.001, PMID: 25534332.

Salmi, J., Rinne, T., Koistinen, S., Salonen, O., and Alho, K. (2009). Brain networks of bottom-up triggered and top-down controlled shifting of auditory attention. Brain Res. 1286, 155-164.

Sammler D, Koelsch S, Ball T, Brandt A, Grigutsch M, Huppertz HJ, Kno sche TR, Wellmer J, Widman G, Elger CE, Friederici AD, Schulze-Bonhage A. 2013. Co-localizing linguistic and musical syntax with intracranial EEG. NeuroImage 64:134-146. DOI: https://doi.org/10.1016/j.neuroimage.2012.09.035, PMID: 23000255.

Santoro, R. et al. Reconstructing the spectrotemporal modulations of real-life sounds from fMRI response patterns. Proc. Natl. Acad. Sci. U. S. A. 114, 4799-4804 (2017).

Santoro, R., Moerel, M., De Martino, F., Goebel, R., Ugurbil, K., Yacoub, E., and Formisano, E. (2014). Encoding of natural sounds at multiple spectral and temporal resolutions in the human auditory cortex. PLoS Comput. Biol. 10, e1003412.

Schaal NK, Pollok B, Banissy MJ. 2017. Hemispheric differences between left and right supramarginal gyrus for pitch and rhythm memory. Scientific Reports 7:42456. DOI: https://doi.org/10.1038/srep42456.

(56) References Cited

OTHER PUBLICATIONS

Schaal NK, Williamson VJ, Kelly M, Muggleton NG, Pollok B, Krause V, Banissy MJ. 2015. A causal involvement of the left supramarginal gyrus during the retention of musical pitches. Cortex 64:310-317. DOI: https://doi.org/10.1016/j.cortex.2014.11.011.

Schmuckler MA. 1989. Expectation in Music: Investigation of Melodic and Harmonic Processes. Music Perception: An Interdisciplinary Journal 7:109-149. DOI: https://doi.org/10.2307/40285454.

Schonwiesner M, Zatorre RJ. 2008. Depth electrode recordings show double dissociation between pitch processing in lateral Heschl's gyrus and sound onset processing in medial Heschl's gyrus. Experimental Brain Research 187:97-105. DOI: https://doi.org/10.1007/s00221-008-1286-z.

Schoppe O, Harper NS, Willmore BD, King AJ, Schnupp JW. 2016. Measuring the performance of neural models. Frontiers in Computational Neuroscience 10:10. DOI: https://doi.org/10.3389/fncom.2016.00010, PMID: 26903851.

Schwartz O, Chichilnisky EJ, Simoncelli EP. 2002. Characterizing neural gain control using spike-triggered covariance. Advances in Neural Information Processing System 269-276.

Khalighinejad, Bahar., et al., "Functional characterization of human Heschl's gyrus in response to natural speech," bioRxiv, (2020) : 86-115.

Khodagholy, D., Gelinas, J.N., Thesen, T., Doyle, W., Devinsky, O., Malliaras,G.G., and Buzsáki, G. (2015). NeuroGrid: recording action potentials from the surface of the brain. Nat. Neurosci. 18, 310-315.

Kilian-Hutten, N., Valente, G., Vroomen, J., and Formisano, E. (2011). Auditory cortex encodes the perceptual interpretation of ambiguous sound. J. Neurosci. 31, 1715-1720.

Kim, K. H. S., Relkin, N. R., Lee, K. M. & Hirsch, J. Distinct cortical areas associated with native and second languages. Nature 388, 171-174 (1997).

Kimppa, L. et al. Acquisition of L2 morphology by adult language learners. Cortex 116, 74-90 (2019).

King, A.J., and Nelken, I. (2009). Unraveling the principles of auditory cortical processing: can we learn from the visual system? Nat. Neurosci. 12, 698-701.

Kiselev, I., Ceolini, E., Wong, D., d. Cheveigne, A., Liu, S.C., 2017. Whisper: Wirelessly synchronized distributed audio sensor platform. In: 2017 IEEE 42nd Con-ference on Local Computer Networks Workshops (LCN Workshops), pp. 35-43. doi: 10.1109/LCN.Workshops.2017.62.

Klein DJ, Simon JZ, Depireux DA, Shamma SA. 2006. Stimulus-invariant processing and spectrotemporal reverse correlation in primary auditory cortex. Journal of Computational Neuroscience 20:111-136. DOI: https://doi.org/10.1007/s10827-005-3589-4, PMID: 16518572.

Klindt D, Ecker AS, Euler T, Bethge M. 2017. Neural system identification for large populations separating "what" and "where.". Advances in Neural Information Processing Systems. 3509-3519. DOI: https://doi.org/10.12751/nncn.bc2017.0132.

Koelsch S, Grossmann T, Gunter TC, Hahne A, Schroger E, Friederici AD. 2003. Children processing music: electric brain responses reveal musical competence and gender differences. Journal of Cognitive Neuroscience 15:683-693. DOI: https://doi.org/10.1162/jocn.2003.15.5.683, PMID: 12965042.

Koelsch S, Gunter T, Friederici AD, Schroger E. 2000. Brain indices of music processing: "nonmusicians" are musical. Journal of Cognitive Neuroscience 12:520-541. DOI: https://doi.org/10.1162/089892900562183,PMID: 10931776.

Koelsch S, Jentschke S, Sammler D, Mietchen D. 2007. Untangling syntactic and sensory processing: an ERP study of music perception. Psychophysiology 44:476-490. DOI: https://doi.org/10.1111/j.1469-8986.2007.00517.x, PMID: 17433099.

Koelsch S, Jentschke S. 2008. Short-term effects of processing musical syntax: an ERP study. Brain Research 1212:55-62. DOI: https://doi.org/10.1016/j.brainres.2007.10.078, PMID: 18439987.

Koelsch S, Schmidt B-helmer, Kansok J. 2002. Effects of musical expertise on the early right anterior negativity: an event-related brain potential study. Psychophysiology 39:657-663. DOI: https://doi.org/10.1111/1469-8986.3950657.

Koelsch S. 2009. Music-syntactic processing and auditory memory: similarities and differences between ERAN and MMN. Psychophysiology 46:179-190. DOI: https://doi.org/10.1111/j.1469-8986.2008.00752.x, PMID: 19055508.

Koelsch S. 2014. Brain correlates of music-evoked emotions. Nature Reviews Neuroscience 15:170-180. DOI: https://doi.org/10.1038/nrn3666, PMID: 24552785.

Kok P, Jehee JF, de Lange FP. 2012. Less is more: expectation sharpens representations in the primary visual cortex. Neuron 75:265-270. DOI: https://doi.org/10.1016/j.neuron.2012.04.034, PMID: 22841311.

Kotz, S. A. A critical review of ERP and fMRI evidence on L2 syntactic processing. Brain Lang. 109, 68-74 (2009).

Krishnan, L., Elhilali, M., and Shamma, S. (2014). Segregating complex sound sources through temporal coherence. PLoS Comput. Biol. 10, e1003985.

Krizhevsky A, Sutskever I, Hinton GE. 2012. ImageNet classification with deep convolutional neural networks. Advances in Neural Information Processing Systems 1097-1105.

Krizman, J., Slater, J., Skoe, E., Marian, V. & Kraus, N. Neural processing of speech in children is influenced by extent of bilingual experience. Neurosci. Lett. 585, 48-53 (2015).

Krumhansl CL, Toivanen P, Eerola T, Toiviainen P, Jarvinen T, Louhivuori J. 2000. Cross-cultural music cognition: cognitive methodology applied to north sami yoiks. Cognition 76:13-58. DOI: https://doi.org/10.1016/S0010-0277(00)00068-8, PMID: 10822042.

Kubanek J, Brunner P, Gunduz A, Poeppel D, Schalk G. 2013. The tracking of speech envelope in the human cortex. PLOS ONE 8:e53398. DOI: https://doi.org/10.1371/journal.pone.0053398, PMID: 23408924.

Kuhl, P. K. Early Language Learning and Literacy: Neuroscience Implications for Education. Mind, Brain, Educ. 5, 128-142 (2011).

Kuhl, P. K. et al. Phonetic learning as a pathway to language: New data and native language magnet theory expanded (NLM-e). Philosophical Transactions of the Royal Society B: Biological Sciences 363, 979-1000 (2008).

Kuperberg, G. R. & Jaeger, T. F. What do we mean by prediction in language comprehension? Lang. Cogn. Neurosci. 31, 32-59 (2016).

Kutas, M. & Federmeier, K. D. Thirty years and counting: finding meaning in the N400 component of the event-related brain potential (ERP). Annu. Rev. Psychol. 62, 621-47 (2011).

Kutas, M. & Hillyard, S. A. Reading senseless sentences: Brain potentials reflect semantic incongruity. Science (80-. ). 207, 203-205 (1980).

L. Zhang, Z. Shi, J. Han, A. Shi, and D. Ma, "Furcanext: End-to-end monaural speech separation with dynamic gated dilated temporal convolutional networks," in International Conference on Multimedia Modeling. Springer, 2020, pp. 653-665.

Lalor EC, Pearlmutter BA, Reilly RB, McDarby G, Foxe JJ. 2006. The VESPA: a method for the rapid estimation of a visual evoked potential. NeuroImage 32:1549-1561. DOI: https://doi.org/10.1016/j.neuroimage.2006.05.054, PMID: 16875844.

Lalor, E. C. & Foxe, J. J. Neural responses to uninterrupted natural speech can be extracted with precise temporal resolution. Eur. J. Neurosci. 31, 189-193 (2010).

Lalor, E. C., Power, A. J., Reilly, R. B. & Foxe, J. J. Resolving Precise Temporal Processing Properties of the Auditory System Using Continuous Stimuli. J. Neurophysiol. 102, 349-359 (2009).

Laurent G, Davidowitz H. 1994. Encoding of olfactory information with oscillating neural assemblies. Science 265:1872-1875. DOI: https://doi.org/10.1126/science.265.5180.1872, PMID: 17797226.

Lea C, Vidal R, Reiter A, Hager GD. 2016. Temporal convolutional networks: A unified approach to action segmentation. In: Hua G, Je' gou H (Eds). European Conference on Computer Vision. Springer. p. 47-54. DOI: https://doi.org/10.1007/978-3-319-49409-8_7.

Leaver, A.M., and Rauschecker, J.P. (2010). Cortical representation of natural complex sounds: effects of acoustic features and auditory object category. J. Neurosci. 30, 7604-7612.

(56) References Cited

OTHER PUBLICATIONS

Leaver, A.M., and Rauschecker, J.P. (2016). Functional topography of human auditory cortex. J. Neurosci. 36, 1416-1428.

Lecaignard F, Bertrand O, Gimenez G, Mattout J, Caclin A. 2015. Implicit learning of predictable sound sequences modulates human brain responses at different levels of the auditory hierarchy. Frontiers in Human Neuroscience 9:505. DOI: https://doi.org/10.3389/fnhum.2015.00505, PMID: 26441602.

LeCun Y, Bengio Y, Hinton G. 2015. Deep learning. Nature 521:436-444. DOI: https://doi.org/10.1038/nature14539, PMID: 26017442.

LeCun Y, Bengio Y. 1995. Convolutional networks for images, speech, and time series. the Handbook of Brain Theory and Neural Networks.

LeCun Y, Boser BE, Denker JS, Henderson D, Howard RE, Hubbard WE. 1990. Handwritten digit recognition with a back-propagation network. Advances in Neural Information Processing Systems 396-404.

LeCun Y, Bottou L, Bengio Y, Haffner P. 1998. Gradient-based learning applied to document recognition. Proceedings of the IEEE 2278-2323. DOI: https://doi.org/10.1109/5.726791.

Lee, A.K.C., Larson, E., Maddox, R.K., and Shinn-Cunningham, B.G. (2014). Using neuroimaging to understand the cortical mechanisms of auditory selective attention. Hear. Res. 307, 111-120.

Leonard, M.K., Baud, M.O., Sjerps, M.J., and Chang, E.F. (2016). Perceptual restoration of masked speech in human cortex. Nat. Commun. 7, 13619.

Leonard, M.K., Bouchard, K.E., Tang, C., and Chang, E.F. (2015). Dynamic encoding of speech sequence probability in human temporal cortex. J. Neurosci. 35, 7203-7214.

Lesenfants, D., Vanthornhout, J., Verschueren, E. & Francart, T. Data-driven spatial filtering for improved measurement of cortical tracking of multiple representations of speech. J. Neural Eng. (2019). doi:10.1088/1741-2552/ab3c92.

Lev-Ari, S. & Keysar, B. Why don't we believe non-native speakers? The influence of accent on credibility. (2010). doi:10.1016/j.jesp.2010.05.025.

Linden, J.F., Liu, R.C., Sahani, M., Schreiner, C.E., and Merzenich, M.M. (2003). Spectrotemporal structure of receptive fields in areas AI and AAF of mouse auditory cortex. J. Neurophysiol. 90, 2660-2675.

Liu, Y., Wang, D., 2019. Divide and conquer: a deep casa approach to talker-independent monaural speaker separation. IEEE/ACM Trans. Audio Speech Lang. Process. 27 (12), 2092-2102.

Lloyd S. 1982. Least squares quantization in PCM. IEEE Transactions on Information Theory 129-137. DOI: https://doi.org/10.1109/TIT.1982.1056489.

Lopez Espejo M, Schwartz ZP, David SV. 2019. Spectral tuning of adaptation supports coding of sensory context in auditory cortex. PLOS Computational Biology 15:e1007430. DOI: https://doi.org/10.1371/journal.pcbi.1007430, PMID: 31626624.

Fishman, Y.I., Micheyl, C., and Steinschneider, M. (2016). Neural Representation of Concurrent Vowels in Macaque Primary Auditory Cortex. Eneuro 3, ENEURO-0071.

Fitch WT, Martins MD. 2014. Hierarchical processing in music, language, and action: lashley revisited. Annals of the New York Academy of Sciences 1316:87-104. DOI: https://doi.org/10.1111/nyas.12406.

Flege, J. E. Second Language Speech Learning: Theory, Findings, and Problems. Speech Percept. Linguist. Exp. Issues Cross-Language Res. 233-277 (1995). doi:10.1111/j.1600-0404.1995.tb01710.x.

Flege, J. E. The production and perception of foreign language speech sounds. Hum. Commun. its Disord. a Rev.—1988 224-401 (1988).

Flege, J. E. The production of 'new' and 'similar' phones in a foreign language: evidence for the effect of equivalence classification. Journal of Phonetics 15, (1987).

Flinker, A., Doyle, W.K., Mehta, A.D., Devinsky, O., and Poeppel, D. (2019). Spectrotemporal modulation provides a unifying framework for auditory cortical asymmetries. Nat. Hum. Behav. 3, 393-405.

Fontolan, L., Morillon, B., Liegeois-Chauvel, C., and Giraud, A.L. (2014). The contribution of frequency-specific activity to hierarchical information processing in the human auditory cortex. Nat. Commun. 5, 4694.

Formisano, E., De Martino, F., Bonte, M., and Goebel, R. (2008). "Who" Is Saying "What"? Brain Based Decoding of Human Voice and Speech. Science (80-. ). 322, 970.

Formisano, E., Kim, D.-S., Di Salle, F., van de Moortele, P.-F., Ugurbil, K., and Goebel, R. (2003). Mirror-symmetric tonotopic maps in human primary auditory cortex. Neuron 40, 859-869.

Frank, S. L. & Willems, R. M. Word predictability and semantic similarity show distinct patterns of brain activity during language comprehension. Lang. Cogn. Neurosci. 32, 1192-1203 (2017).

Friston K, Kiebel S. 2009. Predictive coding under the free-energy principle. Philosophical Transactions of the Royal Society B: Biological Sciences 364:1211-1221. DOI: https://doi.org/10.1098/rstb.2008.0300.

Fritz, J., Shamma, S., Elhilali, M., and Klein, D. (2003). Rapid task-related plasticity of spectrotemporal receptive fields in primary auditory cortex. Nat. Neurosci. 6, 1216-1223.

Fuglsang, S., Märcher-Rørsted, J., Dau, T., Hjortkjær, J., 2020. Effects of sensorineural hearing loss on cortical synchronization to competing speech during selective atten-tion . . . J. Neurosci.

Fuglsang, S.A., Dau, T., Hjortkjær, J., 2017. Noise-robust cortical tracking of attended speech in real-world acoustic scenes. Neuroimage 156, 435-444.

Galaburda A, Sanides F. 1980. Cytoarchitectonic organization of the human auditory cortex. The Journal of Comparative Neurology 190:597-610. DOI: https://doi.org/10.1002/cne.901900312, PMID: 6771305.

Gannot, S. , Vincent, E. , Golan, S.M. , Ozerov, A. , 2017. A consolidated perspective on multimicrophone speech enhancement and source separation. IEEE/ACM Trans. Audio Speech Lang. Process. 25, 692-730.

Garrido MI, Kilner JM, Stephan KE, Friston KJ. 2009. The mismatch negativity: a review of underlying mechanisms. Clinical Neurophysiology 120:453-463. DOI: https://doi.org/10.1016/j.clinph.2008.11.029,PMID: 19181570.

Geirnaert, S., Francart, T., Bertrand, A., 2020. An interpretable performance metric for auditory attention decoding algorithms in a context of neuro-steered gain control. IEEE Trans. Neural Syst. Rehabil. Eng. 28 (1), 307-317. doi: 10.1109/TNSRE.2019.2952724.

Gold BP, Pearce MT, Mas-Herrero E, Dagher A, Zatorre RJ. 2019. Predictability and uncertainty in the pleasure of music: a reward for learning? The Journal of Neuroscience 39:9397-9409. DOI: https://doi.org/10.1523/JNEUROSCI.0428-19.2019, PMID: 31636112.

Goldwater, S. & Johnson, M. Learning OT Constraint Rankings Using a Maximum Entropy Model. Proc. Stock. Work. Var. within Optim. Theory 111-120 (2003).

Griffiths TD, Warren JD. 2002. The planum temporale as a computational hub. Trends in Neurosciences 25:348-353. DOI: https://doi.org/10.1016/S0166-2236(02)02191-4.

Groppe, D.M., Bickel, S., Dykstra, A.R., Wang, X., Mégevand, P., Mercier, M.R., Lado, F.A., Mehta, A.D., and Honey, C.J. (2017). iELVis: An open source MATLAB toolbox for localizing and visualizing human intracranial electrode data. J. Neurosci. Methods 281, 40-48.

Guion, S. G., Flege, J. E., Akahane-Yamada, R. & Pruitt, J. C. An investigation of current models of second language speech perception: The case of Japanese adults' perception of English consonants. J. Acoust. Soc. Am. 107, 2711-2724 (2000).

Guoning Hu, "100 Nonspeech Sounds," http://web.cse.ohio-state.edu/pnl/corpus/HuNonspeech/HuCorpus.html.

Guyon I, Elisseeff A. 2003. An introduction to variable and feature selection. Journal of Machine Learning Research 3:1157-1182.

H. Haas, "The influence of a single echo on the audibility of speech," Journal of the Audio Engineering Society, vol. 20, No. 2, pp. 146-159, 1972.

(56) References Cited

OTHER PUBLICATIONS

Hackett, T.A. (2008). Anatomical organization of the auditory cortex. J. Am. Acad. Audiol. 19, 774-779.
Hackett, T.A., Preuss, T.M., and Kaas, J.H. (2001). Architectonic identification of the core region in auditory cortex of macaques, chimpanzees, and humans. J. Comp. Neurol. 441, 197-222.
Hackett, T.A., Stepniewska, I., and Kaas, J.H. (1998). Subdivisions of auditory cortex and ipsilateral cortical connections of the parabelt auditory cortex in macaque monkeys. J. Comp. Neurol. 394, 475-495.
Hagoort, P. & Brown, C. M. ERP effects of listening to speech: Semantic ERP effects. Neuropsychologia 38, 1518-1530 (2000).
Hakan Erdogan, John R. Hershey, Shinji Watanabe, Michael I. Mandel, and Jonathan Le Roux, "Improved MVDR beamforming using single-channel mask prediction networks.," in Interspeech, 2016, pp. 1981-1985.
Hakan Erdogan, Tomoki Hayashi, John R Hershey, Takaaki Hori, Chiori Hori, Wei-Ning Hsu, Suyoun Kim, Jonathan Le Roux, Zhong Meng, and Shinji Watanabe, "Multi-channel speech recognition: Lstms all the way through," in CHiME-4 workshop, 2016.
Hale J, Dyer C, Kuncoro A, Brennan JR. 2018. Finding syntax in human encephalography with beam search. Proceedings of the 56th Annual Meeting of the Association for Computational Linguistics (vol. 1: Long Papers), Melbourne, Australia 2727-2736. DOI: https://doi.org/10.18653/v1/P18-1254.
Hamilton, L.S., and Huth, A.G. (2018). The revolution will not be controlled: natural stimuli in speech neuroscience. Lang. Cogn. Neurosci. 1-10.
Hamilton, L.S., Edwards, E., and Chang, E.F. (2018). A spatial map of onset and sustained responses to speech in the human superior temporal gyrus. Curr. Biol. 28, 1860-1871.e4.
Han, C., Luo, Y., Mesgarani, N., 2019. Online deep attractor network for real-time single-channel speech separation. In: ICASSP 2019—2019 IEEE International Conference on Acoustics, Speech and Signal Processing (ICASSP), pp. 361-365. doi: 10.1109/ICASSP.2019.8682884.
Han, C., O'Sullivan, J., Luo, Y., Herrero, J., Mehta, A.D., and Mesgarani, N. (2019). Speaker-independent auditory attention decoding without access to clean speech sources. Sci. Adv. 5, eaav6134.
Han, Z. H. Fossilization in adult second language acquisition. Fossilization in Adult Second Language Acquisition (2004) doi:10.25264/2519-2558-2019-6(74)-150-153.
Hanna, J., Shtyrov, Y., Williams, J. & Pulvermüller, F. Early neurophysiological indices of second language morphosyntax learning. Neuropsychologia 82, 18-30 (2016).
Hannon EE, Soley G, Ullal S. 2012. Familiarity overrides complexity in rhythm perception: a cross-cultural comparison of american and turkish listeners. Journal of Experimental Psychology: Human Perception and Performance 38:543-548. DOI: https://doi.org/10.1037/a0027225.
Hansen NC, Pearce MT. 2014. Predictive uncertainty in auditory sequence processing. Frontiers in Psychology 5: 1052. DOI: https://doi.org/10.3389/fpsyg_2014.01052, PMID: 25295018.
Harper NS, Schoppe O, Willmore BD, Cui Z, Schnupp JW, King AJ. 2016. Network receptive field modeling reveals extensive integration and Multi-feature selectivity in auditory cortical neurons. PLOS Computational Biology 12: e1005113. DOI: https://doi.org/10.1371/journal.pcbi.1005113, PMID: 27835647.
Hartline HK. 1940. The receptive fields of optic nerve fibers. American Journal of Physiology-Legacy Content 130:690-699. DOI: https://doi.org/10.1152/ajplegacy.1940.130.4.690.
Hartshorne, J. K., Tenenbaum, J. B. & Pinker, S. A critical period for second language acquisition: Evidence from 2/3 million English speakers. Cognition 177, 263-277 (2018).
Hausfeld, L., Riecke, L., Valente, G. & Formisano, E. Cortical tracking of multiple streams outside the focus of attention in naturalistic auditory scenes. Neuroimage 181, 617-626 (2018).
Hayes, B. & Wilson, C. A Maximum Entropy Model of Phonotactics and Phonotactic Learning. Linguist. Inq. 39, 379-440 (2008).

He K, Zhang X, Ren S, Sun J. 2015. Delving deep into rectifiers: surpassing human-level performance on imagenet classification. Proceedings of the 2015 IEEE International Conference on Computer Vision (ICCV) 1026-1034. DOI: https://doi.org/10.1109/ICCV.2015.123.
Heffner CC, Slevc LR. 2015. Prosodic structure as a parallel to musical structure. Frontiers in Psychology 6:1962. DOI: https://doi.org/10.3389/fpsyg.2015.01962, PMID: 26733930.
Henin S, Turk-Browne N, Friedman D, Liu A, Dugan P, Flinker A, Doyle W, Devinsky O, Melloni L. 2019. Statistical learning shapes neural sequence representations. bioRxiv. DOI: https://doi.org/10.1101/583856.
Herdener, M., Esposito, F., Scheffler, K., Schneider, P., Logothetis, N.K., Uludag, K., and Kayser, C. (2013). Spatial representations of temporal and spectral sound cues in human auditory cortex. Cortex 49, 2822-2833.
Tsodyks M, Pawelzik K, Markram H. 1998. Neural networks with dynamic synapses. Neural Computation 10:821-835. DOI: https://doi.org/10.1162/089976698300017502, PMID: 9573407.
Tsubasa Ochiai, Shinji Watanabe, Takaaki Hori, and John R Hershey, "Multichannel end-to-end speech recognition," arXiv preprint arXiv:1703.04783, 2017.
Tsubasa Ochiai, Shinji Watanabe, Takaaki Hori, John R Hershey, and Xiong Xiao, "Unified architecture for multichannel end-to-end speech recognition with neural beamforming," IEEE Journal of Selected Topics in Signal Processing, vol. 11,No. 8, pp. 1274-1288, 2017.
Tucker, G. R. A Global Perspective on Bilingualism and Bilingual Education. Socioling. Essent. Readings 000, 464-471 (2001).
Upadhyay, J., Ducros, M., Knaus, T.A., Lindgren, K.A., Silver, A., Tager-Flusberg, H., and Kim, D.-S. (2006). Function and connectivity in human primary auditory cortex: a combined fMRI and DTI study at 3 Tesla. Cereb. Cortex 17, 2420-2432.
V. R. Algazi, R. O. Duda, D. M. Thompson, and C. Avendano, "The cipic href database," in Proceedings of the 2001 IEEE Workshop on the Applications of Signal Processing to Audio and Acoustics (Cat. No. 01TH8575). IEEE, 2001, pp. 99-102.
Van den Oord, A., Dieleman, S., Zen, H., Simonyan, K., Vinyals, O., Graves, A., Kalch-brenner, N., Senior, A., Kavukcuoglu, K., 2016. Wavenet: A generative model for raw audio. Arxiv.
Van Eyndhoven, S., Francart, T., Bertrand, A., 2017. EEG-Informed attended speaker extraction from recorded speech mixtures with application in neuro-steered hearing prostheses. IEEE Trans. Biomed. Eng. 64 (5), 1045-1056. doi: 10.1109/TBME.2016.2587382.
Van Petten, C. & Kutas, M. Interactions between sentence context and word frequency in event-related brain potentials. Mem. Cognit. 18, 380-393 (1990).
Vanthornhout J, Decruy L, Wouters J, Simon JZ, Francart T. 2018. Speech Intelligibility Predicted from Neural Entrainment of the Speech Envelope. Journal of the Association for Research in Otolaryngology 19:181-191. DOI: https://doi.org/10.1007/s10162-018-0654-z.
Vassil Panayotov, Guoguo Chen, Daniel Povey, and Sanjeev Khudanpur, "Librispeech: an ASR corpus based on public domain audio books," in Acoustics, Speech and Signal Processing (ICASSP), 2015 IEEE International Conference on. IEEE, 2015, pp. 5206-5210.
Verschueren E, Somers B, Francart T. 2019. Neural envelope tracking as a measure of speech understanding in cochlear implant users. Hearing Research 373:23-31. DOI: https://doi.org/10.1016/j.heares.2018.12.004,PMID: 30580236.
Viemeister, N.F. (1979). Temporal modulation transfer functions based upon modulation thresholds. J. Acoust. Soc. Am. 66, 1364-1380.
Vines BW, Schnider NM, Schlaug G. 2006. Testing for causality with transcranial direct current stimulation: pitch memory and the left supramarginal gyrus. NeuroReport 17:1047-1050. DOI: https://doi.org/10.1097/01.wnr.0000223396.05070.a2, PMID: 16791101.
Vintch B, Movshon JA, Simoncelli EP. 2015. A convolutional subunit model for neuronal responses in macaque V1. Journal of Neuroscience 35:14829-14841. DOI: https://doi.org/10.1523/JNEUROSCI.2815-13.2015, PMID: 26538653.

(56) References Cited

OTHER PUBLICATIONS

Vuust P, Brattico E, Seppanen M, Naatanen R, Tervaniemi M. 2012. The sound of music: differentiating musicians using a fast, musical multi-feature mismatch negativity paradigm. Neuropsychologia 50:1432-1443. DOI: https://doi.org/10.1016/j.neuropsychologia.2012.02.028, PMID: 22414595.
Walker, K.M.M., Bizley, J.K., King, A.J., and Schnupp, J.W.H. (2011). Multiplexed and robust representations of sound features in auditory cortex. J. Neurosci. 31, 14565-14576.
Wang S, Mohamed A-R, Caruana R, Bilmes J, Plilipose M, Richardson M. 2016. Analysis of deep neural networks with the extended data jacobian matrix. Proceedings of the 33rd International Conference on Machine Learning 718-726.
Wang, D., Chen, J., 2018. Supervised speech separation based on deep learning: an overview. IEEE/ACM Trans. Audio Speech Lang. Process. 26 (10), 1702-1726.
Wang, J., Chen, J., Su, D. , Chen, L., Yu, M. , Qian, Y., Yu, D., 2018. Deep extractor network for target speaker recovery from single channel speech mixtures. Interspeech.
Wang, K. & Shamma, S. Self-Normalization and Noise-Robustness in Early Auditory Representations. IEEE Trans. Speech Audio Process. 2, 421-435 (1994).
Wang, Y., Ding, N., Ahmar, N., Xiang, J., Poeppel, D., and Simon, J.Z. (2011). Sensitivity to temporal modulation rate and spectral bandwidth in the human auditory system: MEG evidence. J. Neurophysiol. 107, 2033-2041.
Weber-Fox, C. M. & Neville, H. J. Maturational Constraints on Functional Specializations for Language Processing: ERP and Behavioral Evidence in Bilingual Speakers. J. Cogn. Neurosci. 8, 231-56 (1996).
Webster, D.B., and Fay, R.R. (2013). The Mammalian Auditory Pathway: Neuroanatomy (Springer Science & Business Media).
Wernicke, C. (1874). Der aphasische Symptomencomplex: eine psychologische Studie auf anatomischer Basis (Cohn.).
Wessinger, C.M., Buonocore, M.H., Kussmaul, C.L., and Mangun, G.R. (1997). Tonotopy in human auditory cortex examined with functional magnetic resonance imaging. Hum. Brain Mapp. 5, 18-25.
White, E. J., Genesee, F. & Steinhauer, K. Brain Responses before and after Intensive Second Language Learning: Proficiency Based Changes and First Language Background Effects in Adult Learners. PLoS One 7, (2012).
Williamson, D.S., Wang, Y., Wang, D., 2016. Complex ratio masking for monaural speech separation. IEEE/ACM Transactions on Audio, Speech and Language Process-ing (TASLP) 24 (3), 483-492.
Wilson DA. 2001. Receptive fields in the rat piriform cortex. Chemical Senses 26:577-584. DOI: https://doi.org/10.1093/chemse/26.5.577, PMID: 11418503.
Wlotko, E. W. & Federmeier, K. D. So that's what you meant! Event-related potentials reveal multiple aspects of context use during construction of message-level meaning. Neuroimage 62, 356-366 (2012).
Wong DDE, Fuglsang SA, Hjortkjær J, Ceolini E, Slaney M, de Cheveigne' A. 2018. A comparison of regularization methods in forward and backward models for auditory attention decoding. Frontiers in Neuroscience 12:531. DOI: https://doi.org/10.3389/fnins.2018.00531, PMID: 30131670.
Wong, D.D.E., Hjortkjær, J., Ceolini, E., Nielsen, S.V., Griful, S.R., Fuglsang, S., Chait, M., Lunner, T., Dau, T., Liu, S.-C. , de Cheveigné, A. , 2018. A closed-loop platform for real-time attention control of simultaneous sound streams. ARO Midwinter meeting (abstract), ARO Midwinter meeting (abstract).
Woolley SM. 2012. Early experience shapes vocal neural coding and perception in songbirds. Developmental Psychobiology 54:612-631. DOI: https://doi.org/10.1002/dev_21014, PMID: 22711657.
Woolley, S.M.N., Fremouw, T.E., Hsu, A., and Theunissen, F.E. (2005). Tuning for spectro-temporal modulations as a mechanism for auditory discrimination of natural sounds. Nat. Neurosci. 8, 1371-1379.
Wu MC, David SV, Gallant JL. 2006. Complete functional characterization of sensory neurons by system identification. Annual Review of Neuroscience 29:477-505. DOI: https://doi.org/10.1146/annurev.neuro.29.051605.113024, PMID: 16776594.
X. Sun, R. Xia, J. Li, and Y. Yan, "A deep learning based binaural speech enhancement approach with spatial cues preservation," in ICASSP 2019-2019 IEEE International Conference on Acoustics, Speech and Signal Processing (ICASSP). IEEE, 2019, pp. 5766-5770.
X. Zhang and D. Wang, "Deep learning based binaural speech separation in reverberant environments," IEEE/ACM transactions on audio, speech, and language processing, vol. 25, No. 5, pp. 1075-1084, 2017.
Xiao, X., Chen, Z., Yoshioka, T., Erdogan, H., Liu, C., Dimitriadis, D., Droppo, J., Gong, Y., 2019. Single-channel speech extraction using speaker inventory and attention network. In: ICASSP 2019—2019 IEEE International Conference on Acoustics, Speech and Signal Processing (ICASSP), pp. 86-90.
Xiong Xiao, Chenglin Xu, Zhaofeng Zhang, Shengkui Zhao,Sining Sun, Shinji Watanabe, Longbiao Wang, Lei Xie, Douglas L Jones, Eng Siong Chng, et al., "A study of learning based beamforming methods for speech recognition," in CHiME 2016 workshop, 2016, pp. 26-31.
Xiong Xiao, Shengkui Zhao, Douglas L Jones, Eng Siong Chng, and Haizhou Li, "On time-frequency mask estimation for mvdr beamforming with application in robust speech recognition," in Acoustics, Speech and Signal Processing (ICASSP), 2017 IEEE International Conference on. IEEE, 2017, pp. 3246-3250.
Xiong Xiao, Shinji Watanabe, Eng Siong Chng, and Haizhou Li, "Beamforming networks using spatial covariance features for farfield speech recognition," in Signal and Information Processing Association Annual Summit and Conference (APSIPA), 2016 Asia-Pacific. IEEE, 2016, pp. 1-6.
Xiong Xiao, Shinji Watanabe, Hakan Erdogan, Liang Lu, John Hershey, Michael L Seltzer, Guoguo Chen, Yu Zhang, Michael Mandel, and Dong Yu, "Deep beamforming networks for multichannel speech recognition," in Acoustics, Speech and Signal Processing (ICASSP), 2016 IEEE International Conference on. IEEE, 2016, pp. 5745-5749.
Xueliang Zhang, Zhong-Qiu Wang, and DeLiang Wang, "A speech enhancement algorithm by iterating single-and multimicrophone processing and its application to robust asr," in Acoustics, Speech and Signal Processing (ICASSP), 2017 IEEE International Conference on. IEEE, 2017, pp. 276-280.
Y. Isik, J. Le Roux, Z. Chen, S. Watanabe, and J. R. Hershey, "Single-channel multi-speaker separation using deep clustering," Interspeech 2016, pp. 545-549, 2016.
Y. Liu and D. Wang, "Divide and conquer: A deep casa approach to talker-independent monaural speaker separation," IEEE/ACM Transactions on Audio, Speech, and Language Processing (TASLP), vol. 27, No. 12, pp. 2092-2102, 2019.
Y. Luo, E. Ceolini, C. Han, S.-C. Liu, and N. Mesgarani, "Fasnet: Low-latency adaptive beamforming for multi-microphone audio processing," in 2019 IEEE Automatic Speech Recognition and Understanding Workshop (ASRU). IEEE, 2019.
Y. Luo, Z. Chen, and T. Yoshioka, "Dual-path RNN: efficient long sequence modeling for time-domain single-channel speech separation," arXiv preprint arXiv:1910.06379, 2019.
Y. Luo, Z. Chen, J. R. Hershey, J. Le Roux, and N. Mesgarani, "Deep clustering and conventional networks for music separation: Stronger together," in Acoustics, Speech and Signal Processing (ICASSP), 2017 IEEE International Conference on. IEEE, 2017, pp. 61-65.
Yang, X., Wang, K., and Shamma, S.A. (1992). Auditory representations of acoustic signals. IEEE Trans. Inf. Theory 38, 824-839.
Yi Luo and Nima Mesgarani, "Tasnet: Surpassing ideal time frequency masking for speech separation," arXiv preprint arXiv:1809.07454, 2018.
Schwartz O, Simoncelli EP. 2001. Natural sound statistics and divisive normalization in the auditory system. Advances in Neural Information Processing Systems 166-172.

(56) References Cited

OTHER PUBLICATIONS

Schwartz, O., Gannot, S., Habets, E.A.P., 2017. Multispeaker lcmv beamformer and post-filter for source separation and noise reduction. IEEE/ACM Trans. Audio Speech Lang. Process. 25 (5), 940-951. doi: 10.1109/TASLP.2017.2655258.

Schonwiesner, M., and Zatorre, R.J. (2009). Spectro-temporal modulation transfer function of single voxels in the human auditory cortex measured with high-resolution fMRI. Proc. Natl. Acad. Sci. 106, 14611-14616.

Selinker, L. Interlanguage. IRAL—Int. Rev. Appl. Linguist. Lang. Teach. 10, 209-232 (1972).

Shamma, S. (2008). On the emergence and awareness of auditory objects. PLoS Biol. 6, e155.

Shamma, S.A., Elhilali, M., and Micheyl, C. (2011). Temporal coherence and attention in auditory scene analysis. Trends Neurosci. 34, 114-123.

Shannon CE. 1948. A Mathematical Theory of Communication. Bell System Technical Journal 27:379-423. DOI: https://doi.org/10.1002/j.1538-7305.1948.tb01338.x.

Shany O, Singer N, Gold BP, Jacoby N, Tarrasch R, Hendler T, Granot R. 2019. Surprise-related activation in the nucleus accumbens interacts with music-induced pleasantness. Social Cognitive and Affective Neuroscience 14: 459-470. DOI: https://doi.org/10.1093/scan/nsz019, PMID: 30892654.

Sharon Gannot, Emmanuel Vincent, Shmulik Markovich-Golan, and Alexey Ozerov, "A consolidated perspective on multimicrophone speech enhancement and source separation," IEEE/ACM Transactions on Audio, Speech, and Language Processing, vol. 25, No. 4, pp. 692-730, 2017.

Sharpee T, Rust NC, Bialek W. 2004. Analyzing neural responses to natural signals: maximally informative dimensions. Neural Computation 16:223-250. DOI: https://doi.org/10.1162/089976604322742010, PMID: 15006095.

Shinn-Cunningham, B.G. (2008). Object-based auditory and visual attention. Trends Cogn. Sci. 12, 182-186.

Simon Doclo, Sharon Gannot, Marc Moonen, and Ann Spriet, "Acoustic beamforming for hearing aid applications," Handbook on array processing and sensor networks, pp. 269-302, 2010.

Skerritt-Davis B, Elhilali M. 2018. Detecting change in stochastic sound sequences. PLOS Computational Biology 14: e1006162. DOI: https://doi.org/10.1371/journal.pcbi.1006162, PMID: 29813049.

Slee, S.J., and David, S.V. (2015). Rapid task-related plasticity of spectrotemporal receptive fields in the auditory midbrain. J. Neurosci. 35, 13090-13102.

Somers B, Verschueren E, Francart T. 2019. Neural tracking of the speech envelope in cochlear implant users. Journal of Neural Engineering 16:16003. DOI: https://doi.org/10.1088/1741-2552/aae6b9.

Song, J. & Iverson, P. Listening effort during speech perception enhances auditory and lexical processing for non-native listeners and accents. Cognition 179, 163-170 (2018).

Southwell R, Chait M. 2018. Enhanced deviant responses in patterned relative to random sound sequences. Cortex 109:92-103. DOI: https://doi.org/10.1016/j.cortex.2018.08.032, PMID: 30312781.

Srivastava N, Hinton G, Krizhevsky A, Sutskever I, Salakhutdinov R. 2014. Dropout: a simple way to prevent neural networks from overfitting. Journal of Machine Learning Research : JMLR 15:1929-1958.

Steinhauer, K. & Drury, J. E. On the early left-anterior negativity (ELAN) in syntax studies. Brain Lang. 120, 135-162 (2012).

Steinschneider M, Fishman YI, Arezzo JC. 2008. Spectrotemporal analysis of evoked and induced electroencephalographic responses in primary auditory cortex (A1) of the awake monkey. Cerebral Cortex 18: 610-625. DOI: https://doi.org/10.1093/cercor/bhm094, PMID: 17586604.

Steinschneider M. 2013. Phonemic Representations and Categories. In: Cohen Y. E, Popper A. N, Fay R. R (Eds). Neural Correlates of Auditory Cognition. Springer. p. 151-191. DOI: https://doi.org/10.1007/978-1-4614-2350-8_6.

Steinschneider, M., Nourski, K. V, Kawasaki, H., Oya, H., Brugge, J.F., and Howard, M.A. (2011). Intracranial study of speech-elicited activity on the human posterolateral superior temporal gyrus. Cereb. Cortex 21, 2332-2347.

Steinschneider, M., Nourski, K.V., and Fishman, Y.I. (2013). Representation of speech in human auditory cortex: is it special? Hear. Res. 305, 57-73.

Steinschneider, M., Nourski, K.V., Rhone, A.E., Kawasaki, H., Oya, H., and Howard, M.A., 3rd (2014). Differential activation of human core, non-core and auditory-related cortex during speech categorization tasks as revealed by intracranial recordings. Front. Neurosci. 8, 240.

Steinschneider, M., Volkov, I.O., Fishman, Y.I., Oya, H., Arezzo, J.C., and Howard III, M.A. Intracortical responses in human and monkey primary auditory cortex support a temporal processing mechanism for encoding of the voice onset time phonetic parameter. Cereb. Cortex 15, 170-186. (2005).

Storkel HL, Rogers MA. 2000. The effect of probabilistic phonotactics on lexical acquistion. Clinical Linguistics & Phonetics 14:407-425. DOI: https://doi.org/10.1080/026992000415859.

Strang G. 1993. Introduction to Linear Algebra. Wellesley-Cambridge Press.

Strauß A, Kotz SA, Obleser J. 2013. Narrowed Expectancies under Degraded Speech: Revisiting the N400. Journal of Cognitive Neuroscience 25:1383-1395. DOI: https://doi.org/10.1162/jocn_a_00389.

T. C. Yin, "Neural mechanisms of encoding binaural localization cues in the auditory brainstem," in Integrative functions in the mammalian auditory pathway. Springer, 2002, pp. 99-159.

T. Lotter and P. Vary, "Dual-channel speech enhancement by superdirective beamforming," EURASIP Journal on Advances in Signal Processing, vol. 2006, No. 1, p. 063297, 2006.

T. Rohdenburg, V. Hohmann, and B. Kollmeier, "Robustness analysis of binaural hearing aid beamformer algorithms by means of objective perceptual quality measures," in 2007 IEEE Workshop on Applications of Signal Processing to Audio and Acoustics. IEEE, 2007, pp. 315-318.

T. von Neumann, K. Kinoshita, M. Delcroix, S. Araki, T. Nakatani, and R. Haeb-Umbach, "All-neural online source separation, counting, and diarization for meeting analysis," in Acoustics, Speech and Signal Processing (ICASSP), 2019 IEEE International Conference on. IEEE, 2019, pp. 91-95.

T. Yoshioka, I. Abramovski, C. Aksoylar, Z. Chen, M. David, D. Dimitriadis, Y. Gong, I. Gurvich, X. Huang, Y. Huang et al., "Advances in online audio-visual meeting transcription," arXiv preprint arXiv:1912.04979, 2019.

Talavage, T.M., Sereno, M.I., Melcher, J.R., Ledden, P.J., Rosen, B.R., and Dale, A.M. (2004). Tonotopic organization in human auditory cortex revealed by progressions of frequency sensitivity. J. Neurophysiol.

Tara N Sainath, Ron J Weiss, Kevin W Wilson, Arun Narayanan, Michiel Bacchiani, et al., "Speaker location and microphone spacing invariant acoustic modeling from raw multichannel waveforms," in Automatic Speech Recognition and Understanding (ASRU), 2015 IEEE Workshop on. IEEE, 2015, pp. 30-36.

Tara N. Sainath, Ron J. Weiss, Kevin W. Wilson, Bo Li, Arun Narayanan, Ehsan Variani, Michiel Bacchiani, Izhak Shafran, Andrew Senior, Kean Chin, et al., "Multichannel signal processing with deep neural networks for automatic speech recognition," IEEE/ACM Transactions on Audio, Speech, and Language Processing (TASLP), vol. 25, No. 5, pp. 965-979, 2017.

Teki, S., Barascud, N., Picard, S., Payne, C., Griffiths, T.D., and Chait, M. (2016). Neural correlates of auditory figure-ground segregation based on temporal coherence. Cereb. Cortex 26, 3669-3680.

Temperley D, Clercq Tde. 2013. Statistical analysis of harmony and melody in rock music. Journal of New Music Research 42:187-204. DOI: https://doi.org/10.1080/09298215.2013.788039.

Temperley D. 2008. A probabilistic model of melody perception. Cognitive Science: A Multidisciplinary Journal 32:418-444. DOI: https://doi.org/10.1080/03640210701864089, PMID: 21635341.

(56) References Cited

OTHER PUBLICATIONS

Thakur, C.S., Wang, R.M., Afshar, S., Hamilton, T.J., Tapson, J.C., Shamma, S.A., and van Schaik, A. (2015). Sound stream segregation: a neuromorphic approach to solve the "cocktail party problem" in real-time. Front. Neurosci. 9, 309.

Theunissen FE, Sen K, Doupe AJ. 2000. Spectral-temporal receptive fields of nonlinear auditory neurons obtained using natural sounds. The Journal of Neuroscience 20:2315-2331. DOI: https://doi.org/10.1523/JNEUROSCI.20-06-02315.2000, PMID: 10704507.

Theunissen, F., and Miller, J.P. (1995). Temporal encoding in nervous systems: a rigorous definition. J. Comput. Neurosci. 2, 149-162.

Theunissen, F.E., David, S. V, Singh, N.C., Hsu, A., Vinje, W.E., and Gallant, J.L. (2001a). Estimating spatio-temporal receptive fields of auditory and visual neurons from their responses to natural stimuli. Network 12, 289-316.

Theunissen, F.E., Sen, K., and Doupe, A.J. (2000). Spectral-temporal receptive fields of nonlinear auditory neurons obtained using natural sounds. J. Neurosci. 20, 2315-2331.

Thomas, J.M., Huber, E., Stecker, G.C., Boynton, G.M., Saenz, M., and Fine, I. (2015). Population receptive field estimates of human auditory cortex. Neuroimage 105, 428-439.

Tibshirani R, Walther G, Hastie T. 2001. Estimating the number of clusters in a data set via the gap statistic. Journal of the Royal Statistical Society: Series B 63:411-423. DOI: https://doi.org/10.1111/1467-9868.00293.

Tillmann B, Bharucha JJ, Bigand E. 2000. Implicit learning of tonality: a self-organizing approach. Psychological Review 107:885-913. DOI: https://doi.org/10.1037/0033-295X.107.4.885, PMID: 11089410.

Todorovic A, de Lange FP. 2012. Repetition suppression and expectation suppression are dissociable in time in early auditory evoked fields. Journal of Neuroscience 32:13389-13395. DOI: https://doi.org/10.1523/JNEUROSCI.2227-12.2012, PMID: 23015429.

Todorovic A, van Ede F, Maris E, de Lange FP. 2011. Prior expectation mediates neural adaptation to repeated sounds in the auditory cortex: an MEG study. Journal of Neuroscience 31:9118-9123. DOI: https://doi.org/10.1523/JNEUROSCI.1425-11.2011, PMID: 21697363.

Toro JM, Sinnett S, Soto-Faraco S. 2005. Speech segmentation by statistical learning depends on attention. Cognition 97:B25-B34. DOI: https://doi.org/10.1016/j.cognition.2005.01.006.

* cited by examiner

SYSTEMS AND METHODS FOR BRAIN-INFORMED SPEECH SEPARATION

CROSS-REFERENCE TO RELATED APPLICATIONS

This application is a continuation application of, and claims priority to, International Application No. PCT/US2021/053560, entitled "SYSTEMS AND METHODS FOR BRAIN-INFORMED SPEECH SEPARATION," and filed Oct. 5, 2021, which in turn claims priority to, and the benefit of, U.S. Provisional Application No. 63/087,636, entitled "BRAIN-INFORMED SPEECH SEPARATION (BISS) FOR ENHANCEMENT OF TARGET SPEAKER IN MULTI-TALKER SPEECH PERCEPTION" and filed Oct. 5, 2020, the content of which is incorporated herein by reference in its entirety.

STATEMENT REGARDING FEDERALLY SPONSORED RESEARCH

This invention was made with government support under DC014279 awarded by the National Institutes of Health. The government has certain rights in the invention.

BACKGROUND

Hearing-impaired people often struggle to follow the speech stream of an individual talker in noisy environments. Recent studies show that the brain tracks attended speech and that the attended talker can be decoded from neural data on a single-trial level. Current speech separation solutions implemented in hearing aid devices include solutions based on array signal processing and beamforming. However, because the microphones are typically placed on the hearing aid itself, the efficacy of the beamforming solutions is limited by the small number of microphones and insufficient distance between them which is restricted by the size of the subject's head.

SUMMARY

The present disclosure proposed a novel approach for speech enhancement and speaker separation (e.g., to mitigate the cocktail party problem) through a brain-informed speech separation (BISS) technique that combines speaker separation and speaker selection steps of auditory attention decoding (or AAD, which is a framework that uses neural signals to decode and enhance a target speaker in multi-talker speech perception). That is, information about the attended speech, as decoded from the subject's brain, is directly used to perform speech separation in the front-end. The approaches described herein use a deep learning model that uses neural data to extract the clean audio signal that a listener is attending to from a multi-talker speech mixture. This proposed framework can be applied successfully to the decoded output from either invasive intracranial electroencephalography (iEEG) or non-invasive electroencephalography (EEG) recordings from hearing-impaired subjects. It also results in improved speech separation, even in scenes with background noise. By jointly performing speech extraction and neural decoding, the neural signal directly guides a robust single channel speech extraction process/algorithm which is implemented using a neural network model. This method alleviates the need for a prior assumption of the number of speakers in the mixed audio and reduces the source distortion and computational load by extracting the target speaker from the scene. For these reasons, BISS represents a superior candidate for the implementation of a closed-loop, real-time, neuro-steered hearing aid (HA) which naturally adapts to different auditory scenes and number of competing sources.

Accordingly, in some variations, a speech separation method is provided that includes obtaining, by a device, a combined sound signal for signals combined from multiple sound sources in an area in which a person is located, obtaining, by the device, neural signals for the person, with the neural signals being indicative of one or more target sound sources, from the multiple sound sources, the person is attentive to, determining a separation filter based, at least in part, on the neural signals obtained for the person, and applying, by the device, the separation filter to a representation of the combined sound signal to derive a resultant separated signal representation associated with sound from the one or more target sound sources the person is attentive to.

Embodiments of the method may include at least some of the features described in the present disclosure, including one or more of the following features.

Determining the separation filter may include determining based on the neural signals an estimate of an attended sound signal corresponding to the one or more target sound sources the person is attentive to, and generating the separation filter based, at least in part, on the determined estimate of the attended sound signal.

Determining the estimate of the attended sound signal may include determining, using a learning process, an estimate sound envelope for the one or more target sound sources the person is attentive to.

Determining the separation filter may include deriving, using a trained learning model, a time-frequency mask that is applied to a time-frequency representation of the combined sound signal.

Deriving the time-frequency mask may include deriving the time-frequency mask based on a representation of an estimated target envelope for the one or more target sound sources the person is attentive to, determined based on the neural signals obtained for the person, and based on a representation for the combined sound signal.

The method may further include determining the estimated target envelope for the one or more target sound sources based on a machine-learned mapping process, implemented using regularized linear regression, applied to the obtained neural signals to produce the estimated target envelope.

Deriving the time-frequency mask may include combining the representation of the estimated target envelope with the representation for the combined sound signal to produce a fused signal.

Combining the representation of the estimated target envelope with the representation of the combined sound signal may include transforming the representation of the estimated target envelope into a 3D tensor estimated target envelope representation, transforming the representation of combined signal into a 3D tensor combined signal representation, and concatenating the 3D tensor estimated target envelope representation to the 3D tensor combined signal representation to generate a 3D tensor fused signal representation.

The method may further include processing the fused signal with a network of convolutional blocks arranged in a stack, wherein each of the convolutional blocks is configured to apply a convolutional process to input received from a respective preceding block, and to generate output comprising a sum of the input from the respective preceding block and output of the respective convolutional process applied to the input received from the preceding block.

The each of the convolutional blocks may include one or more convolution operators, at least one of the one or more convolution operators processing input data according to a dilation factor that is based on position of the respective convolutional block within the stack comprising the respective convolutional block.

The each of the convolutional blocks may further include one or more ReLU non-linearity elements.

The method may further include determining a time-frequency representation for the combined sound signal, including applying a short-time Fourier transform to the combined sound signal to generate a transformed combined sound signal, and compressing the transformed combined sound signal to generate a compressed spectrogram representation of the combined sound signal.

Applying the separation filter to the representation of the combined sound signal may include applying the time-frequency mask to the compressed spectrogram representation of the combined sound signal to generate an output spectrogram, and inverting the output spectrogram into a time-domain audio output signal.

The combined sound signal may include sound components corresponding to multiple receiving channels, and determining the separation filter may include applying multiple encoders to the sound components corresponding to the multiple receiving channels, with each of the encoders applied to each of the sound components, combining, for each of the multiple receiving channels, output components of the multiple encoders associated with respective ones of the multiple receiving channels, and deriving estimated separation functions based on the combined output components for each of the multiple receiving channels, each of the derived estimated separation functions configured to separate the combined output components for each of the multiple receiving channels into separated sound components associated with groups of the multiple sound sources.

The multiple receiving channels may include a first and second binaural receiving channels.

The combined sound signal may include representations of sound components corresponding to multiple receiving channels, and determining the separation filter may include applying multiple encoders to the representations of sound components corresponding to the multiple receiving channels, with each of the encoders applied to each of the sound components, determining spatial features based on the sounds components corresponding to the multiple receiving channels, combining the determined spatial features with output components of the multiple encoders associated with respective ones of the multiple receiving channels, to produce a combined encoded output, deriving, based on the combined encoded output, estimated separation functions, and separating, using the estimated separation functions, the combined encoded output into separated sound components associated with groups of the multiple sound sources.

Determining the spatial features may include determining one or more of, for example, interaural level difference (ILD) information, and/or interaural time difference (ITD) information.

The method may further include combining the separated sound components with the representations of the sound components to produce a combined enhanced signal representation, and deriving estimated separation functions based on the combined enhanced signal representation to separate the combined enhanced signal representation into separated enhanced sound components associated with the groups of the multiple sound sources.

The method may further include determining, based on the separated sound components, direction of arrival of the separated sound components.

Obtaining the neural signals for the person may include measuring the neural signals according to one or more of, for example, invasive intracranial electroencephalography (iEEG) recordings, non-invasive electroencephalography (EEG) recordings, functional near-infrared spectroscopy (fNIRS) recordings, and/or recordings captured with subdural or brain-implanted electrodes.

In some variations, a system is provided that includes at least one microphone to obtain a combined sound signal for signals combined from multiple sound sources in an area in which a person is located, one or more neural sensors to obtain neural signals for the person, with the neural signals being indicative of one or more target sound sources, from the multiple sound sources, the person is attentive to, and a controller in communication with the at least one microphone and the one or more neural sensors. The controller is configured to determine a separation filter based, at least in part, on the neural signals obtained for the person, and apply the separation filter to a representation of the combined sound signal to derive a resultant separated signal representation associated with sound from the one or more target sound sources the person is attentive to.

In some variations, non-transitory computer readable media is provided that includes computer instructions executable on a processor-based device to obtain a combined sound signal for signals combined from multiple sound sources in an area in which a person is located, obtain neural signals for the person, with the neural signals being indicative of one or more target sound sources, from the multiple sound sources, the person is attentive to, determine a separation filter based, at least in part, on the neural signals obtained for the person, and apply the separation filter to a representation of the combined sound signal to derive a resultant separated signal representation associated with sound from the one or more target sound sources the person is attentive to.

Embodiments of the system and the computer readable media may include at least some of the features described in the present disclosure, including at least some of the features described above in relation to the method.

Other features and advantages of the invention are apparent from the following description, and from the claims.

BRIEF DESCRIPTION OF THE DRAWINGS

These and other aspects will now be described in detail with reference to the following drawings.

Like reference symbols in the various drawings indicate like elements.

DESCRIPTION

Figure 1:
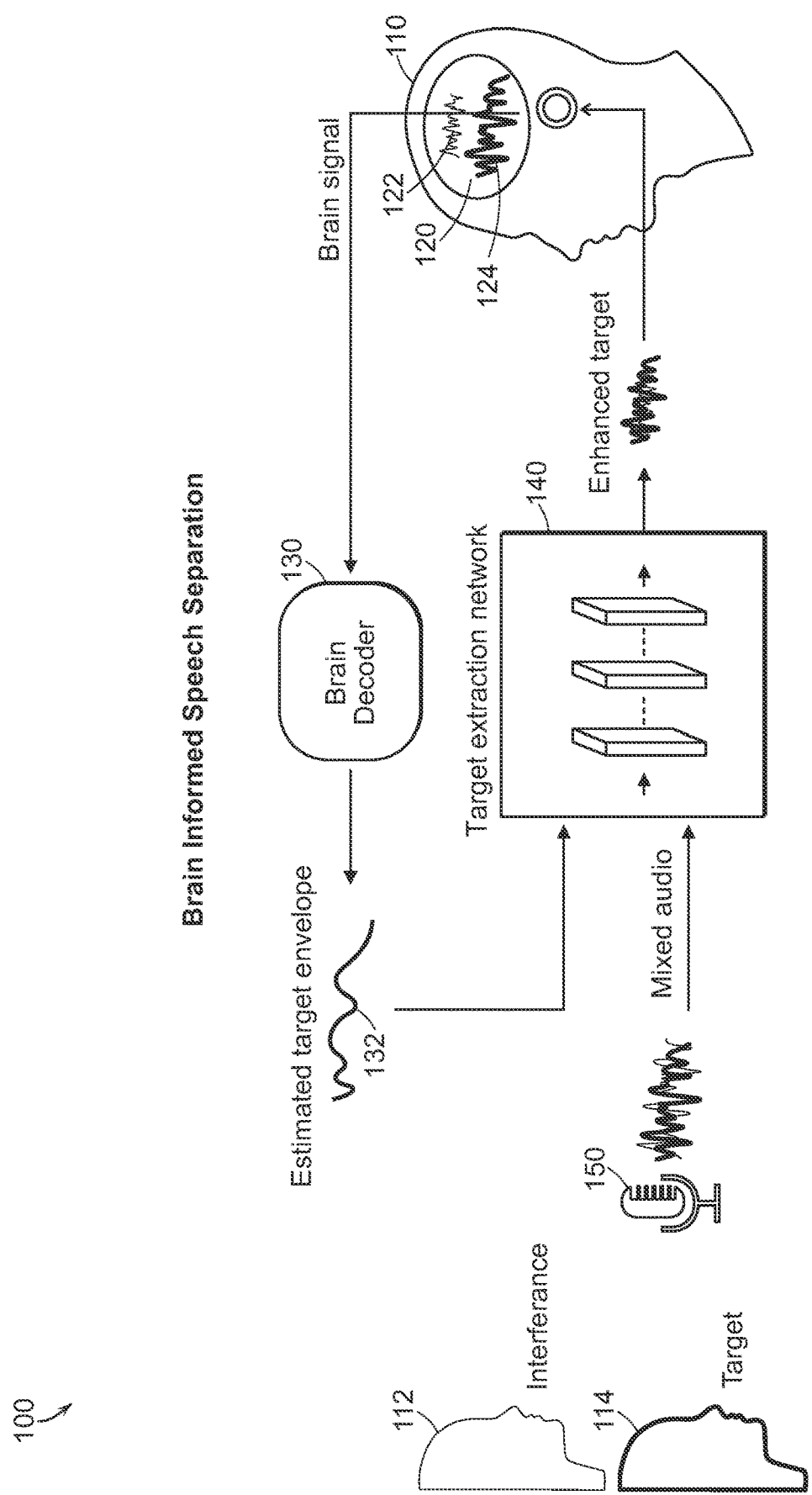
FIG. 1 is a schematic diagram of an example system implementing brain-informed speech separation.

Disclosed are systems, methods, and other implementations (including hardware, software, and hybrid hardware/software implementations) directed to a framework called brain-informed speech separation (BISS) in which the information about the attended speech, as decoded from a subject's (listener's) brain, is directly used to perform speech separation in the front-end. Thus, in such embodiments, the neural signals are used in the filtering process applied to a received combined audio signal to obtain the audio signal of interest. Briefly, an AAD system (also referred to as a "brain decoder") decodes an envelope (or some other representation) of the attended speech using brain signals (EEG or iEEG signals), and uses the decoded envelope (or "hint") to incorporate that information into a deep-learning-based speech separation process/algorithm to provide information regarding which of the signals in the acoustic scene has to be extracted from a multi-talker speech mixture. The extracted (enhanced) speech of the desired speaker is then amplified and delivered to the user.

The framework described herein can be applied successfully to the decoded output from either invasive intracranial electroencephalography (iEEG) or non-invasive electroencephalography (EEG) recordings from hearing-impaired subjects. Other ways to measure neural signals may be used, including functional near-infrared spectroscopy (fNIRS) recordings, recordings through subdural electrodes, etc. The framework results in improved speech separation, even in scenes with background noise. The generalization capability of the system renders it a perfect candidate for neuro-steered hearing-assistive devices.

Accordingly, embodiments of the approaches described herein include a system that comprises at least one microphone to obtain a combined sound signal for signals combined from multiple sound sources in an area in which a person is located, one or more neural sensors to obtain neural signals for the person, with the neural signals being indicative of one or more target sound sources, from the multiple sound sources, the person is attentive to, and a controller in communication to the at least one microphone and the one or more neural sensors. The controller is configured to determine a separation filter based, at least in part, on the neural signals obtained for the person, and apply the separation filter to a representation of the combined sound signal to derive a resultant separated signal representation associated with sound from the one or more target sound sources the person is attentive to. In some examples, the controller configured to determine the separation filter is configured to derive, using a trained learning model implemented on the controller, a time-frequency mask that is applied to a time-frequency representation of the combined sound signal. In some embodiments, determining the separation filter may include determining based on the neural signals an estimate of an attended sound signal corresponding to the one or more target sound sources the person is attentive to, and generating the separation filter based, at least in part, on the determined estimate of the attended sound signal.

Thus, with reference to FIG. 1, a schematic diagram of an example system 100 implementing brain-informed speech separation is shown. As illustrated, a subject 110 attends to one (in this example, the lower target 114, in FIG. 1) out of two (or more) simultaneous talkers (the target 114 and a talker 112). The system includes one or more neural sensors (schematically represented as neural sensor 120) that are deployed on a surface of a hearing device secured to the head of the subject 110, or implemented as separate electrode in wired or wireless communication with the hearing device, to obtain neural signals 122 and 124 for the subject 110, based on which speech filtering (separation and/or other processing to extract the sound signal, from a mixed sound signal) is performed.

The measured neural signals 122 and 124 are delivered to a brain decoder 130 (which may be implemented using a processor-based device housed on the hearing device). In some examples, the decoding process is configured to estimate (e.g., via machine learning implementation) the envelope of the attended speech based on recorded brain signals. The recorded brains signal may include invasive intracranial electroencephalography (iEEG) recordings, non-invasive electroencephalography (EEG) recordings, functional near-infrared spectroscopy (fNIRS) recordings, recordings through brain-implanted and/or subdural electrodes, and/or other types of neural signal recordings acquired through appropriate sensors (e.g., electrodes secured externally to the subject, or implanted within the body of the subject, for example within the brain). The resultant output 132 of the brain decoder 130 (be it an estimated target envelope, or some other output signal representative of the sound signal that the subject is attending to or focusing on) is provided to a target extraction network 140, which may implement a speech separation neural network model, that receives, in addition to the decoded output signal 132, a speech mixture signal 152 generated by a microphone 150 (which may also be housed or deployed on the hearing device carried by, or secured to, the subject 110). The two inputs received, namely, the speech mixture, and the output signal 132 (a "hint" input, such as the decoded envelope) are used by the model implemented by the target extraction network 140 to separate and enhance the speech of the attended talker. The output of the model is the enhanced speech which is fed to the hearing aid device of the subject in this closed-loop setup. Thus, in the approaches of FIG. 1, the filtering processing performed by the target extraction network 140 is an adaptable process that adaptively configures the filtering (e.g., by generating a mask applied to a representation based on the combined audio signal) realized by the target extraction network 140 based on inputs that include the actual mixed signal that is to be separated, and the neural signals measured from the subject that provide information on who the subject 110 is attending to.

As noted, in some embodiments, the brain decoder 130 is configured to reconstruct the speech envelope of the attended speaker from the raw data collected by EEG or iEEG sensors. The decoder 130 may be implemented a spatio-temporal filter that maps the neural recordings (e.g., 122 and 124) to a speech envelope. The mapping may be based on a stimulus reconstruction method which may be learned, for example, using regularized linear regression or a deep neural network model. For both the EEG and iEEG data, a subject-specific linear decoder can be trained on S-T data and used to reconstruct speech envelopes on the M-T data. This approach avoids potential bias introduced by training and testing on the M-T data. For the iEEG data, only the outputs of a subset of electrodes may be used as input to the decoder. In such embodiments, electrode selection can be conducted via a statistical analysis to determine whether a specific electrode is significantly more responsive to speech compared to silence.

In some examples, a speaker-independent speech separation neural network model (such as that implemented by the network 140) is trained using the brain signals of the listener to guide the separation. As illustrated in FIG. 1, the two inputs to the speech separation neural network are the noisy audio mixture and the hint represented by the attended speech envelope decoded from the listener's neural signals. The audio mixture y(t) generally includes the sum of the attended speaker $s_a(t)$ and all undesired sound sources $s_u(t)$ (other speakers and noise) such that $y(t)=s_a(t)+s_u(t)$, where t represents the time index. The time-frequency representation of this mixture Y(l,f) can be obtained by taking the short-time Fourier transform (STFT) of y(t), specifically:

$$Y(l,f)=\text{STFT}(y(t))=S_a(l,f)+S_u(l,f),$$

where l and f are time and frequency bin indices, respectively.

The complex mixture spectrogram $Y \in \mathbb{C}^{F \times L}$ may be compressed, e.g., by a factor of 0.3, to reduce the dynamic range of the spectrogram; thus: $Y_c=(Y)^{0.3}$ where $Y_c \in \mathbb{C}^{F \times L}$.

A Separation model implemented by the target extraction network 140 is realized, in some embodiments, based on an architecture that only uses 2D convolution structure (but possibly may use other configurations and structures, including a long-short term memory (LSTM) network). The use of a 2D convolution architecture is motivated because processing is performed in the time-frequency domain. The use of convolutional layers allows to decrease the number of parameters in the model and to control the temporal length of the receptive fields. The general architecture includes a computational block that fuses a hint signal (as will be described in greater detail below in relation to FIG. 2A) with the mixture audio, followed by a processing arrangement that includes stacks of convolutional layers (each of which may be identical in its architecture and number of parameters, thereby making the architecture modular). A final block applies the estimated complex mask M to the compressed input mixture spectrogram $Y^c$ and inverts the estimated output spectrogram to the time domain.

Although the example embodiments presented herein uses a trainable 2D convolutional architecture to produce separations filter (e.g., masks) to extract an attendant speaker's speech, or to determine a decoded brain signal representative of a brain-informed signal to be combined with the mixed sound signal, other types/configurations of artificial neural networks may be used in place of the embodiment described herein. Other types of learning engines that may be used to generate separation filters or decoded brain signal representations include, for example, recurrent neural network (RNN)-based implementations, which may be based on an LSTM encoder-decoder architecture. Additional learning network configurations include other types of convolutional neural networks (CNN), and feed-forward neural networks. Feed-forward networks include one or more layers of nodes ("neurons" or "learning elements") with connections to one or more portions of the input data. In a feedforward network, the connectivity of the inputs and layers of nodes is such that input data and intermediate data propagate in a forward direction towards the network's output. Unlike an RNN configuration, there are typically no feedback loops or cycles in the configuration/structure of the feed-forward network. Convolutional layers allow a network to efficiently learn features by applying the same learned transformation(s) to subsections of the data. Other examples of learning engine approaches/architectures that may be used include generating an auto-encoder and using a dense layer of the network to correlate with probability for a future event through a support vector machine, constructing a regression or classification neural network model that predicts a specific output from data (based on training reflective of correlation between similar records and the output that is to be predicted), etc.

Neural networks and/or other types of machine-learning implementations can be implemented on any computing platform, including computing platforms that include one or more microprocessors, microcontrollers, and/or digital signal processors that provide processing functionality, as well as other computation and control functionality. The computing platform can include one or more CPU's, one or more graphics processing units (GPU's, such as NVIDIA GPU's, which can be programmed according to, for example, a CUDA C platform), and may also include special purpose logic circuitry, e.g., an FPGA (field programmable gate array), an ASIC (application-specific integrated circuit), a DSP processor, an accelerated processing unit (APU), an application processor, customized dedicated circuitry, etc., to implement, at least in part, the processes and functionality for the neural networks, processes, and methods described herein. The computing platforms used to implement the neural networks typically also include memory for storing data and software instructions for executing programmed functionality within the device. Generally speaking, a computer accessible storage medium may include any non-transitory storage media accessible by a computer during use to provide instructions and/or data to the computer. For example, a computer accessible storage medium may include storage media such as magnetic or optical disks and semiconductor (solid-state) memories, DRAM, SRAM, etc.

The various learning processes implemented through use of the neural networks described herein may be configured or programmed using, for example, TensorFlow (an open-source software library used for machine learning applications such as neural networks). Other programming platforms that can be employed include keras (an open-source neural network library) building blocks, NumPy (an open-source programming library useful for realizing modules to process arrays) building blocks, etc.

As noted, the separation of the mixed/combined signal is based, in part, on use of a hint signal, generated from measured neural signals, to produce a signal that represents speech of the attended speaker. The hint input (e.g., the decoded envelope 132 representing what the subject is perceiving) may come from the temporal envelope of the clean speech of the attended speaker: $h(t)=|s_a(t)|^{0.3}$, where the absolute value of the waveform, $s_a(t)$ is calculated and, in some embodiments, compressed by a factor of 0.3. During the training of the neural network model, the envelope is calculated from the clean audio signal.

In order to extract the speech of the desired speaker from the mixture, the speech separation neural network model is trained to estimate a complex valued mask $M \in \mathbb{C}^{F \times L}$. The estimated mask M is applied pointwise to the input STFT $Y_c$, namely:

$$\hat{S}_d^c = M \odot Y^c.$$

The resulting estimated spectrogram is decompressed and inverted to the time domain to obtain an enhanced version of the desired speech $\hat{s}_d$. Specifically, the decompression operation produces $\hat{S}_d = \hat{S}_d^{c})^3$, and the inversion operation produces In some example implementations, audio signals processing may include capturing (through a single microphone, or through multiple microphones) audio segments (e.g., 4 seconds segments) that are transformed to the frequency domain with a STFT using a window size of 512 and a step size of 125. The choice of the length in time (4 seconds) is arbitrary and different segment lengths may be used instead. The choice of 125 samples is appropriate for some applications because the audio sampling rate is 8 kHz and an output rate of 64 Hz, that matches the envelope sampling rate, may be desired. Because of the Hermitian property of the Fourier transform on real data, only the positive frequencies of the transformed signal can be kept, thus obtaining as input a 3D tensor of size 2×257×257. For the output mask, a complex-valued mask may be used instead of a real-valued magnitude mask. Using a real-valued magnitude mask forces the use of the noisy phase when inverting the estimated separated spectrogram to the time domain, and it has been shown that using the compressed complex mask gives better results. Because, in some embodiments, a complex STFT with overlapping windows is used, there exists an ideal complex mask that perfectly isolates the desired source from the mixture. Unfortunately, the mask values can be arbitrarily high and unbounded, and this poses a problem for the training process. For this reason, a hyperbolic tangent compression may be used that limits the output mask values to the range [−1, 1]. In such situations, only an approximation of the ideal mask can be computed.

Figure 2A:
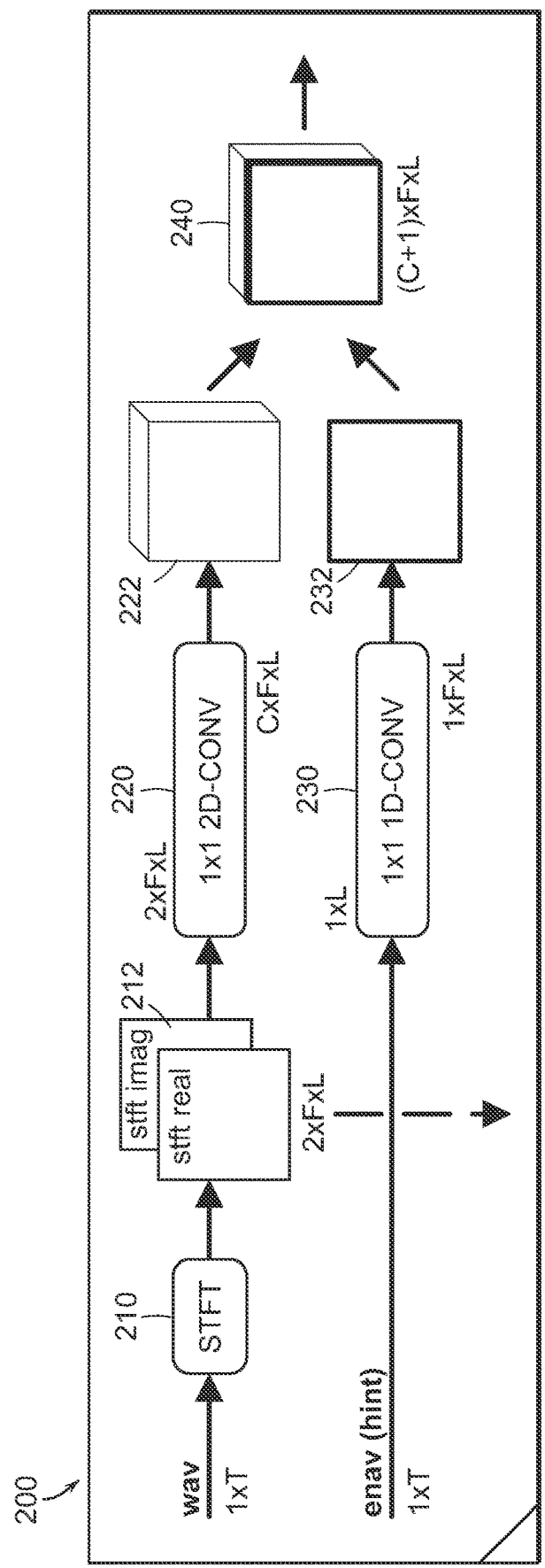
FIG. 2A is a block diagram of a hint fusion module that may be included in a target extraction network shown in FIG. 1.

As noted, to incorporate information about neural signals into the mask-generating process, a hint fusion procedure is implemented (and may be part of the target extraction network 140 of FIG. 1). With reference to FIG. 2A, a block diagram of a hint fusion module 200 is depicted. The hint fusion procedure includes two different processing steps that allow concatenating the audio waveform of the mixture $Y^c$ with the desired speech envelope H(l). First, the mixture waveform is transformed in the frequency domain by means of an STFT unit 210. The real and imaginary parts are then concatenated along a new axis effectively producing a 3D tensor 212 of size 2×F×L. A 1×1 2D convolution with C feature maps is then applied (at block 220) to obtain a 3D tensor 222 of shape C×F×L. Similarly, the desired (attended) speech envelope is processed with a 1×1 1D convolution unit 230 and expanded to become a 3D tensor 232 of shape 1×F×L. Finally, the two tensors are concatenated along the feature map axis to obtain a 3D tensor 240 of shape (C+1)×F×L.

Figure 2B:
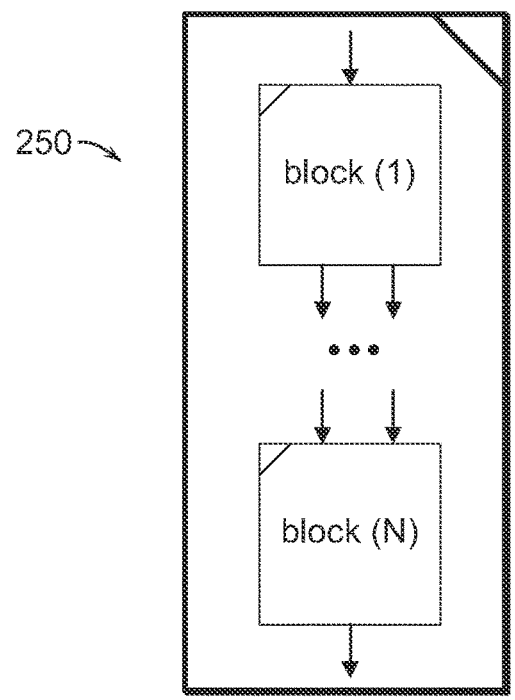
FIG. 2B is a schematic diagram of a partial arrangement of stacks which forms part of the example target extraction network shown in FIG. 1.
Figure 2C:
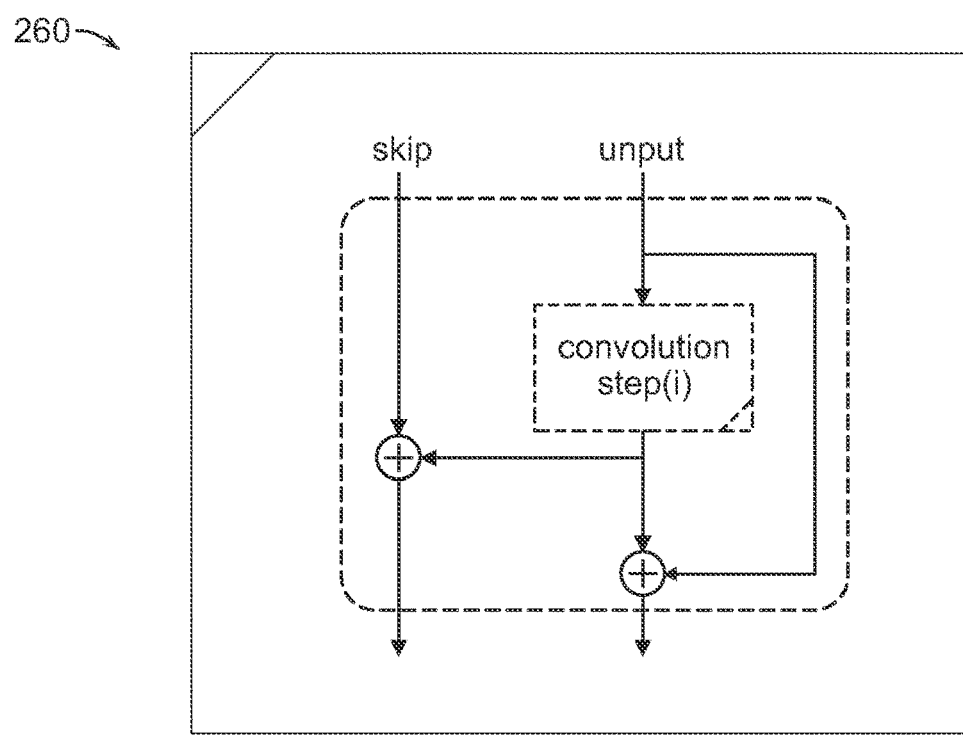
FIG. 2C is a diagram of an example block that may be used in any of the stacks shown in FIG. 2B.

The network realizing the hint fusion module 200 also includes an arrangement 250 of S stacks (illustrated in FIG. 2B), with each stack (individually indexed as stack s) being composed of multiple blocks. An example block 260 (each block is index block i) used in a stack is provided in FIG. 2C. The block 260 receives two inputs: the skip connection (r) from the input and the output (o) of a previous block. The skip connection is the sum of the input plus the output of each convolutional step, while the output of the block is the output of the convolution summed with the residual connection of the current input. This implementation can be expressed as:

$$p_i^s = c_i^s + s_{i-1}^s, \text{ and}$$

$$o_i^s = o_{i-1}^s + c_i^s$$

Figure 2D:
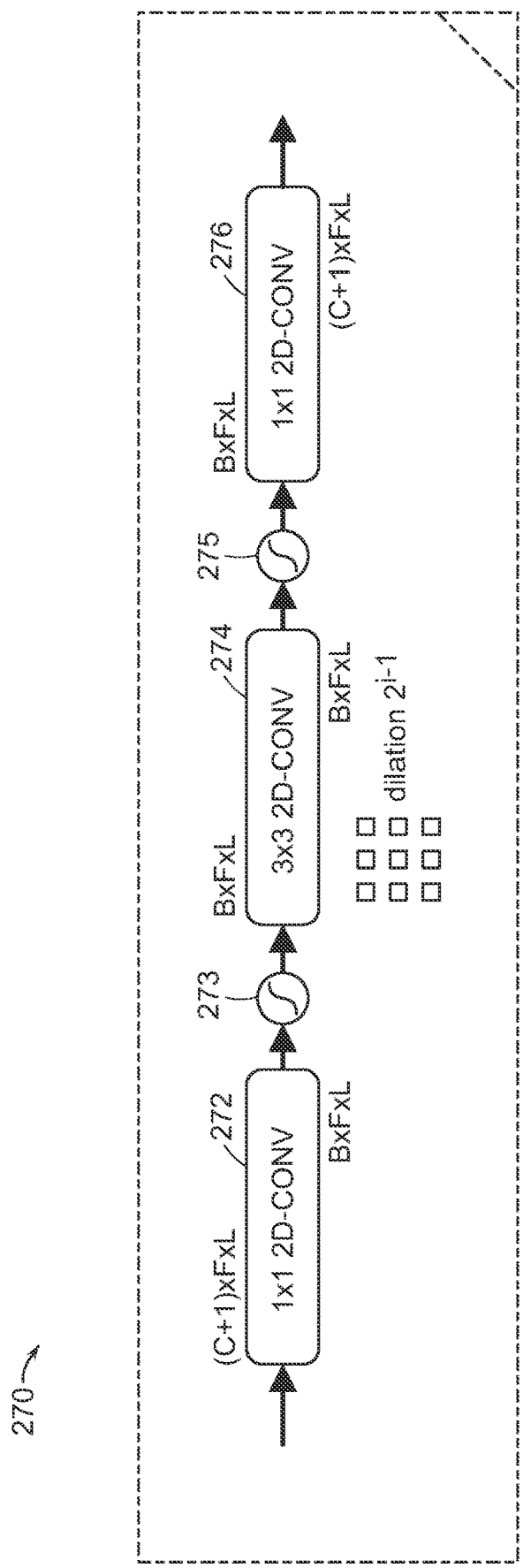
FIG. 2D is a schematic diagram of an example configuration of the convolutional step/operator included is provided in FIG. 2C.

Generally, the skip input to the first block in a stack is a matrix of zeros, while the output of the last block, and thus of the stack, is the skip path. Each block contains a convolutional step unit, such as the example convolutional step unit 270 depicted in FIG. 2D. In some embodiments, the convolutional step unit for all blocks (of all stacks) may have the same architecture, but may vary by having different dilation factors that are defined by the block index i. For example, the dilation factor for block i may be set to 2'. In some embodiments, the convolutional step has three parts: a) a 1×1 convolution operator 272 followed by a ReLU non-linearity element 273, b) a 3×3 convolution element 274 with a dilation factor i followed by a ReLU non-linearity 275, and c) another 1×1 convolution element 276. These parts can be represented as follows:

$$b_{i,1}^s = \text{ReLU}(\text{conv}_{i,1}(o_{i-1})),$$

$$b_{i,2}^s = \text{ReLU}(\text{conv}_{i,2}(b_{i,1}^s)), \text{ and}$$

$$p_{i,3}^s = c_i^s = \text{conv}_{i,3}(b_{i,2}^s)).$$

The final convolutional step is utilized to get back the same input shape which allows the residual and skip connections to be added. This step increases the total number of parameters in the network without increasing the receptive field. Batch norm is applied at the end of the convolutional step. Overall, the receptive field (RF) in both frequency and time can be calculated as follows:

$$RF(N, S, k) = k + S\sum_{i=0}^{N}(k-1)2^i$$

where k is the kernel size.

Square kernels are used so the receptive fields have the same dimension in both the frequency and time domain in terms of bins, but are different in terms of meaning and measure.

Figure 2E:
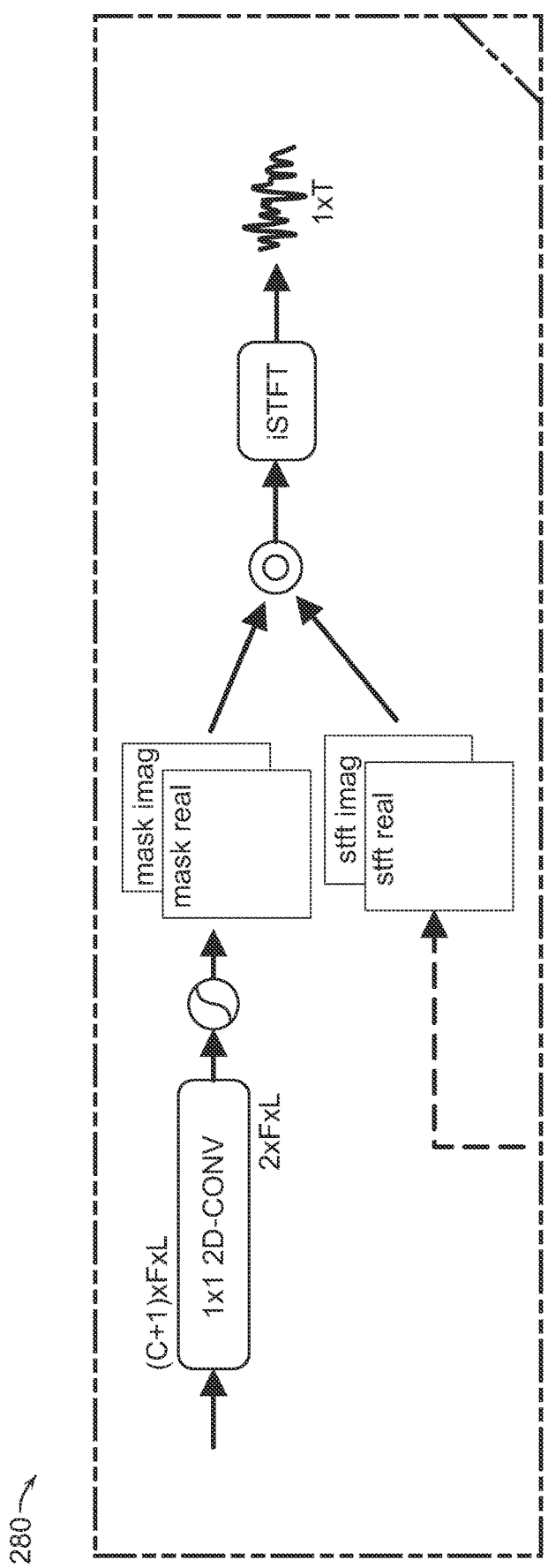
FIG. 2E is a schematic diagram of an example mask-generation module that is part of the example target extraction network shown in FIG. 1.

The last step of the extraction network implementation/process is the mask-generation module 280, schematically depicted in FIG. 2E. As shown, the output of the last stack, $o_N^s$ is reshaped by a 1×1 convolution from a shape of (C+1)×F×L to a shape of 2×F×L, where the first dimension represents the concatenation of real and imaginary parts. In some embodiments, the mask, M, is obtained by first applying a hyperbolic tangent to the output of that convolution and then summing real and imaginary parts properly. Thus:

$\tilde{M}=\tanh(\text{conv}(o_N^s))$, and $M=\tilde{M}(0,:,:)+i\tilde{M}(1,:,:)$ where the operation (j, :, :) represents the tensor slicing that selects only the $j^{th}$ element in the first tensor dimension, and i represents the imaginary unit. The generated mask M is then applied to the combined audio signal to separate the desired speech. The model is relatively simple and has very few parameters (e.g., around half a million for the implementations used to obtain the results discussed in greater detail below).

Thus, the BISS system illustrated in FIG. 1 uses a representation (e.g., a decoded speech envelope) of neural signals corresponding to speech information perceived by a subject as the informed input to the speech separation network. Ideally, a neural network could be trained with the brain-decoded envelopes. However, the EEG and iEEG data collected for attention decoding typically amounts to less than one hour of data for each subject. This amount of data is not enough to train an accurate speech separation model which has millions of parameters (such a model would require in the order of tens of hours of recorded speech). To address this problem, the training of the speech separation model is decoupled from the training of the brain decoder model. The separately trained models are then fused at test time. In order to do this, the speech separation model is trained with the ground truth speech envelope extracted from the audio using same envelope calculation as those used for attention decoding model. This guarantees that the attention decoding model will provide an envelope which is most correlated with the desired speech to extract. In the tested implementations discussed herein, most of the EEG data was collected in Denmark using Danish audiobooks, while the iEEG data was collected in New York using English audiobooks. Since a single model is being proposed to extract desired speech from either EEG or iEEG, the training dataset for the speech separation model includes a mixture of English and Danish utterances (i.e., the model is not language-specific). The English materials used for training included the Wall Street Journal (WSJ) utterances in the WSJ-mix2 dataset often used for source separation benchmarks. The Danish utterances were taken from Danish audiobooks used for the EEG study. It is to be noted that the training data is completely separated from the testing data, i.e., the audio tracks used in the attention decoding for both EEG and iEEG are not part of the training dataset. The overall training dataset used for the tested implementations comprised 22 hours of data. Mixed sentences were created on-the-fly at training time as a data augmentation method to effectively increase the amount of data used in training.

When estimating the frequency-domain masks for speech separation, the mean squared error (MSE) is generally used as the cost function. However, the estimated masks are usually smeared, limiting the separation quality. In the approaches described herein, a time-domain optimization method is proposed for use with a frequency domain solution by embedding both the STFT and iSTFT procedure into the training pipeline. Because these operations are differentiable, the normal backpropagation algorithm can be used to train the model. An example of a cost function used to optimize the model is SI-SDR. Optimizing the SI-SDR has shown very good results in time domain separation due to the fact that the model directly optimizes the measure which is used to evaluate its performance. The SI-SDR metric (SDR for simplicity) can be calculated directly from the time domain signals as follows:

$$s_{target} = \frac{\langle \hat{s}_d, s_d\rangle s_d}{\|s_d\|^2},$$

$e_{noise} = \hat{s}_d - s_{target}$, and $$SI-SDR = 10\log_{10}\frac{\|s_{target}\|^2}{\|e_{noise}\|^2}.$$

In some embodiments, the neural network model can be trained, for example, using the Adam optimizer with default settings and early stopping as a regularizer.

In some implementations, the speech separation model may be trained using a clean speech envelope calculated directly from the audio ground truth. However, the envelope estimated from either EEG or iEEG is not a perfect reconstruction of the original envelope. Generally, decoded envelopes have a Pearson's correlation r of <0.3 for EEG data and about 0.6 for iEEG data. Because of this, it is important that the speech separation model is robust to a noisy hint envelope. The distribution of the noise in the decoding process is therefore estimated, and the variance of this noise is extracted for both EEG and iEEG data. The noise has a Gaussian distribution with µ=0 and $\sigma_{iEEG}$=0.2 for iEEG, and $\sigma_{EEG}$=0.3 for EEG signals. After training the speech separation model with clean speech envelopes, the training is continued using a curriculum training technique in which the amount of noise injected into the training data increases continuously for a number of epochs. This training schedule has been shown to be optimal for training a model that is robust to a large range of input signal-to-noise ratio (SNR)s. A schedule may be used in which the a of the added noise increases in steps of 0.05 from [0.05, 0.6].

Figure 3:
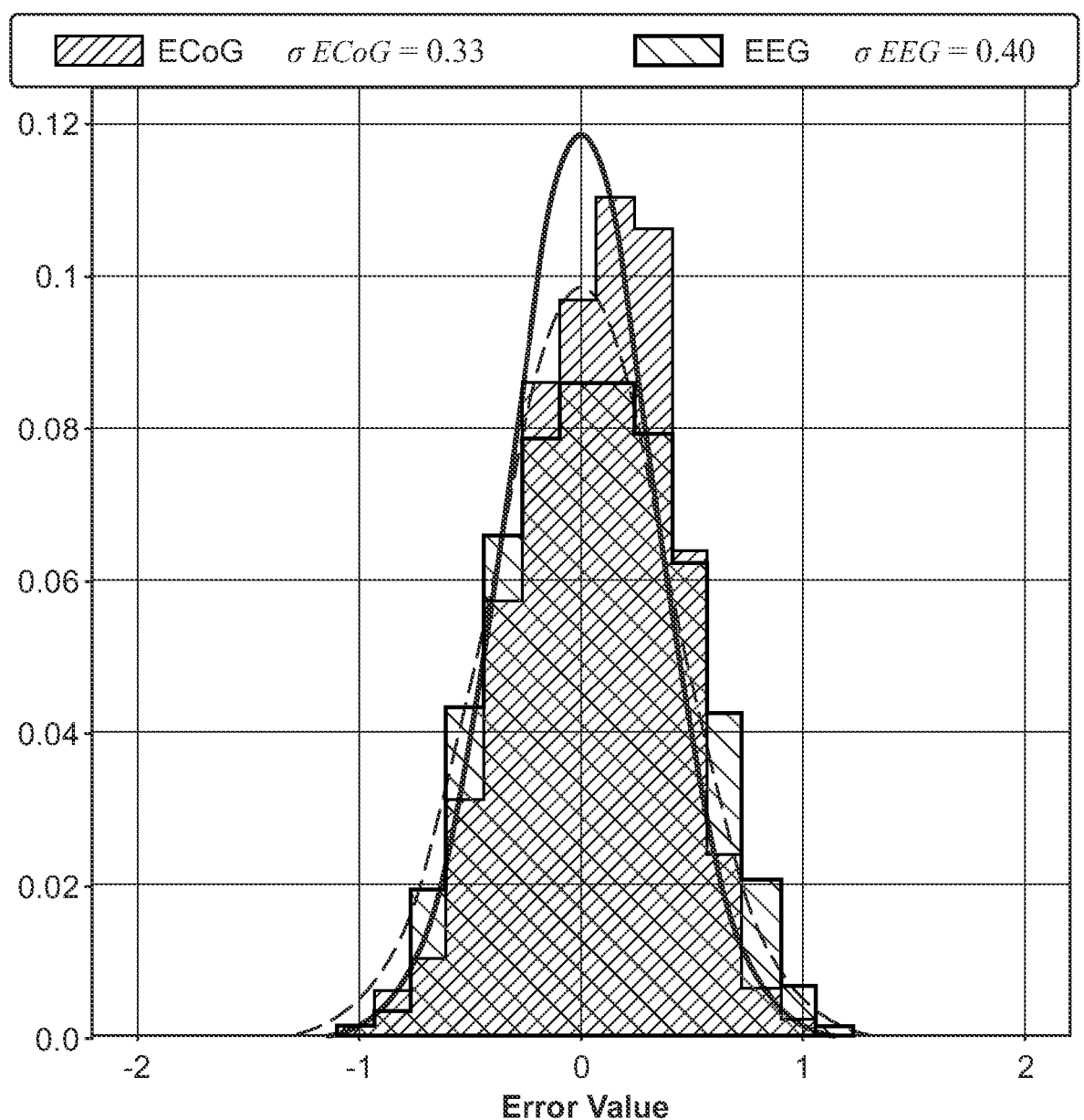
FIG. 3 includes a graph showing distribution of errors between the reconstructed attended envelope and the original attended envelopes for both EEG and iEEG.

To make the speech separation model more robust to the degraded quality of the envelope reconstructed from the brain signals, a curriculum learning training scheme may be employed. This scheme includes increasing progressively, over training epochs, the difficulty of the task by introducing progressively more noise in the training. In order for this scheme to be effective, one needs to ensure that the noise injected during training is of the same distribution of the noise that will be present at test time. In some examples, an empirical distribution of the noise in the reconstructed envelope is used, which is represented by the error between the original envelope and the envelope reconstructed with AAD. This is exactly the noise that the network will be faced with when trained with the clean envelope and tested with the (noisy) reconstructed one. FIG. 3 includes a graph 300 showing the distribution of errors between the reconstructed attended envelope and the original attended envelope for both EEG and iEEG. As expected, the distribution of error for the EEG reconstruction has a bigger standard deviation with respect to the standard deviation of the iEEG reconstruction error.

Figure 4:
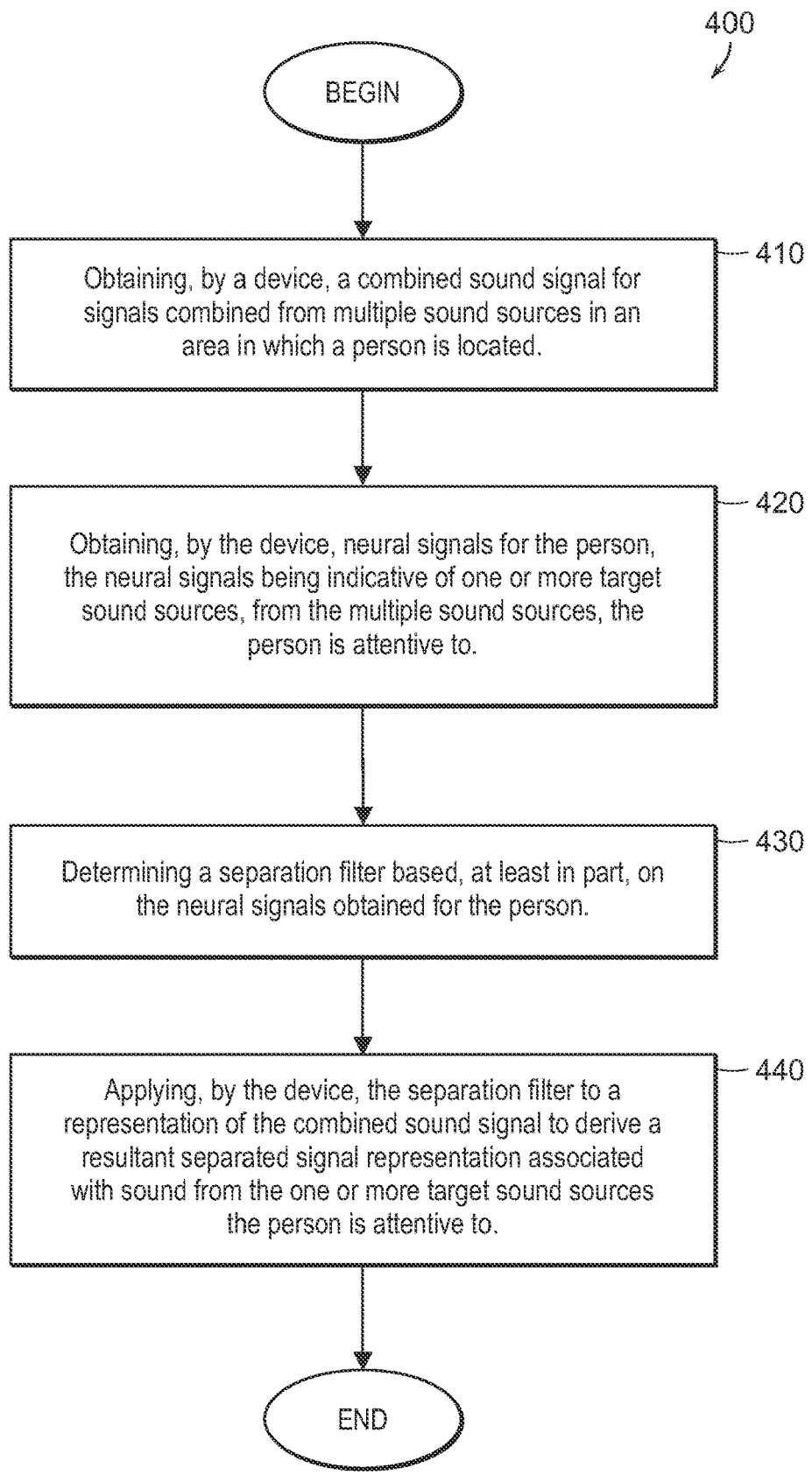
FIG. 4 is a flowchart of an example sound separation procedure.

With reference next to FIG. 4, a flowchart of an example sound separation procedure 400 is shown. The procedure 400 includes obtaining 410, by a device (e.g., one or more microphones of a hearing device), a combined sound signal for signals combined from multiple sound sources in an area in which a person is located. The procedure 400 further includes obtaining 420, by the device, neural signals for the person, with the neural signals being indicative of one or more target sound sources, from the multiple sound sources, the person is attentive to. In some embodiments, obtaining the neural signals for the person may include measuring the neural signals according to one or more of, for example, invasive intracranial electroencephalography (iEEG) recordings, non-invasive electroencephalography (EEG) recordings, functional near-infrared spectroscopy (fNIRS) recordings, and/or recordings through subdural or brain-implanted electrodes.

With continued reference to FIG. 4, the procedure 400 further includes determining 430 a separation filter based, at least in part, on the neural signals obtained for the person, and applying 440, by the device, the separation filter to a representation of the combined sound signal to derive a resultant separated signal representation associated with sound from the one or more target sound sources the person is attentive to. Thus, in the approaches described herein, the neural signals are used not merely to indicate the target speaker the listener is focusing on, but to actually synthesize separation filters (e.g., in the form of a mask) that are applied to a combined signal (e.g., combining multiple signals captured, for example, by a single microphone or multiple microphones).

In some examples, determining the separation filter may include determining based on the neural signals an estimate of an attended sound signal corresponding to the one or more target sound sources the person is attentive to, and generating the separation filter based, at least in part, on the determined estimate of the attended sound signal. Determining the estimate of the attended sound signal may include determining, using a learning process, an estimate sound envelope for the one or more target sound sources the person is attentive to.

In some embodiments, determining the separation filter may include deriving, using a trained learning model (e.g., implemented on the target extraction network 140), a time-frequency mask (mask M discussed herein) that is applied to a time-frequency representation of the combined sound signal. As noted, the separation filter (in this example, a mask) may be based on the measured neural signals which indicate which speaker (or group of speakers) the subject is attentive to. An example of a derived representation of which speaker the listener is attentive to is to use a signal envelope, derived from neural signals (e.g., through a learning model) for the speech signal that the listener is focusing on. In such embodiments, deriving the time-frequency mask may include deriving the time-frequency mask based on a representation of an estimated target envelope for the one or more target sound sources the person is attentive to (with the estimated target envelope determined based on the neural signals obtained for the person), and further based on a representation for the combined sound signal. It is to be noted that other representations associated with the target speaker may be used. In examples in which the separation mask is derived based on an estimated target envelope, the procedure 400 may further include determining the estimated target envelope for the one or more target sound sources based on a machine-learned mapping process, implemented using regularized linear regression, applied to the obtained neural signals to produce the estimated target envelope.

In some examples, deriving the time-frequency mask may include combining the representation of the estimated target envelope with the representation for the combined sound signal to produce a fused signal. For example, combining the representation of the estimated target envelope with the representation of the combined sound signal may include (as also depicted in FIG. 2A) transforming the representation of the estimated target envelope into a 3D tensor estimated target envelope representation transforming the representation of combined signal into a 3D tensor combined signal representation, and concatenating the 3D tensor estimated target envelope representation to the 3D tensor combined signal representation to generate a 3D tensor fused signal representation.

In some embodiments, the procedure 400 may further include processing the fused signal with a network of convolutional blocks arranged in one or more stacks, with each of the convolutional blocks being configured to apply a convolutional process to input received from a respective preceding block, and to generate output comprising a sum of the input from the respective preceding block and output of the respective convolutional process applied to the input received from the preceding block. The each of the convolutional blocks may include, in such embodiments, one or more convolution operators, with at least one of the one or more convolution operators processing input data according to a dilation factor that is based on position of the respective convolutional block within the stack comprising the respective convolutional block. Each such convolutional block may further include one or more rectified linear activation function (ReLU) non-linearity elements. An example of a configuration of a convolutional block is provided in FIG. 2D. Alternative ways to combine (integrate or fuse) a signal representation of the sound signal (e.g., speech signal) attended to by the listener and the combined sound signals from multiple sources, in order to produce a composite signal combining sound information and attended speaker information, may be implemented (including by interlacing samples of the fused signals, performing a filtering operation to produce a composite signal, etc.)

In some embodiments, the procedure 400 may further include determining a time-frequency representation for the combined sound signal. This may include applying a short-time Fourier transform to the combined sound signal to generate a transformed combined sound signal, and compressing the transformed combined sound signal to generate a compressed spectrogram representation of the combined sound signal. In such embodiments, applying the separation filter to the representation of the combined sound signal may include applying the time-frequency mask to the compressed spectrogram representation of the combined sound signal to generate an output spectrogram, and inverting the output spectrogram into a time-domain audio output signal.

The brain-information speech separation approaches described herein were implemented and tested to obtain further details about the performance and features of the brain-information speech separation approaches. Brain recordings data used in the implementations described herein included EEG recordings from 22 normal hearing (NH) and 22 age-matched hearing-impaired (HI) subjects (NH: mean age 63.0±7.1; HI: mean age 66.4±7.0). HI listeners had a sloping high-frequency hearing-loss typical of presbycusis (age-related hearing loss). In 48 trials of ≈50 sec each, sub-jects listened to stories read by either a single talker (S-T) (16 trials), or multi talkers (M-T) (one male, one female, 32 trials). In the M-T trials, the two speech streams were presented at the same loudness level to allow unbiased attention decoding. The two competing speech streams were spatially separated at ±90° using non-individualized head-related transfer functions. On each trial, the subjects were cued to attend to either the male or female talker and the attended target was randomized across the experiment. After each trial, the subjects responded to 4 comprehension questions related to the content of the attended speech. Both NH and HI listeners had accurate speech comprehension for both the single-talker (NH: 93.3%, HI: 92.3% correct) and two-talker conditions (NH: 91.9%, HI: 89.8% correct). Despite high accuracy on speech comprehension questions, listening difficulty ratings revealed that the HI listeners rated the two-talker condition as being significantly more difficult than NH listeners did. The recordings data also included iEEG data collected from three subjects undergoing clinical treatment for epilepsy at the North Shore University Hospital, New York. These subjects were implanted with high-density subdural electrode arrays covering their language dominant (left) temporal lobe with coverage over the superior temporal gyrus (STG). Similar to the EEG experiments, the subjects participated in two experiments, a S-T experiment and a M-T experiment. In both experiments, the subjects listened to stories read by two speakers, one male speaker and one female speaker. In the S-T experiment, the subjects listened to each speaker separately, and in the M-T experiment the subjects listened to the two speakers talking concurrently with no spatial separation, i.e., the voices were rendered by a single loudspeaker placed in front of the subject. During the M-T experiment, each subject was presented with 11 minutes and 37 seconds of audio, making the S-T experiment twice as long. In the M-T experiment the audio was separated into 4 blocks (segments). In each block, the subject was asked to focus their attention on only one speaker. At the end of each block the subjects were asked to repeat the last sentence of the attended speaker to ensure that they were indeed paying attention to the correct speaker. All the subjects performed the task with high accuracy and were able to report the sentence with an average accuracy of 90.5% (S1, 94%; S2, 87%; and S3, 90%). The envelope of the high-gamma power was used at each site as a measure of neural activation.

Figure 5:
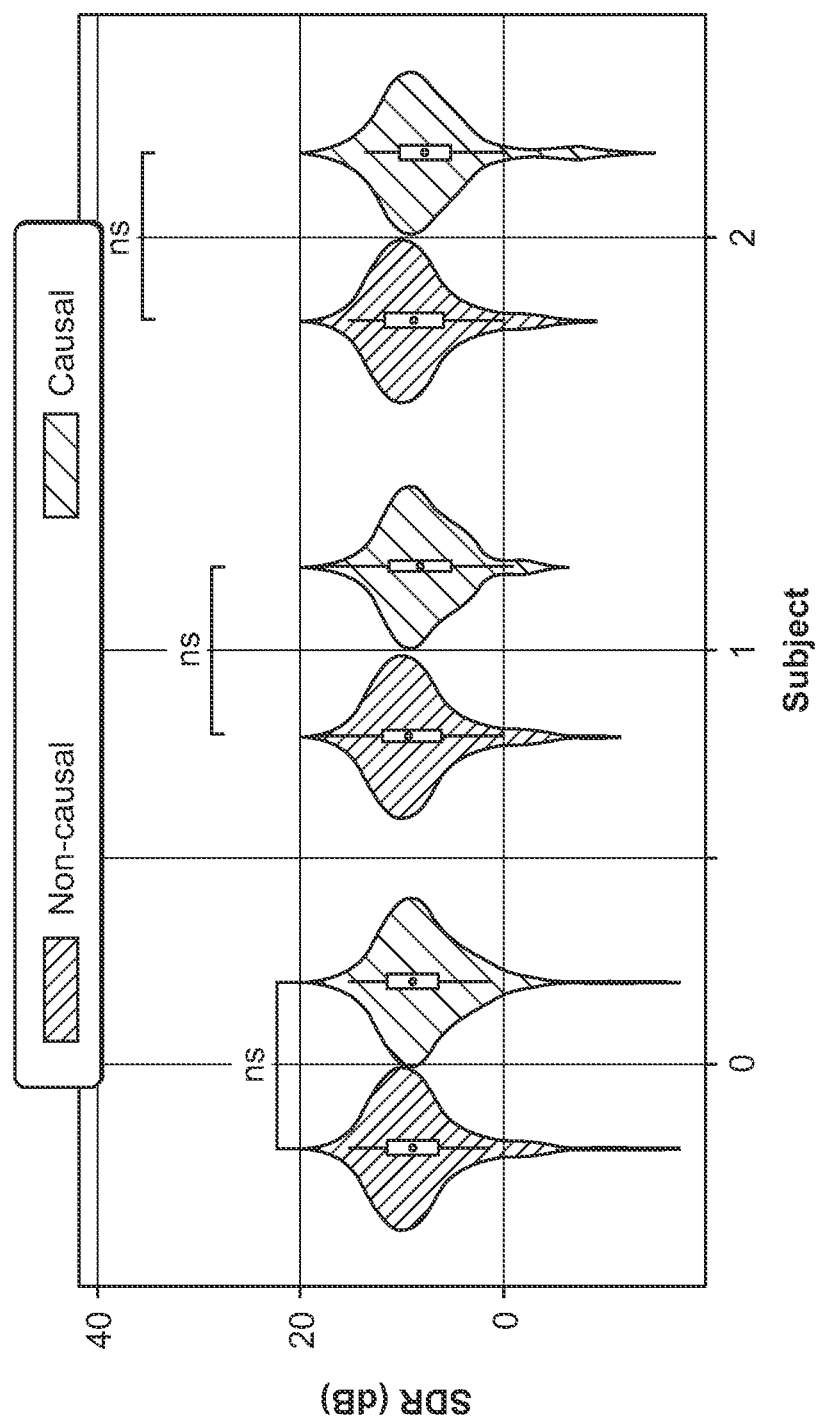
FIG. 5 includes violin plots of scale-invariant signal-to-distortion ratio (SI-SDR) illustrating SDR improvement from noisy speech mixture achieved from testing a brain-informed speech separation implementation.

The BISS model described herein was tested on the iEEG recordings. FIG. 5 provides violin plots of scale-invariant signal-to-distortion ratio (SI-SDR) illustrating SDR improvement from the noisy speech mixture achieved from testing the BISS model with 4 s utterances. The results for the BISS framework were obtained for each subject separately, using envelopes decoded from the iEEG data, and for model settings of causal and non-causal (significance is indicated by ns if p>0.05 using Mann-Whitney U test). Each subject was tested on a set of 69 non-overlapping mixtures of two speakers for which SDR improvements using the clean reference signal were determined. The results presented in FIG. 5 show a comparable performance across all subjects. Subject 0 was the best with an SDR improvement of 9.5 dB; nevertheless, no significant difference between the scores of the three subjects was found. Additionally, the performance of causal and non-causal settings was similar for all subjects. One possible explanation for the similarity of performance across subjects is the noise training procedure in causal and non-causal settings. To test this hypothesis, the performances of the causal and non-causal models were tested using the noisy envelopes, like those used in training, rather than the neurally decoded envelopes provided as the hint (the brain information). The test showed a decrease in performances gap between the causal and non-causal settings from an initial 1 dB to 0.5 dB. This shows that while there might be a large difference in performance between causal and non-causal settings when using clean envelopes, this difference decreases when using noisy envelopes. This can explain the lack of significance between causal and non-causal settings in FIG. 5.

Figure 6:
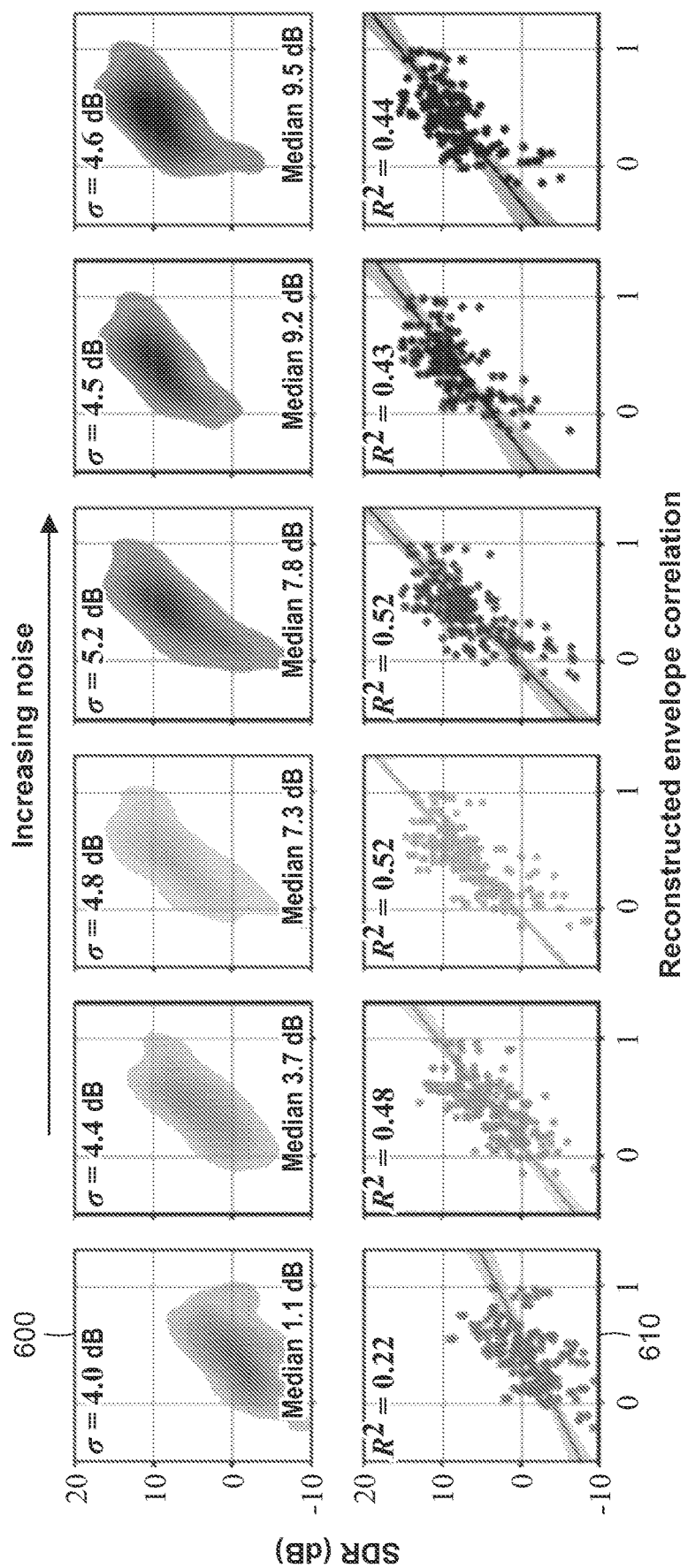
FIG. 6 includes graphs showing envelope reconstruction results for iEEG recordings for an individual as a function of noise variance during curriculum training.

Next, the effects of the noise curriculum training on the model performance when utilizing neural data were investigated. FIG. 6 includes graphs showing envelope reconstruction results for iEEG recordings for an individual as a function of noise variance during curriculum training. The x-axis for the graphs indicates the $r_{diff}=r_{attended}-r_{unattended}$ values, while the y-axis indicates SDR improvement in dB. The results shown in FIG. 6 were determined for 69 utterances when the individual (Subject 0) was attending to the male speaker in the mixture. The top panels of FIG. 6 show a density plot (using kernel density estimate with Gaussian kernels) of the utterances together with their median value, while the bottom panels show every single utterance plotted separately and a linear fit (using linear regression) of these points. The shaded areas in the plot represents the 95% confidence interval of the regression. Furthermore, the panels, going from left to right, show results from increasing the a of the noise during training (from σ=0.0 to σ=0.5 with steps of 0.1). The leftmost panels (e.g., graphs 600 and 610) show the results for the model without any noise training while the other panels show the effect of increasing the noise during training. The top panels additionally show that the median value shifts from below 0 dB, which indicates a failed separation, to above 9 dB, which indicates a very good separation. The bottom panels show that, independent of the noise level used in the training, there is a clear correlation between $r_{diff}$ and the output SDR improvement. This indicates that the quality of the separation is linearly dependent on the quality of the envelope reconstruction in terms of Pearson's r value.

Figure 7:
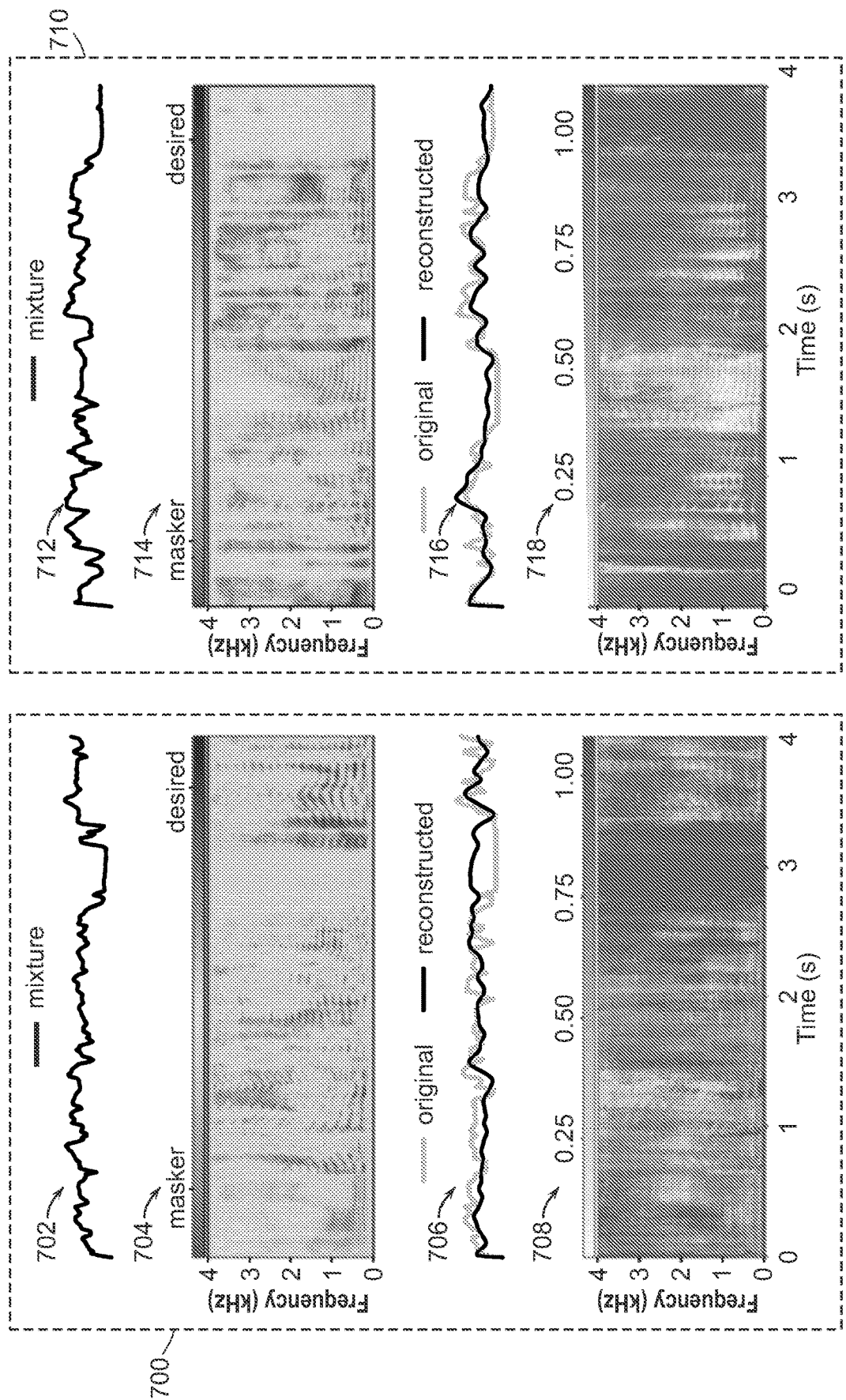
FIG. 7 includes two sets of graphs illustrating two examples of mask estimation test cases and results.

Next, the effect of using different Pearson's r values on the estimated mask M was explored. In particular, the investigation studied how the masks differ when an utterance with high correlation is compared to an utterance with low correlation. For example, FIG. 7 provides two sets of graphs, 700 and 710, illustrating two examples of mask estimation test cases and results. Each of the sets of graphs includes, from top to bottom, a mixture envelope (702 and 712), a mixture spectrogram (704 and 714) with desired speaker highlighted in darker shade, original and reconstructed desired speech envelopes (706 and 716), and mask estimated by the model based on the decoded envelope (708 and 718). The first example mask estimation test case (corresponding to the set 700) is of a failed mask with a correlation of −0.13 and an SDR improvement of −10.4 dB. The second example mask estimation test case (corresponding to the set 710) is of a successful mask with an r value of 0.69 and an SDR of 9.2 dB. The example mask estimation results of FIG. 7 shows that the mask for the failed utterance (corresponding to the set 700) has fewer sharp edges around the harmonics of the desired speech, while for the successful utterance (corresponding to the set 710) the mask is sharp around every part of the desired speech, and especially sharp around the harmonics. This is true even at smaller time scales where the sharpness of the mask tightly follows the correlation of the reconstructed envelope.

Figure 8:
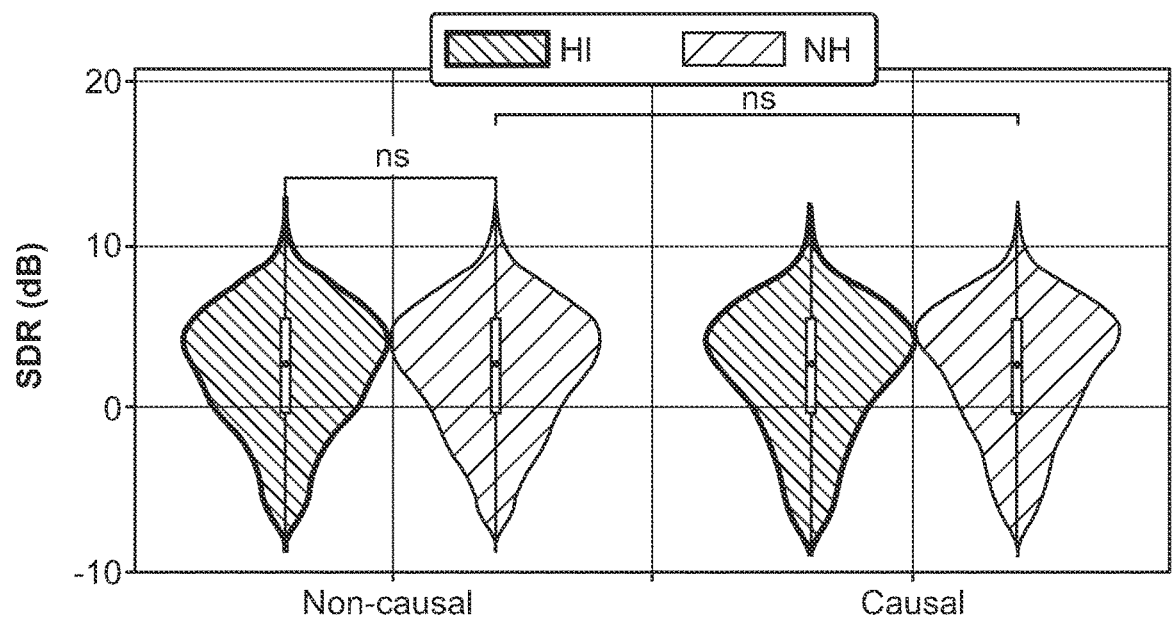
FIG. 8 includes a graph showing separation result performance of a brain-informed speech separation implementation for causal versus non-causal settings for the two subject groups.

Turning next to the testing performed on the EEG dataset, the investigation focused mainly on the differences between NH (21 subjects) and HI (20 subjects) groups. For each subject, the performance was tested on 128 non-overlapping segments of 4 seconds. As in the iEEG case, the investigation looked at the differences in performance for the model under causal and non-causal settings. FIG. 8 shows the separation result performance of a brain-informed speech separation implementation for causal versus non-causal settings for the two subject groups. In the figure, the y-axis shows the separation quality in terms of SDR improvement in dB. Significance is indicated by ns if p>0.05 using Mann-Whitney U test.

Figure 9:
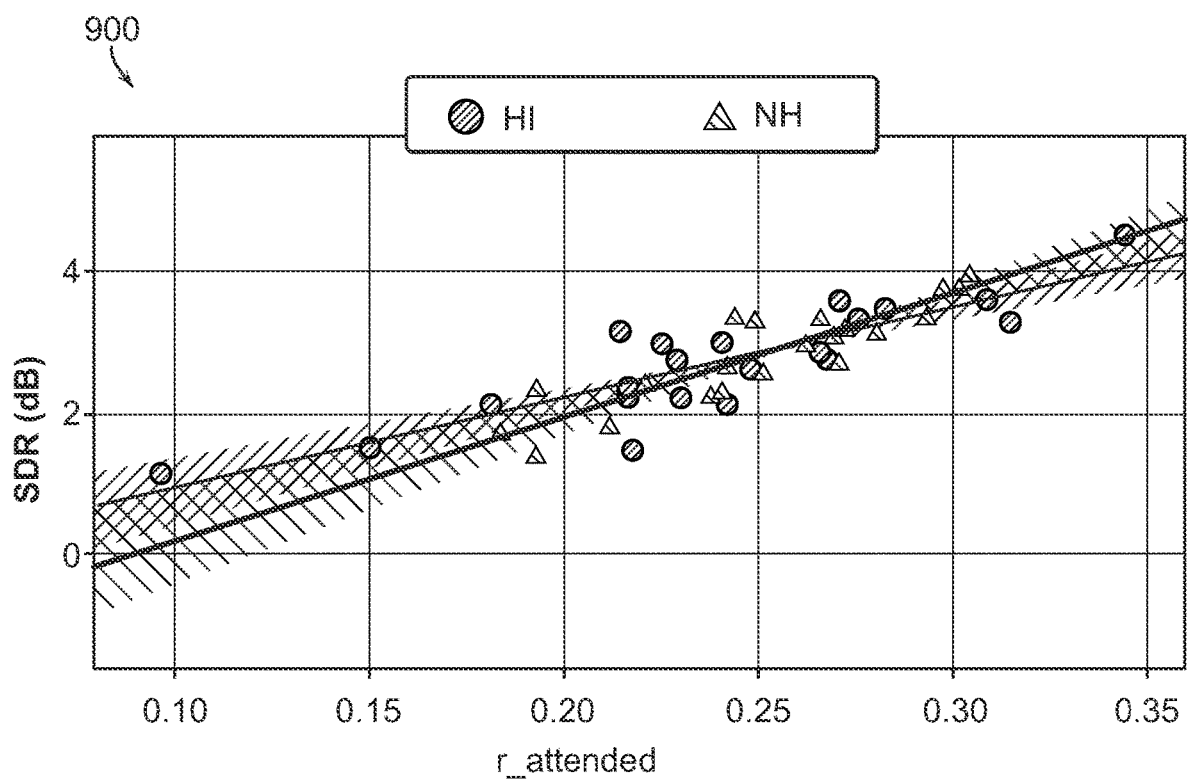
FIG. 9 includes a graph showing the separation performance using envelopes reconstructed from EEG for each subject.

As expected, the overall performance is lower for EEG than with iEEG. As with iEEG, no significant difference was found between the causal and non-causal settings (p=9.3e-01). Moreover, no statistical difference was found between NH and HI for the causal (p=4.508e-01) and non-causal settings (p=1.865e-01). The overall performance of each subject was also examined in terms of $r_{diff}$ and SDR improvement. FIG. 9 includes a graph 900 showing the separation performance using envelopes reconstructed from EEG for each subject (the y-axis shows the separation quality in terms of SDR improvement in dB, and significance is indicated by ns if p>0.05 using Mann-Whitney U test). The graph 900 shows the median SDR versus the median $r_{diff}$ for all EEG subjects. Similar to iEEG, both groups show a clear and similar correlation between the $r_{diff}$ and SDR. Overall, the EEG results show a positive correlation with a slope of 14.2 which is very close to the overall positive correlation of iEEG data which is 14.7.

Figure 10:
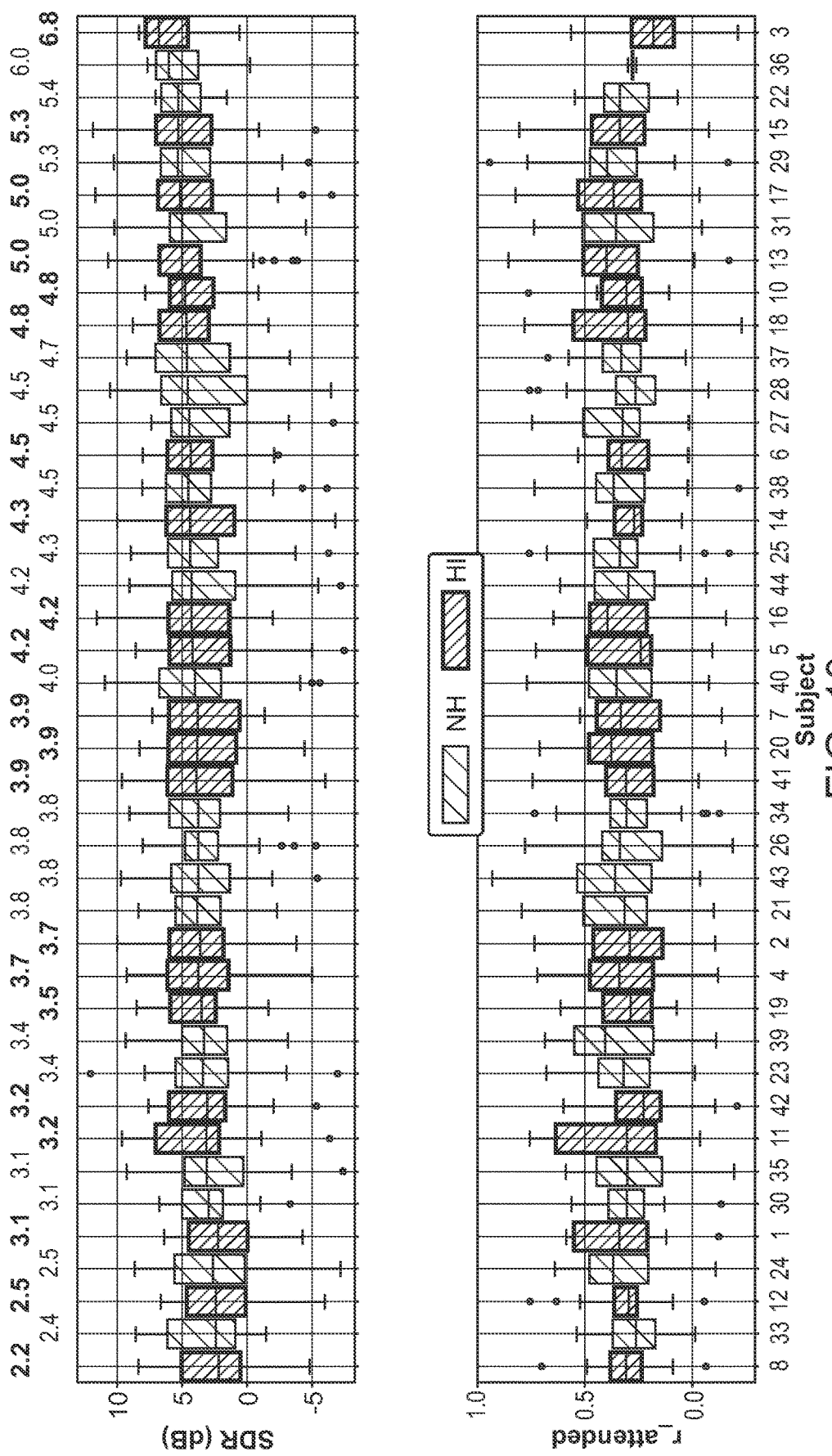
FIG. 10 includes a graph of distribution and the median SDR performance results for all individual subjects undergoing EEG tests.

Additionally, the distribution of performance for each subject individually across the 128 utterances was examined. Only trials in which the decoding of utterances were successful were considered, i.e., with $r_{diff}>0$. FIG. 10 includes a graph 1000 of the distribution and the median SDR performance result for all individual subjects of the EEG tests, ordered by increasing SDR (median values for SDR are highlighted above the top panel). The difference in performance between the best and worst subjects is 4.6 dB, with the best and worst subjects having median SDRs of 6.8 dB and 2.2 dB, respectively.

The brain-controlled speech separation approach described herein is configured to use a single-trial neural responses of a listener attending to a speaker to extract and enhance that speaker from the mixed audio. By utilizing the information provided by the envelope reconstruction process/algorithm, this methodology can extract the attended speaker from a mixture of two (or more) speakers as well as from speech-shaped background noise in the auditory scene, making it a viable solution for neuro-steered hearing aids (HAs). Auditory attention decoding generally assumes that the clean speech of the speakers in a mixture is available to be compared to the neural signals to determine the target source. This access to clean sources is not realistic in real-world applications. The proposed novel framework combines the steps of speaker separation and speaker selection by turning speech separation into speech extraction. Not only does this framework readily generalize to competing speakers or background noise, but it also requires significantly less computation than other speech separation approaches because only the target speaker is extracted.

Figure 11:
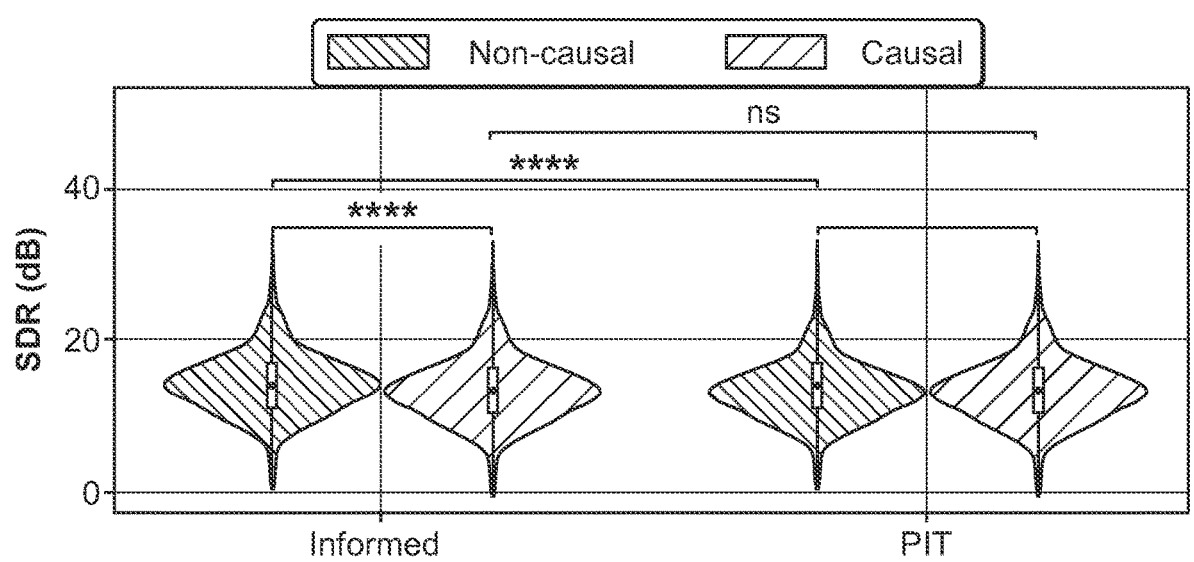
FIG. 11 includes graphs with violin plots comparing performance of the BISS approach to a permutation invariant training (PIT) approach, for both causal and non-causal settings.

Specifically, as part of the testing and investigation of the performance of the BIS S framework described herein, the proposed informed speech separation approach was compared with a permutation invariant training (PIT), which is a method for training deep-learning based speech separation models. In the testing conducted for the BISS approach, the hint input for the BISS model came from the envelope of the ground truth attended speech. FIG. 11 includes graphs with violin plots comparing performance of the BISS approach to the PIT approach, for both causal and non-causal settings. The results in FIG. 11 show that ISS gives significantly better results (p=7.8461e-09) than PIT for the causal setting. The non-causal setting results, on the other hand, show no significant difference (p=0.1101) between ISS and PIT. The ISS process, however, produces significantly better results under non-causal settings (p=5.0211e-09) over causal settings. The causal setting gives an absolute median difference of ≈0.9 dB, a value that still indicates good separation quality for practical applications. It is to be noted that the model trained with PIT has around 1 million parameters, while the model size scales almost linearly with the number of speakers in the mixture. On the other hand, the ISS model has only 0.5 million parameters and this number does not have to scale with the number of speakers in the mixture. Similarly, the number of operations to compute one spectrogram column mask is around 14 MOps for the PIT model and 7 MOps for the ISS model, which makes the ISS model more efficient and computationally cheaper so as to facilitate real-time applications. The number of parameters and number of operations are calculated based on the final settings of the model chosen for the best trade-off between size and performance. The final settings are shown in Table 1 and give rise to a receptive field with a span of 3.9 s in time and a span of 7900 Hz in frequency.

TABLE 1

| Symbol | Description | Value |
| --- | --- | --- |
| F | Number of frequency bins | 257 |
| L | Number of STFT time windows | 257 |
| T | Number of samples in the waveform | 32000 |
| C | Channels in the stack | 32 |
| B | Channels in the convolutional step | 64 |
| S | Number of stacks | 2 |
| N | Number of blocks | 6 |
| i | Index of each block (dilation factor) | — |
| s | Index of each stack | — |
| k | kernel size | 3 |

Additionally, the speech separation quality (SDR) is highly correlated with stimulus reconstruction accuracy. This close correlation between these two quantities reveals two desired aspects of the proposed framework. First, it confirms the hypothesis that speech separation quality is higher in a model that takes additional information as input (see results of FIG. 11), in this case the target speaker envelope reconstructed from the neural responses of the listener. Moreover, it offers a more general solution with respect to speaker extraction since the information about the target speaker can be obtained directly from the subject's brain on a trial-to-trial basis and does not have to be known a priori. Second, the speech separation quality of the model in the proposed framework follows the attention level of the subject which directly affects the reconstruction accuracy ($r_{diff}$), and thus reflects the intent of the subject. In closed-loop applications of AAD, the separated target speech is typically added to the original mixed signal in order to both amplify the target speaker, but also to maintain the audibility of other sources to enable attention switching (usually 6-12 dB). Since the BISS framework creates an output SDR which is correlated with the attention of the subject (r), this alleviates the need to render the mixture speech with a particular SNR because the SNR will naturally reflect the attention of the subject. This attention driven target SNR could help with attention switching in closed-loop applications. The results obtained from applying AAD to EEG data are similar to the results obtained with iEEG but with smaller Pearson's r of the reconstructed envelope and lower SDR of separated speech. Even though these results are less accurate, they are in accordance with the predictions made using iEEG for AAD. In particular, the $r_{diff}$ and the output SDR are highly correlated, confirming again that the model follows the subject's attention. Moreover, the AAD results using EEG show no significant difference in target speech enhancement (SDR) between HI and NH subjects. This shows that the proposed BISS approach can be used by HI subjects, which is a crucial aspect for the applicability of the framework to neuro-steered HAs.

It is also worth noting that the same speech separation model was used to produce the results presented from both iEEG and EEG. This shows the versatility of the proposed approach. Not only can the framework be applied successfully in the presence of different languages and noise, but it is also unaffected by different methods of reconstruction and different types of brain signals used. Particularly, to show that the BISS framework can successfully be applied across tasks of speaker separation and speech enhancement, the testing performed on the proposed framework also looked at the possibility of reducing noise in attended speech using EEG signals. This is an easier task to solve than speaker separation. This is mainly due to the fact that the noise and speech have different frequency distributions and are easier to separate than 2 overlapping speakers. In particular, speech enhancement models that use neural networks can easily be trained without the need to use PIT: if one assumes only one speaker, there is no mixed signal to resolve from which a desired signal is to be extracted. EEG recorded from a NH subject listening to speech in stationary speech-shaped background noise was used. The network tested is the same one used above, but it was trained with more added noise in the input, with respect to the model used for speaker separation. The hint to the network was still the envelope reconstructed from the EEG of the subject.

Figure 12:
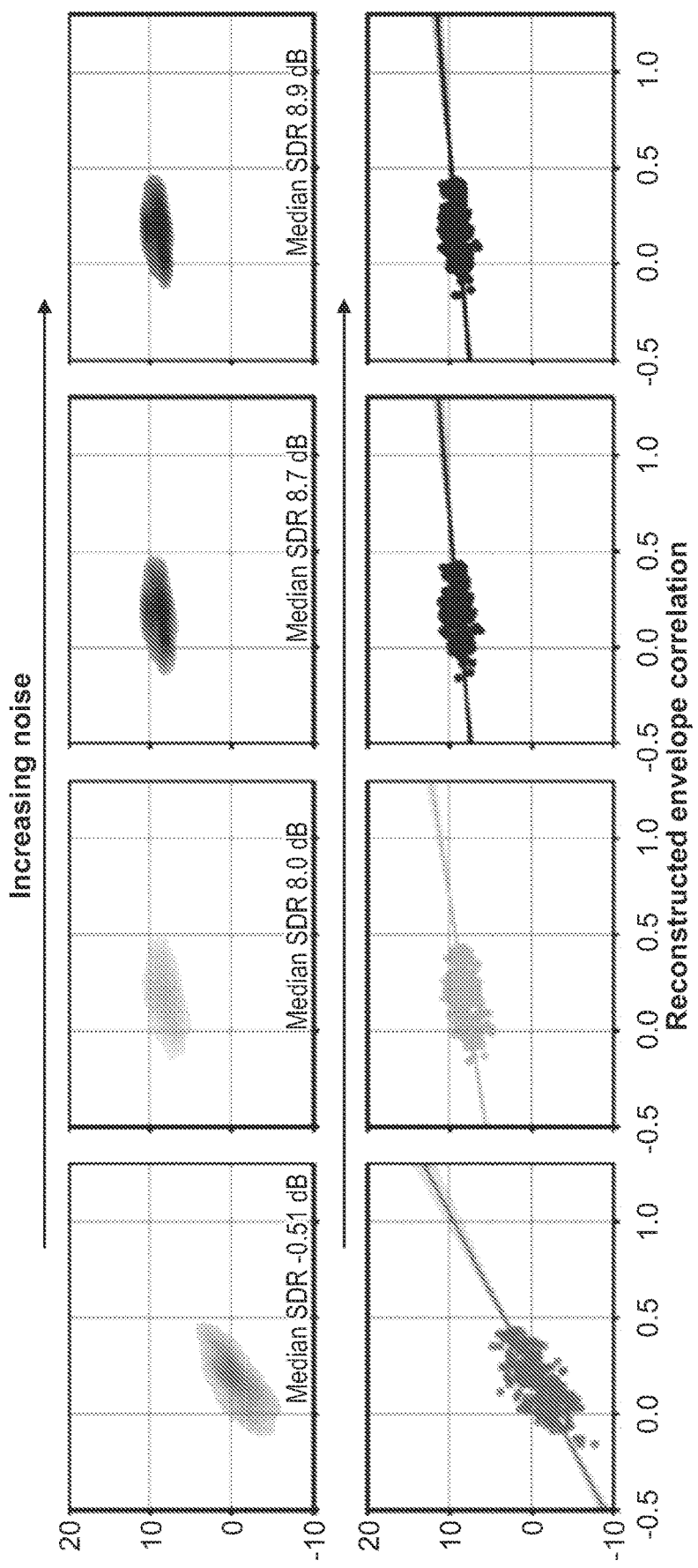
FIG. 12 includes graphs showing performance results for the implemented BISS framework when tested for a particular subject.

FIG. 12 includes graphs showing performance results for the implemented BISS framework when tested for a particular subject. In FIG. 12, the x-axis indicates $r_{speech}$ value, and the y-axis indicates SDR in dB. The panels in the top row show the density distribution of the points using kernel density estimate with Gaussian kernels. The panels in the bottom row show each utterance separately and a linear fit obtained using linear regression. The shaded area represents the 95% confidence interval of the regression. The panels from left to right show results from increasing the a of the noise during training (from $\sigma=0.0$ to $\sigma=0.6$ with steps of 0.2).

Figure 13:
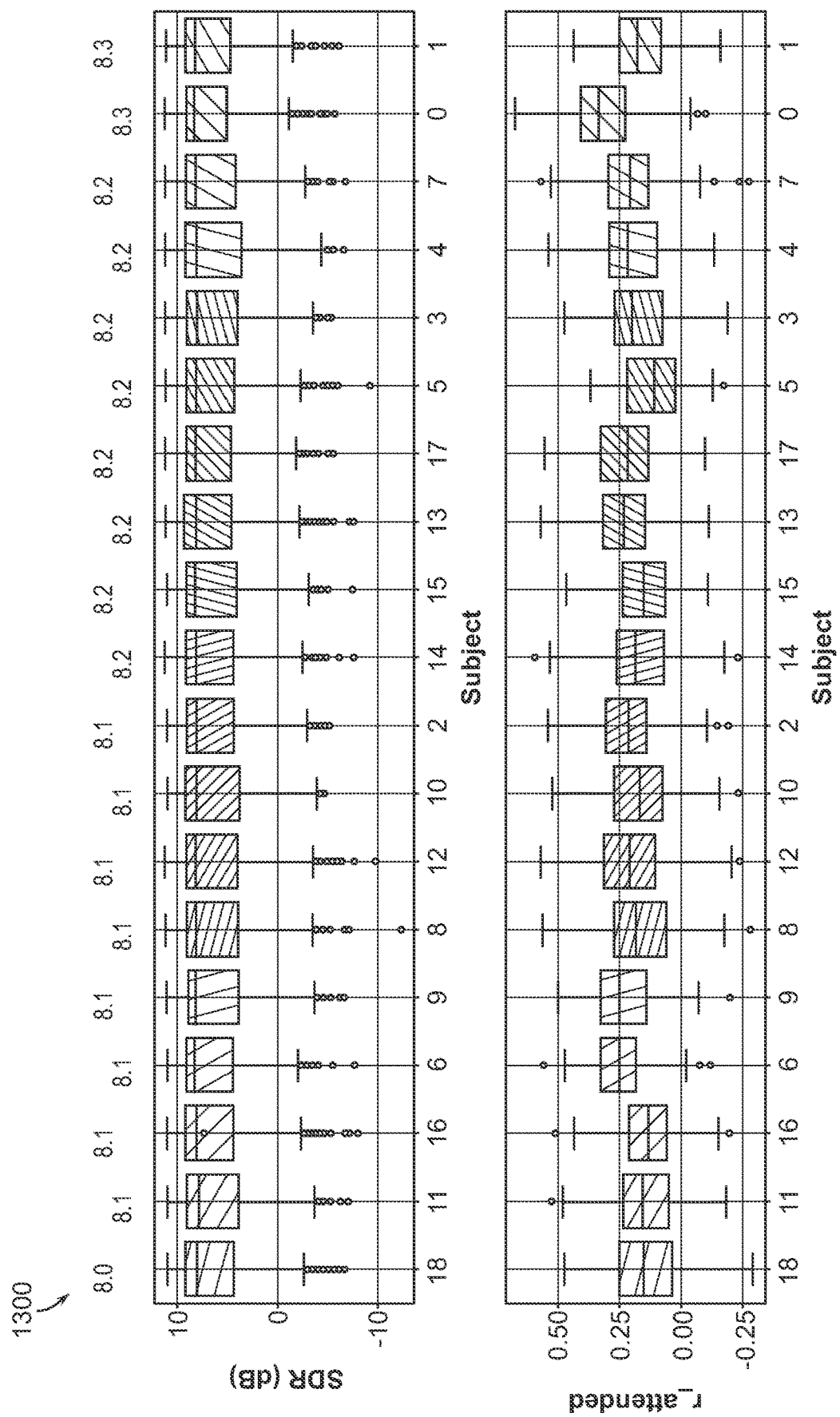
FIG. 13 includes a graph of distribution and median SDR performance results for all individual subjects of the EEG tests.

Results for the particular subject tested demonstrate that the training scheme is effective in increasing the robustness of the network to the non-perfect reconstructed envelope. As can be seen, compared to iEEG in speaker separation, even a low amount of noise helps the network in making use of the hint to separate the desired voice. Moreover, it can be seen from FIG. 13, which includes a graph 1300 of the distribution and the median SDR performance result for all individual subjects of the EEG tests, that the method can be successfully applied to all the subjects. Differently from the speaker separation task, it can be seen that for speech enhancement, the linear trend between Pearson's r value and output SDR is less evident than the one present for speaker separation. This is due to the fact that the task is much easier to solve and that even a reconstructed envelope with a low reconstruction quality is informative enough for the model to separate the desired speaker.

The above findings suggest that the BISS approach is a robust speech separation frontend. Moreover, the finding that BISS results in no significant difference between causal and non-causal speech separation models increases its usability in real-time systems which require causal, short-latency implementation (<20 ms).

Finally, BISS can decouple the optimization of front-end (speech separation) and back-end (AAD) systems even when a small amount of data is available. This joint optimization can also be done when large amounts of data are available. While the tested present approach used basic neural signal decoding (e.g., speech envelope reconstruction), there are many other ways to implement attention decoding, including, for example, by reconstructing the speech spectrograms. Moreover, the neural decoding can be done either with classification or state space models. These methods can be easily integrated into the BISS framework because it takes as the hint (speaker attending brain information) any signal that is correlated with the attended speech.

Additional Embodiments

The example separation technique (based on 2D convolutional operations) discussed in relation to FIGS. 1-13 is but one example of a separation technique in which brain-informed data can be leveraged to generate a separation filter(s) that is to be applied to a combined, multi-source sound signal. Other separations schemes may be used in place of, or in addition to, the sound/speech separation approach used in the implementations of FIGS. 1-13. Discussed below are additional examples of separation techniques in which the speaker attended information, determined from a listener's brain signals, can be used to determine and apply sound separation processing to extract the desired signal(s). These additional separation techniques can, for example, include a hint fusion module to create a composite signal from the captured multi-source signal and the speaker-attending information. Such a hint fusion module may be similar to, or different from, the hint fusion module 200 depicted in FIG. 2A.

A first additional example implementation of a separation technique that can be used in conjunction with, or as an alternative to, the separation systems described in relation to FIGS. 1-13 is one based on separating varying numbers of sources with auxiliary autoencoding loss. Iterative separation methods offer flexibility in that they can determine the number of outputs. However, such iterative techniques typically rely on long-term information to determine the stopping time for the iterations, which makes them hard to operate in a causal setting. Additionally, such techniques lack a "fault tolerance" mechanism when the estimated number of sources is different from the actual number. To mitigate these problems, a simple training method, the auxiliary autoencoding permutation invariant training (A2PIT) is proposed. A2PIT assumes a fixed number of outputs and uses auxiliary autoencoding loss to force the invalid outputs to be the copies of the input mixture. This methodology therefore detects invalid outputs in a fully unsupervised way during inference phase. Experiment results show that A2PIT is able to improve the separation performance across various numbers of speakers and effectively detect the number of speakers in a mixture. A2PIT not only allows the model to perform valid output detection in a self-supervised way without additional modules, but also achieves "fault tolerance" by the "do nothing is better than do wrong things" principle. Since the mixture itself can be treated as the output of a null separation model (i.e., perform no separation at all), the auxiliary targets force the model to generate outputs not worse than doing nothing. Moreover, the detection of invalid outputs in A2PIT can be done at frame-level based on the similarity between the outputs and the mixture, which makes it possible to perform single-pass separation and valid source detection in real-time.

Permutation Invariant Training (PIT) is a speech separation technique that aims at solving the output permutation problem in supervised learning settings, where the correct label permutation of the training targets is unknown with respect to the model outputs. PIT computes the loss between the outputs and all possible permutations of the targets, and selects the one that corresponds to the minimum loss for back-propagation. Models using PIT for training often have a fixed number of outputs, which is denoted as the number N. For the problem of separating varying numbers of sources where the actual number of sources are M≤N, N-M auxiliary targets need to be properly designed. One approach is to use low-energy random Gaussian noise as targets and detect invalid outputs by using a simple energy threshold, and it has been shown that in certain datasets this energy-based method can achieve reasonable performance.

There are two main issues in the energy-based method for invalid output detection. First, it typically cannot be jointly used with energy-invariant objective functions like SI-SDR. Second, once the detection of invalid speakers fails and the noise signals are selected as the targets, the outputs can be completely uncorrelated with any of the targets, which is undesirable for applications that require high perceptual quality or low distortion (this is referred to as the problem of lacking a "fault tolerance" mechanism for unsuccessful separation). To allow the models to use any objective functions and to have such "fault tolerance" ability, a mixture signal itself is selected as the auxiliary targets instead of random noise signals. In some embodiments, and as discussed herein, the mixture signal may be fused with hint information (i.e., speaker-attended information derived based on the listener's neural signals). For mixtures with N outputs and M<N targets, N-M mixture signals are appended to the targets and PIT is applied to find the best output permutation with respect to the targets. The A2PIT loss with the best permutation then becomes:

$$L_{obj}=L_{sep}+L_{AE}$$

where $L_{sep} \in \mathbb{R}$ is the loss for the valid outputs, and $L_{AE} \in \mathbb{R}$ is the auxiliary autoencoding loss for the invalid outputs with the input mixture as targets. As autoencoding is in general a much simpler task than separation, proper gradient balancing method should be applied on the two loss terms for successful training.

SI-SDR is defined as:

$$SI-SDR(x, \hat{x}) = 10\log_{10}\frac{\|\alpha x\|_2^2}{\|\hat{x}-\alpha x\|_2^2}$$

where $\alpha=\hat{x}x^T/xx^T$ corresponds to the optimal rescaling factor towards the estimated signal. Let $a \triangleq xx^T$, $b \triangleq \hat{x}x^T$, and $c \triangleq \hat{x}\hat{x}^T$. The SI-SDR can thus be expressed as:

$$SI-SDR(x, \hat{x}) = 10\log_{10}\left(\frac{b^2/a}{c-2b^2/a+b^2/a}\right)$$
$$= 10\log_{10}\left(\frac{1}{ac/b^2-1}\right)$$
$$= 10\log_{10}\left(\frac{c(x,\hat{x})^2}{1-c(x,\hat{x})^2}\right).$$

where $c(x,\hat{x}) \triangleq b/\sqrt{ac} = \hat{x}x^T/\sqrt{(xx^T)(\hat{x}\hat{x}^T)}$ is the cosine similarity between x and $\hat{x}$. The scale-invariance behavior of SI-SDR can be easily observed by the nature of cosine similarity, and SI-SDR(x,$\hat{x}$)→+∞ as |c(x,$\hat{x}$)|→1. It's easy to see that the second term in |∂SI-SDR(x,$\hat{x}$)/∂c(x,$\hat{x}$)| approaches infinity as |c(x,$\hat{x}$)| approaches 1. Using it for $L_{AE}$ may let the system to easily collapse to a local minimum which have very high performance on the auxiliary autoencoding term while failing to separate the sources. Accordingly, based on this concern, an α-skewed SI-SDR is proposed, which is defined as:

$$\alpha SI-SDR(x, \hat{x}) \triangleq 10\log_{10}\left(\frac{c(x,\hat{x})^2}{1+\alpha-c(x,\hat{x})^2}\right),$$

where the scale of the gradient with respect to the cosine similarity term is controlled by α≥0, and α=0 corresponds to the standard SI-SDR. For multiple-speaker utterances, a is empirically set to α=0.3 for $L_{AE}$, and α=0 for $L_{sep}$. For single speaker utterances, the training target for separation is equivalent (when there is no noise) or very close (when there is noise) to the input mixture. In this case, α is also set to α=0.3 for $L_{sep}$.

During inference phase, the detection of invalid outputs can be performed by calculating the similarity, e.g., SI-SDR score, between all outputs and the input mixture, and a threshold calculated from the training set can be used for the decision. For the "fault tolerance" mechanism, the following method is applied for selecting the valid outputs:
1. If the estimated number of outputs K is smaller than the actual number M, M-K additional outputs are randomly selected from the N-K remaining outputs.
2. If the estimated number of outputs K is larger than the actual number M, M outputs are randomly selected from the K outputs.

Another benefit for A2PIT is that it also allows frame-level detection of the invalid outputs for causal applications. Frame level detection calculates accumulated similarity starting from the first frame of the outputs, and is able to dynamically change the selected valid outputs as the similarity scores become more reliable. For streaming-based applications that require a real-time playback of the separation outputs, e.g., hearable devices, the change of the output tracks can also be easily done by switching the outputs at frame-level.

A second additional example implementation of a separation approach that can be used in conjunction with, or as an alternative to, the separation systems described in relation to FIGS. 1-13 is one based on real-time binaural speech separation with preserved spatial cues. Some separation techniques focus on generating a single-channel output for each of the target speakers, thus discarding the spatial cues needed for the localization of sound sources in space. However, preserving the spatial information is important in many applications that aim to accurately render the acoustic scene such as in hearing aids and augmented reality (AR). Therefore, in some embodiments, a further speech separation approach/algorithm is proposed that preserves the interaural cues of separated sound sources and can be implemented with low latency and high fidelity, therefore enabling a real-time modification of the acoustic scene. The present proposed approach is based on a time-domain audio separation network (TasNet), which is a single-channel time-domain speech separation system that can be implemented in real-time. Further details about example implementation of a single channel TasNet frameworks are provided in U.S. Ser. No. 16/169,194, entitled "Systems and methods for speech separation and neural decoding of attentional selection in multi-speaker environments," the content of which is hereby incorporated by reference in its entirety. The proposed approach is a multi-input-multi-output (MIMO) end-to-end extension of the single-channel TasNet approach, in which the MIMO TasNet approach takes binaural mixed audio as input and simultaneously separates target speakers in both channels. Experimental results show that the proposed end-to-end MIMO system is able to significantly improve the separation performance and keep the perceived location of the modified sources intact in various acoustic scenes.

More particularly, in real-world multi-talker acoustic environments, humans can easily separate speech and accurately perceive the location of each speaker based on the binaural acoustic features such as interaural time differences (ITDs) and interaural level differences (ILDs). Speech processing methods aimed to modify the acoustic scene are therefore required to not only separate sound sources, but do so in a way that preserves the spatial cues needed for accurate localization of sounds. However, most binaural speech separation systems are multi-input-single-output (MISO), and hence lose the interaural cues at the output level which are important for humans to perform sound lateralization and localization. To achieve binaural speech separation as well as interaural cues preservation, the multi-input-multi-output (MIMO) proposed herein setting is used.

One issue of conventional MIMO systems is that the system latency can be perceived by humans, and the delayed playback of the separated speakers might affect the localization of the signals due to the precedence effect. To decrease the system latency while maintaining the separation quality, one solution is to use time-domain separation methods with smaller windows. Recent deep learning-based time-domain separation systems have proven their effectiveness in achieving high separation quality and decreasing the system latency. However, such systems are still MISO and their ability to perform binaural speech separation and interaural cues preservation is not fully addressed.

In the proposed approach, a multi-speaker system is formulated as a MIMO system to achieve high-quality separation and to preserve interaural cues. Based on the time-domain audio separation network, a MIMO TasNet approach is proposed that takes binaural mixture signals as input and simultaneously separates speech in both channels. The separated signals can then be directly rendered to the listener without post-processing. The MIMO TasNet exploits a parallel encoder to extract cross-channel information for mask estimation, and uses mask- and sum method to perform spatial and spectral filtering for better separation performance Experiment results show that MIMO TasNet can performs listener-independent speech separation across a wide range of speaker angles and can preserve both ITD and ILD features with significantly higher quality than the single-channel baseline. Moreover, the minimum system latency of the systems can be less than 5 ms, showing the potentials for the actual deployment of such systems into real-world hearable devices. The proposed MIMO TasNet approach may also fuse (incorporate speaker-attended information derived from measurements of the listener's neural signals.

The problem of binaural speech separation is formulated as the separation of C sources, $s_i^{l,r}(t) \in \mathbb{R}^{1 \times T}, \ldots, C$ from the binaural mixtures $x^l(t), x^r(t) \in \mathbb{R}^{1 \times T}$, where the superscripts l and r denote the left and right channels, respectively. For preserving the interaural cues in the outputs, consider the case where every single source signal is transformed by a set of head-related impulse response (HRIR) filters for a specific listener:

$$\begin{cases} s_i^l = \hat{s}_i * h_i^l \\ s_i^l = \hat{s}_i * h_i^r \end{cases}, i = 1, \ldots, C$$

where $\hat{s}_i \in \mathbb{R}^{1 \times T'}$ is the monaural signal of source i, $h_i^l, h_i^r \in \mathbb{R}^{1 \times (T-T'+1)}$ are the pair of HRIR filters corresponding to the source i, and * represents the convolution operation. Using the HRIR-transformed signals as the separation targets forces the model to preserve interaural cues introduced by the HRIR filters, and the outputs can be directly rendered to the listener.

TasNet has been shown to achieve superior separation performance in single-channel mixtures. TasNet contains three modules: a linear encoder first transforms the mixture waveform into a two-dimensional representation; a separator estimates C multiplicative functions, and a linear decoder transforms the C target source representations back to waveforms. The TasNet pipeline incorporates cross-channel features into the single-channel model, where spatial features such as interaural phase difference (IPD) is concatenated with the mixture encoder output on a selected reference microphone for mask estimation. In various scenarios, such configurations can lead to a significantly better separation performance than the signal-channel TasNet.

The proposed MIMO TasNet uses a parallel encoder for spectro-temporal and spatial features extraction and a mask-and-sum mechanism for source separation. A primary encoder is always applied to the channel to be separated, and a secondary encoder is applied to the other channel to jointly extract cross-channel features. In other words, the sequential order of the encoders determines which channel (left of right) the separated outputs belong to. The outputs of the two encoders are concatenated (or otherwise combined) and passed to the separator, and 2C multiplicative functions are estimated for the C target speakers. C multiplicative functions are applied to the primary encoder output while the other C multiplicative functions are applied to the secondary encoder output, and the two multiplied results are then summed to create representations for C separated sources. This approach is referred to as the "mask-and-sum" mechanism to distinguish it from the other methods where only C multiplicative functions were estimated from the separation module and applied to only the reference channel. A linear decoder transforms the C target source representations back to waveforms.

Figure 14:
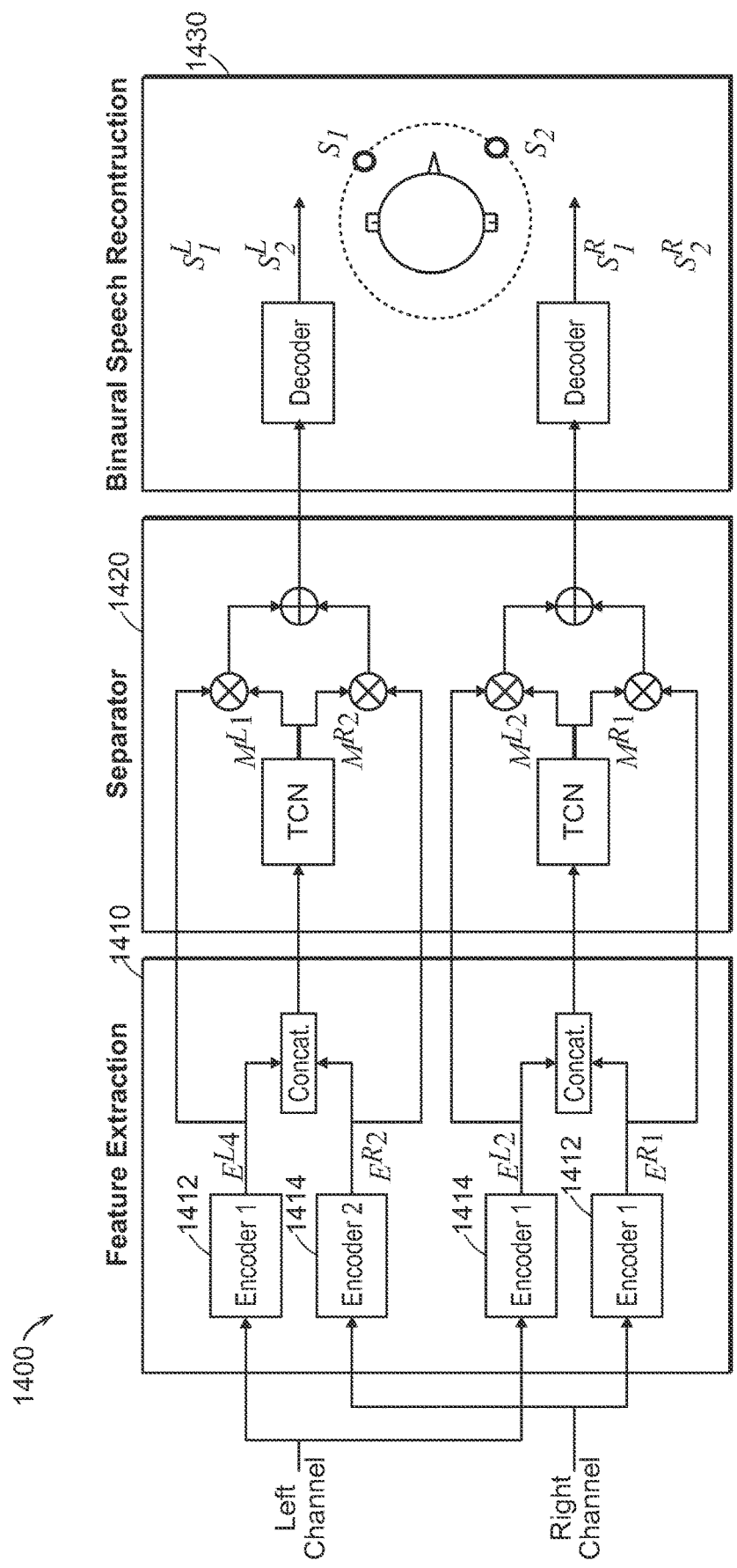
FIG. 14 is a schematic diagram of an example architecture for a multi-channel (e.g., binaural) speech separation network.

FIG. 14 is a schematic diagram of an example architecture 1400 of a multi-channel (e.g., binaural) speech separation network. The architecture 1400 includes a feature extraction section 1410 that includes multiple encoders (in the example of FIG. 14, two encoders 1412 and 1414 are depicted) which are shared by the mixture signals from both channels, and the encoder outputs for each channel are combined (e.g., concatenated, integrated, or fused in some manner), to thus preserve spatial cues, and passed to a mask estimation network. As noted, in some embodiment, hint information derived from the listener's neural signals (with such signals being indicative of the speaker(s) the listener's is attending to) may also be combined (e.g., concatenated, or integrated in some other manner) with the encoders' output and passed to a separator section 1420 (also referred to as a mask estimation network). Spectral-temporal and spatial filtering are performed by applying the masks to the corresponding encoder outputs (e.g., deriving and applying multiplicative functions derived for each group of sources from the multiple sound sources constituting the combined signal; for instance, multiplicative functions can be determined, per each of the receiving channels, for each speaker contributing to the combined signal), and the resultant outputs from the application of the multiplicative functions are summed up (e.g., on both left and right paths). Finally, the binaural separated speech is reconstructed by one or more linear decoders in a speech reconstruction section 1430. For an N-channel input, N encoders were applied to each of them, and the encoder outputs are summed to create a single representation.

When the architecture 1400 is used to perform the separation filter determination operation of, for example, the procedure 400 previously described, the combined sound signal may include in such embodiments components corresponding to multiple receiving channels (e.g., a first and second receiving channels, which may correspond to a left and a right binaural channels), and determining the separation filter may include applying multiple encoders (e.g., temporal-domain encoders) to the sound components corresponding to the multiple receiving channels, with each of the encoders applied to each of the sound components, and, for each of the multiple receiving channels, combining output components of the multiple encoders associated with respective ones of the multiple receiving channels. In such embodiments, the procedure 400 may also include deriving estimated separation functions based on the combined output components for each of the multiple receiving channels, with each of the derived estimated separation functions configured to separate the combined output components for each of the multiple receiving channels into separated sound components associated with groups (e.g., each group comprising one or more speakers) of the multiple sound sources.

Scale-invariant signal-to-distortion ratio (SI-SDR) may be used as both the evaluation metric and training objective for the present approaches. As noted, SI-SDR between a signal $x \in \mathbb{R}^{1 \times T}$ and its estimate $\hat{x} \in \mathbb{R}^{1 \times T}$ is defined as:

$$SI-SDR(x, \hat{x}) = 10\log_{10}\left(\frac{\|\alpha x\|_2^2}{\|\hat{x} - \alpha x\|_2^2}\right)$$

where $\alpha = \hat{x}^T x / x x^T$ corresponds to the rescaling factor. Although SI-SDR is able to implicitly incorporate the ITD information, the scale-invariance property of SI-SDR makes it insensitive to power rescaling of the estimated signal, which may fail in preserving the ILD between the outputs.

Thus, instead of using SI-SDR as the training objective, the plain signal-to-noise ratio (SNR) may be used instead. The SNR is defined as:

$$SNR(x, \hat{x}) = 10\log_{10}\left(\frac{\|x\|_2^2}{\|\hat{x} - x\|_2^2}\right)$$

Accordingly, as discussed above, the MIMO TasNet framework, which seeks to implement real-time binaural speech separation with interaural cues preservation, uses a parallel encoder and mask-and-sum mechanism to improve performance Experimental results show that the MIMO TasNet is able to achieve very good separation performance and has the ability to preserve interaural time difference (ITD) and interaural level difference (ILD) features. Additional improvements may also take into account environmental noise and room reverberation, and incorporate extra microphones for obtaining more cross-channel information.

A third additional example implementation of a separation approach that can be used in conjunction with, or as an alternative to, the separation systems described in relation to FIGS. 1-14 is one based on binaural speech separation of moving speakers with preserved spatial cues. Binaural speech separation algorithms designed for augmented hearing technologies need to both improve the signal-to-noise ratio of individual speakers and preserve their perceived locations in space. The majority of binaural speech separation methods assume nonmoving speakers. As a result, their application to real-world scenarios with freely moving speakers requires block-wise adaptation which relies on short-term contextual information and limits their performance. Accordingly, a further separation approach (which like the approaches described herein may incorporate brain-informed data) for utterance-level source separation with moving speakers and in reverberant conditions is proposed. The proposed model makes use of spectral and spatial features of speakers in a larger context compared to the block-wise adaption methods. The model can implicitly track speakers within the utterance without the need for explicit tracking modules. Experimental results on simulated moving multi-talker speech show that this proposed approach can significantly outperform block-wise adaptation methods in both separation performance and preserving the interaural cues across multiple conditions, which makes it suitable for real-world augmented hearing applications. The proposed approach does not require localization and tracking modules and is thus able to preserve the spatial cues in the outputs which enables the correct localization of the separated moving source. The framework uses a binaural separation module and a binaural post enhancement module. The binaural speech separation module takes binaural mixed signals as input and simultaneously separates speech in both channels; then the left and right channel speech of each speaker are concatenated (or otherwise combined) and further enhanced by the binaural post enhancement module; the output of the binaural post enhancement module is the separated stereo sound rendered to the listener. The modules employ the TasNet framework (referred to above) that can achieve latency as low as 2 ms, and which is important for deployment in hearing devices. Experimental results show that utterance-level separation significantly outperforms the block-wise adaptation methods both in terms of signal quality and spatial cue preservation.

Figure 15:
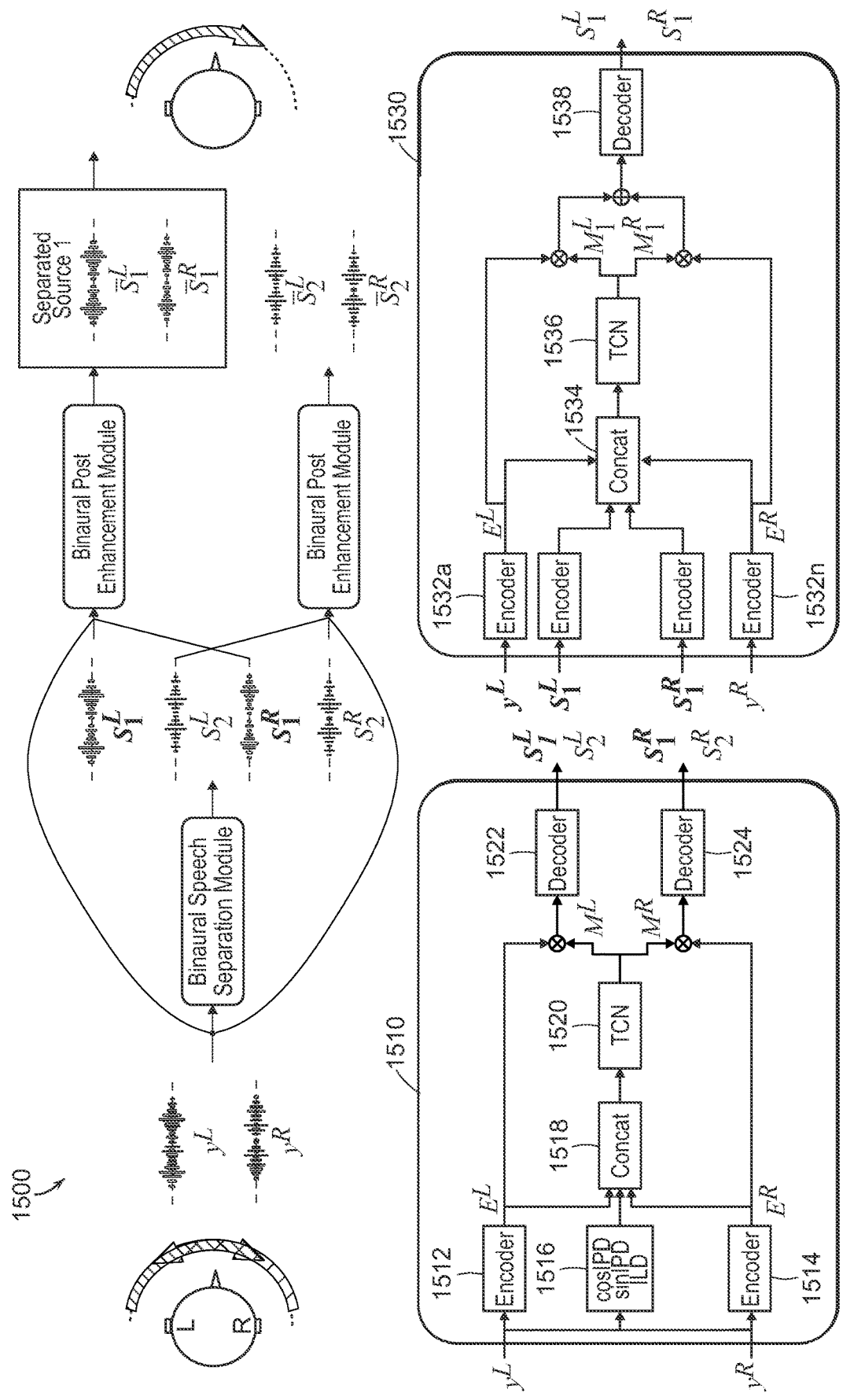
FIG. 15 is a schematic diagram of an example architecture for a binaural speech separation system for moving speakers.

With reference to FIG. 15, a schematic diagram of an example architecture 1500 for a binaural speech separation system for moving speakers is shown. Operation of the example architecture 1500 is illustrated for two speakers ($s_1$ and $s_2$), but any number of speakers may be used in conjunction with the architecture 1500. The architecture 1500 includes a binaural speech separation section (module) 1510 and a binaural post enhancement section (or module) 1530. The binaural speech separation section 1510 simultaneously separates the speakers in each channel of the mixed input, while the section 1530 enhances each speaker individually. TasNet approaches have shown superior separation performance on various conditions, and TasNet can be implemented with causal configuration with low latency which is needed for real-time applications. In the proposed architecture 1500, a MIMO configuration is again used. As noted above in relation to the architecture 1400 of FIG. 14, the MIMO TasNet contains three steps: (1) spectral and spatial feature extraction, (2) estimation of multiplicative functions, which is similar to 2-D time-frequency masks, and (3) speech reconstruction. In the present example architecture 1500, two linear encoders transform the left- and right-channel of the mixed signals $y^L$, $y^R \in \mathbb{R}^T$ into 2-D representations $E^L$, $E^R \in \mathbb{R}^{N \times H}$, respectively, where N is the number of encoder basis and H is the number of time frames. To enhance the extraction of the spatial features, the interaural phase difference (IPD) information and interaural level difference (ILD) information are explicitly added as additional information/features to the outputs of the encoders 1512 and 1514. Specifically, in some embodiments, the following features are computed:

$$\cos \text{IPD} = \cos(\angle Y^L - \angle Y^R)$$

$$\sin \text{IPD} = \sin(\angle Y^L - \angle Y^R)$$

$$\text{ILD} = 10 \log_{10}(|Y^L| \oslash |Y^R|)$$

where $Y^L$, $Y^R \in \mathbb{R}^{N \times H}$ are the spectrograms of $Y^L$, $Y^R$, respectively, F is the number of frequency bins, and $\oslash$ is element-wise division operation. The hop size for calculating $Y^L$, $Y^R$ is the same as that for $E^L$, $E^R$ to ensure they have the same number of time frames H, although the window length in the encoder is typically much shorter than that in the STFT. Finally, these cross-domain features are concatenated (or otherwise combined or integrated) by the unit 1518 (identified as "concat," although the unit 1518 can be configured to combine the signals in other manners) into $E^M = [E^L, E^R, \cos \text{IPD}, \sin \text{IPD}, \text{ILD}] \in \mathbb{R}^{(2N+3F) \times H}$ as the spectro-temporal and spatial-temporal features. Although not specifically shown in FIG. 15, the unit 1518 can also be configured to combine the brain-informed signal derived, for example, by the brain decoder 130, to yield $E^M = [E^L, E^R, \text{BIS}, \cos \text{IPD}, \sin \text{IPD}, \text{ILD}] \in \mathbb{R}^{(2N+3F) \times H}$, where BIS is the brain-informed signal generated by the decoder 130. The BIS signal may, in other embodiments, be combined with the speaker-related features/signals in other ways, and/or by other modules/units of the system 100 or 1500.

Subsequently, $E^M$ is fed into a series of temporal convolutional network (TCN) blocks 1520 to estimate multiplicative function $M^L$, $M^R \in \mathbb{R}^{C \times N \times H}$, where C is the number of speakers. $M^L$ and $M^R$ are applied to $E^L$ and $E^R$, respectively, and use one or more linear decoders 1522 and 1524 to transform the multiplied representations back to the waveforms $\{s_i^L\}_{i=1}^C$ and $\{s_i^R\}_{i=1}^C$. Due to the permutation problem, the order of the estimated speakers in each channel cannot be pre-determined. However, a constraint that the speaker order in two channels be the same can be imposed, which is important so as to pair the left- and right-channel signals of the individual speaker in a real-time system.

The post enhancement processing section (stage) 1530 is configured to further improve the signal quality. Each stereo sound, $s_i^L$ and $s_i^R$ from the separation module 1510, combined with the mixed signals ($y^L$, $y^R$), is sent to a multi-input-single-output (MISO) network for post enhancement. Similar to the speech separation module, the encoder outputs (From encoders 1532a-n) are concatenated (or otherwise combined) by the unit 1534 provided to TCN blocks 1536 for estimating multiplicative functions $M_i^L$, $M_i^R \in \mathbb{R}^{2 \times N \times H}$:

$$s_i^L = \text{decoder}(E^L \cdot M_i^L[0,:,:] + E^R \odot M_i^L[0,:,:])$$

$$s_i^R = \text{decoder}(E^L \cdot M_i^L[1,:,:] + E^R \odot M_i^L[1,:,:])$$

where $\odot$ denotes element-wise multiplication. Unlike the speech separation module 1510 that only applies multiplicative functions (which is equivalent to spectral filtering), the speech enhancement module performs multiplication and sum, which is equivalent to both spectral and spatial filtering (this is similar to multichannel wiener filtering). This is therefore referred to as the mask-and-sum mechanism.

Since the input stereo sound, $s_i^L$ and $s_i^R$, contains both spectral and spatial information of the speaker i, the enhancement module essentially performs informed speaker extraction without the need for permutation invariant training.

A speaker localizer (not specifically shown in FIG. 15) adopts a similar architecture as that of the speech enhancement module, but performs classification of the direction of arrival (DOA). The DOA angles are discretized into K classes. The speaker localizer takes only stereo sound, $s_i^L$ and $s_i^R$, as input, concatenates (or otherwise combines) two encoders' outputs, and passes them to the TCN blocks to estimate a single-class classification matrix $V_i \in (0,1)^{K \times H}$ where "single-class" means that in each time frame, there is exactly one class labeled with 1 and all the other classes are labeled with 0. $V_i$ is split into B small chunks $\{V_i^b\}_{b=1}^B \in \mathbb{R}^{K \times Q}$ where Q is the number of time frames in each chunk and B=H/Q. In each chunk the frequency of each class labeled with '1' is counted, and the most frequent class is deemed as the estimated DOA for that chunk.

The signal-to-noise ratio (SNR) is used as the training objective for the speech separation and enhancement sections. SNR is sensitive to both time shift and power scale of the estimated waveform, so it's able to force the ITD and IPD to be preserved in the estimated waveform. SNR is defined as:

$$SNR(x, \hat{x}) = 10 \log_{10}\left(\frac{\|x\|_2^2}{\|\hat{x} - x\|_2^2}\right)$$

where $\hat{x}$ and x are the estimated and reference signal, respectively. In the speech separation module, utterance-level permutation invariant training may be used. Thus, $$L = \min_{\pi \in P} \sum_{c=1}^{C} SNR(\hat{x}_c^L - x_{\pi(c)}^L) + SNR(\hat{x}_c^R - x_{\pi(c)}^R)$$

where P is the set of all C! permutations. The same permutation 7C for left- and right-channel signals assures the speaker is consistent in both channels.

When the architecture 1500 is used to perform the separation filter determination operation of, for example, the procedure 400 previously described, the combined sound signal may include, in such embodiments, representations of sound components corresponding to multiple receiving channels (e.g., a first and second receiving channels, which may correspond to a left and a right binaural channels). Determining the separation filter may include applying multiple encoders (e.g., the encoders 1512 and 1514) to the representations of sound components corresponding to the multiple receiving channels, with each of the encoders applied to each of the sound components. The determination of the separation filter also includes determining spatial features on the sounds components corresponding to the multiple receiving channels, combining (e.g., by the unit 1518 of FIG. 15) the determined spatial features with output components of the multiple encoders associated with respective ones of the multiple receiving channels, to produce a combined encoded output, deriving (e.g., by the TCN blocks 1520), based on the combined encoded output, estimated separation functions, and separating, using the estimated separation functions, the combined encoded output into separated sound components associated with groups of the multiple sound sources. In some embodiments, determining the spatial features may include determining one or more of, for example, interaural level difference (ILD) information, and/or interaural time difference (ITD) information.

In some examples, the operations performed by the architecture 1500 may further include combining the separated sound components with the representations of the sound components to produce a combined enhanced signal representation, and deriving estimated separation functions based on the combined enhanced signal representation to separate the combined enhanced signal representation into separated enhanced sound components associated with the groups of the multiple sound sources. In some additional examples, the operations performed by the architecture 1500 may further include determining, based on the separated sound components, direction of arrival of the separated sound components.

Performing the various techniques and operations described herein may be facilitated by a controller device (e.g., a processor-based computing device) that may be realized as part of a hearing aid device (that may also include a microphone and neural sensors coupled to the controller). Such a controller device may include a processor-based device such as a computing device, and so forth, that typically includes a central processor unit or a processing core. The device may also include one or more dedicated learning machines (e.g., neural networks) that may be part of the CPU or processing core. In addition to the CPU, the system includes main memory, cache memory and bus interface circuits. The controller device may include a mass storage element, such as a hard drive (solid state hard drive, or other types of hard drive), or flash drive associated with the computer system. The controller device may further include a keyboard, or keypad, or some other user input interface, and a monitor, e.g., an LCD (liquid crystal display) monitor, that may be placed where a user can access them.

The controller device is configured to facilitate, for example, the implementation of brain-informed speech separation. The storage device may thus include a computer program product that when executed on the controller device (which, as noted, may be a processor-based device) causes the processor-based device to perform operations to facilitate the implementation of procedures and operations described herein. The controller device may further include peripheral devices to enable input/output functionality. Such peripheral devices may include, for example, flash drive (e.g., a removable flash drive), or a network connection (e.g., implemented using a USB port and/or a wireless transceiver), for downloading related content to the connected system. Such peripheral devices may also be used for downloading software containing computer instructions to enable general operation of the respective system/device. Alternatively and/or additionally, in some embodiments, special purpose logic circuitry, e.g., an FPGA (field programmable gate array), an ASIC (application-specific integrated circuit), a DSP processor, a graphics processing unit (GPU), application processing unit (APU), etc., may be used in the implementations of the controller device. As noted, similar special purpose logic circuitry may also be used in the implementations of artificial learning networks. Other modules that may be included with the controller device may include a user interface to provide or receive input and output data. Additionally, in some embodiments, sensor devices such as a light-capture device (e.g., a CMOS-based or CCD-based camera device), other types of optical or electromagnetic sensors, sensors for measuring environmental conditions, etc., may be coupled to the controller device, and may be configured to observe or measure the processes and actions being monitored. The controller device may include an operating system.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

In some embodiments, any suitable computer readable media can be used for storing instructions for performing the processes/operations/procedures described herein. For example, in some embodiments computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only Memory (EEPROM), etc.), any suitable media that is not fleeting or not devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications, are considered to be within the scope of the claims provided below. The claims presented are representative of at least some of the embodiments and features disclosed herein. Other unclaimed embodiments and features are also contemplated.

What is claimed is:

1. A method for speech separation comprising:
obtaining, by a device, a combined sound signal for signals combined from multiple sound sources in an area in which a person is located;
obtaining, by the device, neural signals for the person, the neural signals being indicative of one or more target sound sources, from the multiple sound sources, the person is attentive to;
determining a separation filter based, at least in part, on the neural signals obtained for the person; and
applying, by the device, the separation filter to a representation of the combined sound signal to derive a resultant separated signal representation associated with sound from the one or more target sound sources the person is attentive to;
wherein determining the separation filter comprises deriving, using a trained learning model, a time-frequency mask that is applied to a time-frequency representation of the combined sound signal, including deriving the time-frequency mask based on a representation of an estimated target envelope for the one or more target sound sources the person is attentive to, determined based on the neural signals obtained for the person, and based on a representation for the combined sound signal.

2. The method of claim 1, wherein determining the separation filter comprises:
determining based on the neural signals an estimate of an attended sound signal corresponding to the one or more target sound sources the person is attentive to; and
generating the separation filter based, at least in part, on the determined estimate of the attended sound signal.

3. The method of claim 2, wherein determining the estimate of the attended sound signal comprises:
determining, using a learning process, the estimated target envelope for the one or more target sound sources the person is attentive to.

4. The method of claim 1, further comprising:
determining the estimated target envelope for the one or more target sound sources based on a machine-learned mapping process, implemented using regularized linear regression, applied to the obtained neural signals to produce the estimated target envelope.

5. The method of claim 1, wherein deriving the time-frequency mask comprises:
combining the representation of the estimated target envelope with the representation for the combined sound signal to produce a fused signal.

6. The method of claim 5, wherein combining the representation of the estimated target envelope with the representation of the combined sound signal comprises:
transforming the representation of the estimated target envelope into a 3D tensor estimated target envelope representation;
transforming the representation of combined signal into a 3D tensor combined signal representation; and
concatenating the 3D tensor estimated target envelope representation to the 3D tensor combined signal representation to generate a 3D tensor fused signal representation.

7. The method of claim 5, further comprising:
processing the fused signal with a network of convolutional blocks arranged in a stack, wherein each of the convolutional blocks is configured to apply a convolutional process to input received from a respective preceding block, and to generate output comprising a sum of the input from the respective preceding block and output of the respective convolutional process applied to the input received from the preceding block.

8. The method of claim 7, wherein the each of the convolutional blocks comprises one or more convolution operators, at least one of the one or more convolution operators processing input data according to a dilation factor that is based on position of the respective convolutional block within the stack comprising the respective convolutional block.

9. The method of claim 8, wherein the each of the convolutional blocks further comprises one or more ReLU non-linearity elements.

10. The method of claim 1, further comprising:
determining a time-frequency representation for the combined sound signal, including:
applying a short-time Fourier transform to the combined sound signal to generate a transformed combined sound signal; and
compressing the transformed combined sound signal to generate a compressed spectrogram representation of the combined sound signal.

11. The method of claim 10, wherein applying the separation filter to the representation of the combined sound signal comprises:
applying the time-frequency mask to the compressed spectrogram representation of the combined sound signal to generate an output spectrogram; and
inverting the output spectrogram into a time-domain audio output signal.

12. The method of claim 1, wherein obtaining the neural signals for the person comprises measuring the neural signals according to one or more of: invasive intracranial electroencephalography (iEEG) recordings, non-invasive electroencephalography (EEG) recordings, functional near-infrared spectroscopy (fNIRS) recordings, or recordings captured with subdural or brain-implanted electrodes.

13. A system comprising:
- at least one microphone to obtain a combined sound signal for signals combined from multiple sound sources in an area in which a person is located;
- one or more neural sensors to obtain neural signals for the person, the neural signals being indicative of one or more target sound sources, from the multiple sound sources, the person is attentive to; and
- a controller in communication with the at least one microphone and the one or more neural sensors, the controller configured to:
  - determine a separation filter based, at least in part, on the neural signals obtained for the person; and
  - apply the separation filter to a representation of the combined sound signal to derive a resultant separated signal representation associated with sound from the one or more target sound sources the person is attentive to;
- wherein the controller configured to determine the separation filter is configured to derive, using a trained learning model, a time-frequency mask that is applied to a time-frequency representation of the combined sound signal, including to derive the time-frequency mask based on a representation of an estimated target envelope for the one or more target sound sources the person is attentive to, determined based on the neural signals obtained for the person, and based on a representation for the combined sound signal.

14. The system of claim 13, wherein the controller configured to determine the separation filter is configured to:
- determine based on the neural signals an estimate of an attended sound signal corresponding to the one or more target sound sources the person is attentive to; and
- generate the separation filter based, at least in part, on the determined estimate of the attended sound signal.

15. The system of claim 14, wherein the controller configured to determine the estimate of the attended sound signal is configured to:
- determine, using a learning process, the estimated target envelope for the one or more target sound sources the person is attentive to.

16. The system of claim 13, wherein the controller is further configured to:
- determine the estimated target envelope for the one or more target sound sources based on a machine-learned mapping process, implemented using regularized linear regression, applied to the obtained neural signals to produce the estimated target envelope.

17. The system of claim 13, wherein the controller configured to derive the time-frequency mask is configured to:
- combine the representation of the estimated target envelope with the representation for the combined sound signal to produce a fused signal.

* * * * *